(12) United States Patent
Giguere et al.

(10) Patent No.: US 10,189,852 B2
(45) Date of Patent: Jan. 29, 2019

(54) PROCESS FOR IMPROVED OXYMORPHONE SYNTHESIS

(71) Applicant: RHODES TECHNOLOGIES, Coventry, RI (US)

(72) Inventors: Joshua Robert Giguere, Coventry, RI (US); Keith Edward McCarthy, Coventry, RI (US); Marcel Schleusner, Groningen (NL)

(73) Assignee: RHODES TECHNOLOGIES, Coventry, RI (US)

( * ) Notice: Subject to any disclaimer, the term of this patent is extended or adjusted under 35 U.S.C. 154(b) by 0 days.

(21) Appl. No.: 15/944,257

(22) Filed: Apr. 3, 2018

(65) Prior Publication Data

US 2018/0327417 A1 Nov. 15, 2018

Related U.S. Application Data

(62) Division of application No. 15/110,824, filed as application No. PCT/IB2015/050295 on Jan. 15, 2015, now Pat. No. 9,938,285.

(60) Provisional application No. 61/927,938, filed on Jan. 15, 2014.

(51) Int. Cl.
*C07D 489/02* (2006.01)
*C07D 489/08* (2006.01)

(52) U.S. Cl.
CPC ......... *C07D 489/02* (2013.01); *C07D 489/08* (2013.01)

(58) Field of Classification Search
CPC .............................. C07D 489/02; C07D 489/08
See application file for complete search history.

(56) References Cited

U.S. PATENT DOCUMENTS

| | | | |
|---|---|---|---|
| 2,772,270 A | 11/1956 | Weiss | |
| 3,133,132 A | 5/1964 | Loeb et al. | |
| 3,173,876 A | 3/1965 | Zobrist | |
| 3,276,586 A | 10/1966 | Rosaen | |
| 3,541,005 A | 11/1970 | Heinrich et al. | |
| 3,541,006 A | 11/1970 | Harris et al. | |
| 3,546,876 A | 12/1970 | Herman et al. | |
| 3,845,770 A | 11/1974 | Theeuwes et al. | |
| 3,916,899 A | 11/1975 | Theeuwes et al. | |
| 4,063,064 A | 12/1977 | Saunders et al. | |
| 4,088,864 A | 5/1978 | Theeuwes et al. | |
| 4,160,020 A | 7/1979 | Ayer et al. | |
| 4,200,098 A | 4/1980 | Ayer et al. | |
| 4,285,987 A | 8/1981 | Ayer et al. | |
| 4,861,598 A | 8/1989 | Oshlack | |
| 4,957,681 A | 9/1990 | Klimesch et al. | |
| 5,215,758 A | 6/1993 | Krishnamurthy | |
| 5,273,760 A | 12/1993 | Oshlack et al. | |
| 5,286,493 A | 2/1994 | Oshlack et al. | |
| 5,324,351 A | 6/1994 | Oshlack et al. | |
| 5,356,467 A | 10/1994 | Oshlack et al. | |
| 5,472,712 A | 12/1995 | Oshlack et al. | |
| 8,846,923 B1 | 9/2014 | Itov et al. | |
| 9,060,620 B1 | 6/2015 | Patel | |
| 9,062,062 B1 | 6/2015 | Itov et al. | |
| 9,090,620 B2 | 7/2015 | Itov et al. | |
| 9,108,976 B2 | 8/2015 | Itov et al. | |
| 9,233,972 B2 | 1/2016 | Itov et al. | |
| 9,309,257 B2 | 4/2016 | Itov et al. | |
| 2005/0038251 A1 | 2/2005 | Francis et al. | |
| 2006/0111383 A1 | 5/2006 | Casner et al. | |
| 2007/0088162 A1 | 4/2007 | Snuparek et al. | |
| 2007/0117286 A1 | 5/2007 | Jang et al. | |
| 2007/0117826 A1 | 5/2007 | Janjikhel et al. | |
| 2010/0048905 A1 | 2/2010 | Wang et al. | |
| 2010/0324338 A1 | 12/2010 | Maeda et al. | |
| 2013/0253228 A1 | 9/2013 | Tsuda et al. | |
| 2015/0166552 A1 | 6/2015 | Itov et al. | |
| 2015/0166554 A1 | 6/2015 | Itov et al. | |
| 2015/0166556 A1 | 6/2015 | Itov et al. | |
| 2015/0166557 A1 | 6/2015 | Itov et al. | |
| 2015/0259355 A1 | 9/2015 | Gebbie et al. | |
| 2015/0315203 A1* | 11/2015 | Gebbie ................ | C07D 489/08 514/282 |
| 2017/0022210 A1 | 1/2017 | Giguere et al. | |

FOREIGN PATENT DOCUMENTS

| | | |
|---|---|---|
| CA | 2 610 859 A1 | 12/2006 |
| CN | 101198612 A | 6/2008 |
| CN | 103113378 A | 5/2013 |
| CN | 103433076 A | 12/2013 |
| WO | WO-03007802 A2 | 1/2003 |
| WO | WO-2005097801 A1 | 10/2005 |
| WO | WO-2006019364 A1 | 2/2006 |
| WO | WO-2006091885 A2 | 8/2006 |
| WO | WO-2008070656 A2 | 6/2008 |
| WO | WO-2008070658 A1 | 6/2008 |
| WO | WO-2008072018 A1 | 6/2008 |
| WO | WO 2008/118654 A1 | 10/2008 |
| WO | WO-2008130553 A1 | 10/2008 |
| WO | WO-2011032214 A1 | 3/2011 |
| WO | WO-2011117172 A1 | 9/2011 |
| WO | WO-2011154826 A1 | 12/2011 |
| WO | WO 2012/005795 A1 | 1/2012 |
| WO | WO-2012003468 A1 | 1/2012 |
| WO | WO 2013/188418 A1 | 12/2013 |
| WO | WO-2014013311 A1 | 1/2014 |
| WO | WO-2014013313 A1 | 1/2014 |
| WO | WO 2015/095585 A2 | 6/2015 |
| WO | WO-2015107471 A1 | 7/2015 |

OTHER PUBLICATIONS

The United States Pharmacopeial Convention, "USP 34-NF 29, First Supplement, Monograph on Oxycodone Hydrochloride," p. 5016 (Aug. 1, 2011).

(Continued)

*Primary Examiner* — Timothy R Rozof
(74) *Attorney, Agent, or Firm* — Sterne, Kessler, Goldstein & Fox P.L.L.C.

(57) ABSTRACT

Processes for preparing oxymorphone are provided. Said processes encompass a step which is a hydrogenation of an 14-hydroxymorphinone salt in the presence of trifluoroacetic acid and/or a glycol.

16 Claims, 9 Drawing Sheets

(56) References Cited

OTHER PUBLICATIONS

International Preliminary Report on Patentability and Written Opinion for International Application No. PCT/IB2013/001538, WIPO, Geneva, Switzerland, dated Jan. 20, 2015, 15 pages.
International Preliminary Report on Patentability and Written Opinion for International Application No. PCT/IB2013/001541, WIPO, Geneva, Switzerland, dated Jan. 20, 2015, 15 pages.
International Preliminary Report on Patentability for International Application No. PCT/IB2015/050294, WIPO, Geneva, Switzerland, dated Jul. 19, 2016, 7 pages.
International Preliminary Report on Patentability for International Application No. PCT/IB2015/050295, WIPO, Geneva, Switzerland, dated Jul. 19, 2016, 7 pages.
International Search Report for International Application No. PCT/IB2013/001538, European Patent Office, Rijswijk, Netherlands, dated Nov. 19, 2013, 9 pages.
International Search Report for International Application No. PCT/IB2013/001541, European Patent Office, Rijswijk, Netherlands, dated May 12, 2013, 7 pages.
International Search Report and Written Opinion for International Application No. PCT/IB2015/050294, European Patent Office, Netherlands, dated Mar. 16, 2015, 10 pages.
International Search Report and Written Opinion for International Application No. PCT/IB2015/050295, European Patent Office, Netherlands, dated Mar. 16, 2015, 10 pages.
King, R.E., "Chapter 89: Tablets, Capsules, and Pills," in *Remington's Pharmaceutical Sciences*, Arthur Osol, ed., pp. 1553-1584, Mack Publishing Company, United States (1980).
Kok, G.B. and Scammells, P.J., "Improved Synthesis of 14-hydroxy Opioid Pharmaceuticals and Intermediates," *RSC Advances* 2(30):11318-11325, The Royal Society of Chemistry, England (2012).
Maxwell, G.M., "The Central Nervous System," in *Principles of Paediatric Pharmacology*, Maxwell, G.M., ed., p. 126, Oxford University Press, England (1984).
Office Action dated Dec. 22, 2015, in U.S. Appl. No. 14/413,360, Gebbie et al., having a 35 U.S.C. § 371(c) date of Jan. 7, 2015.
Office Action dated Jul. 6, 2016, in U.S. Appl. No. 14/413,360, Gebbie et al., having a 35 U.S.C. § 371(c) date of Jan. 7, 2015.
Robinson, M.J., "Chapter 90: Coating of Pharmaceutical Dosage Forms," in *Remington's Pharmaceutical Sciences*, Arthur Osol, ed., pp. 1585-1593, Mack Publishing Company, United States (1980).
Seher, A. and Lange, J., "Gemeinschaftsarbeiten der DGF, 60. Mitteilung, Deutsche Einheitsmethoden zur Untersuchung von Fetten, Fettprodukten und verwandten Stoffen, 45. Mitt.: Analyse von Wachsen und Wachsprodukten X," *Fette, Seifen, Anstrichmittel* 76(3):135, Wiley-VCH Verlag GmbH & Co., Germany (1974).
Weiss, U., "Derivatives of Morphine. II. Demethylation of 14-hydroxycodeinone. 14-Hydroxymorphinone and 8,14-Dihydroxydihydromorphinone," *J. Org. Chem.* 22(11):1505-1508, American Chemical Society, United States (1957).
Yang, J.W., et al., "A Metal-Free Transfer Hydrogenation: Organocatalytic Conjugate Reduction of α,β-Unsaturated Aldehydes," *Angew. Chem. Int. Ed.* 43(48):6660-6662, Wiley-VCH Verlag GmbH & Co., Germany (2004).
Devi, R.B., et al., "Domino alkylation/oxa-Michael of 1,3-cyclohexanediones: Steering the C/O-chemoselectivity to reach tetrahydrobenzofuranones," *Organic & Biomolecular Chemistry* 9(19):6509-6512, The Royal Society of Chemistry, England (2011).
Haynes, D.A., et al., "Occurrence of pharmaceutically acceptable anions and cations in the Cambridge Structural Database," Journal of Pharmaceutical Sciences 94(10):2111-2120, Wiley-Liss, Inc., United States (2005).
Liu, M-Q., et al., "Synthesis of Long-Acting Analgetic Hydrazone Derivatives of 14-Hydroxycodeinone and 14-Hydroxymorphinone," *Acta Pharmaceutica Sinica* 18(6):475-477, China Academic Journal Electronic Publishing House, China (1983).
Sevillano, L.G., et al., "Synthesis of B,B-dinor-B-secosteroids as potential cardenolide analogues," Tetrahedron 58:10103-10112, Elsevier Science Ltd., England (2002).
Watson, C.P.N., et al., "Controlled-release oxycodone relieves neuropathic pain: a randomized controlled trial in painful diabetic neuropathy," Pain 105(1-2):71-78, Elsevier Science B.V., Netherlands (2003).
Zhang, B. et al., "Oxycodone Hydrochloride," *Chinese Journal of Medicinal Chemistry* 21(2):166, China Academic Journal Electronic Publishing House, China (2011).
Office Action dated Jan. 4, 2017, in U.S. Appl. No. 14/413,362, Gebbie et al., having a 35 U.S.C. § 371(c) date of Jan. 7, 2015.
Office Action dated Jul. 12, 2017, in U.S. Appl. No. 14/413,362, Gebbie et al., having a 35 U.S.C. § 371(c) date of Jan. 7, 2015.
Office Action dated Jun. 12, 2017, in U.S. Appl. No. 14/413,360, Gebbie et al., having a 35 U.S.C. § 371(c) date of Jan. 7, 2015.
Office Action dated May 30, 2017, in U.S. Appl. No. 15/110,825, Giguere et al., having a 35 U.S.C. § 371(c) date of Jul. 11, 2016.
English language Abstract of Chinese Patent Publication No. CN 103113378 A, Espacenet database—Worldwide, European Patent Office (listed as document FP17 on the accompanying form PTO/SB/08A) (2013).
English language Abstract of Chinese Patent Publication No. CN 103433076 A, Espacenet database—Worldwide, European Patent Office (listed as document FP18 on the accompanying form PTO/SB/08A) (2013).
Office Action dated May 31, 2018, in U.S. Appl. No. 14/413,362, Gebbie et al., having a 35 U.S.C. § 371(c) date of Jan. 7, 2015.
Notice of Allowance dated Nov. 30, 2017, in U.S. Appl. No. 15/110,824, Giguere et al., having a 35 U.S.C. § 371(c) date of Jul. 11, 2016.
Notice of Allowance dated Nov. 22, 2017, in U.S. Appl. No. 15/110,825, Giguere et al., having a 35 U.S.C. § 371(c) date of Jul. 11, 2016.

\* cited by examiner

PROCESS FOR IMPROVED OXYMORPHONE SYNTHESIS

The present invention is in the field of oxymorphone synthesis. It provides processes for preparing oxymorphone, in particular oxymorphone base. The resulting oxymorphone base may be used in the preparation of APIs like oxymorphone hydrochloride. Said APIs may be used in pharmaceutical dosage forms.

BACKGROUND OF THE INVENTION

Oxymorphone and its hydrochloride salt have long been used as analgesics.

Oxymorphone base is conventionally prepared by O-demethylation of oxycodone. Oxymorphone base can also be prepared by oxidation of oripavine to 14-hydroxymorphinone, and reducing the 14-hydroxymorphinone to oxymorphone base. A route for the preparation of oxymorphone via oxidation of oripavine to 14-hydroxymorphinone is illustrated in Scheme 1:

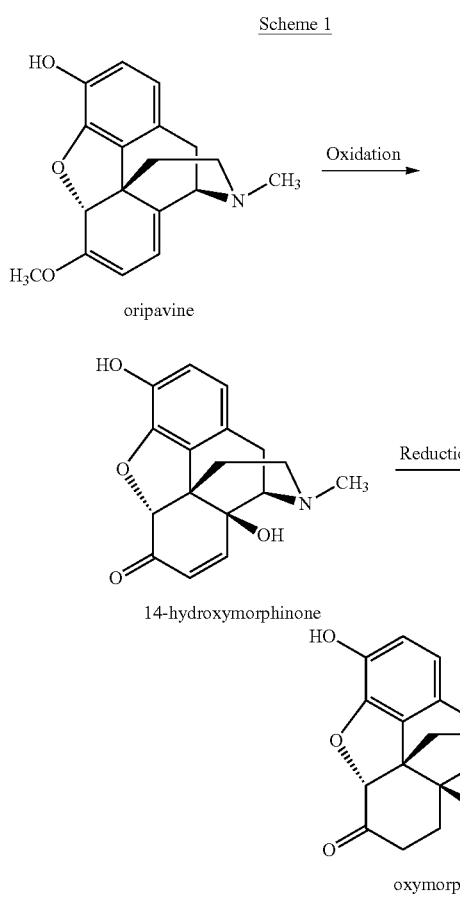

Once the oxymorphone base has been prepared, it is usually reacted with an acid to produce an oxymorphone salt, typically oxymorphone hydrochloride (which is the API form in which oxymorphone is generally used therapeutically), as shown below in Scheme 2:

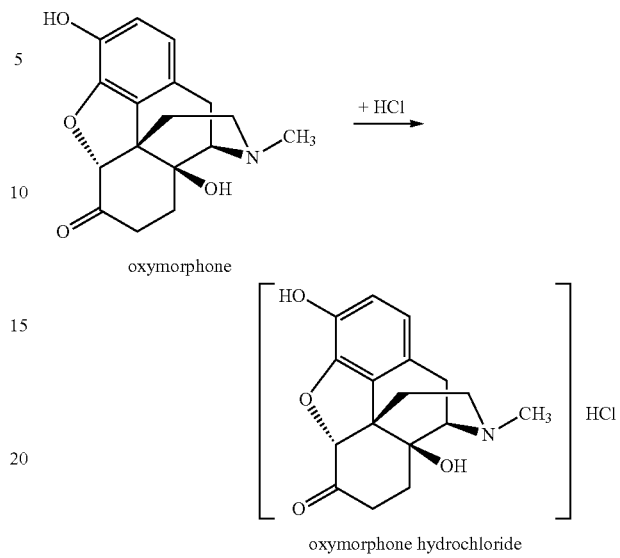

The oxidation step in the synthetic route illustrated in Scheme 1 can yield by-products which may be converted into other by-products during further conversion of the oxidation product (e.g., during the reaction shown in Scheme 2) or may be carried over into the final oxymorphone salt or other opioid made from the oxymorphone base, final pharmaceutical composition or final dosage form. These by-products may be undesired in the final pharmaceutical composition or final dosage form. Separation of these by-products from the final product may often be difficult, time-consuming and not volume efficient (e.g., if a separation by HPLC is required).

For example, during oxidation of oripavine to 14-hydroxymorphinone, certain by-products can be formed, in particular 8-hydroxyoxymorphone:

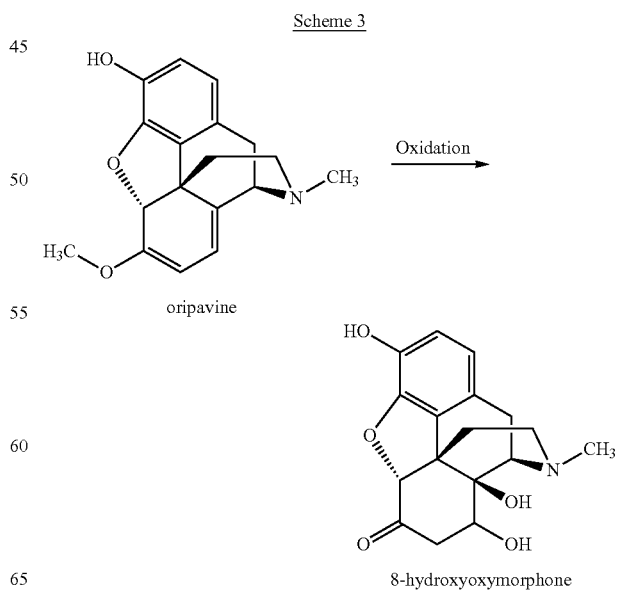

The 8-hydroxyoxymorphone can be converted to 14-hydroxymorphinone when HCl is added, as illustrated in Scheme 4:

Scheme 4

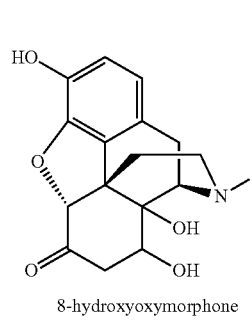

8-hydroxyoxymorphone

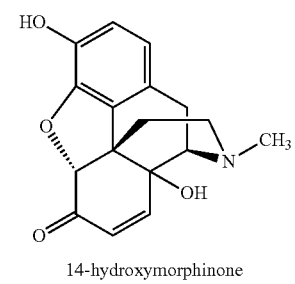

14-hydroxymorphinone

Thus, the 14-hydroxymorphinone intermediate shown in Scheme 1 is not only the immediate precursor to oxymorphone, it is also often found in the final oxymorphone salt used in pharmaceutical compositions, which is usually oxymorphone hydrochloride. 14-hydroxymorphinone belongs to a class of compounds known as α,β-unsaturated ketones (ABUKs). These compounds contain a substructural component (the α,β-unsaturated ketone component) which produces a structure-activity relationship alert for genotoxicity. Their presence may be undesired in a pharmaceutical composition. Some regulatory authorities do not approve a pharmaceutical composition or dosage form for use and sale to the public if the amount of ABUKs in the pharmaceutical composition or dosage form exceeds the amount set by these authorities.

In PCT/IB2013/001541 reactions are described which allow reduction of the amount of undesired by-products caused by the oxidation step. In particular, PCT/IB2013/001541 describes the performance of the oxidation reaction in the presence of an acid $H_nX^{n-}$, e.g. $H_2SO_4$, such that a 14-hydroxymorphinone salt with $X^{n-}$, e.g. $SO_4^{2-}$, as counterion is formed:

Scheme 5

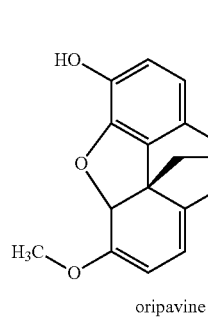

oripavine

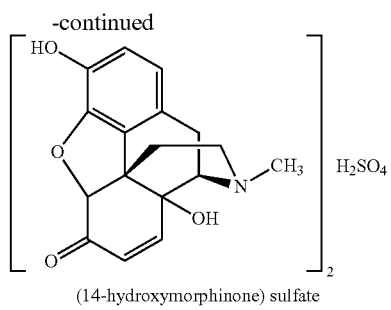

(14-hydroxymorphinone) sulfate

However, even under these reaction conditions, some 8-hydroxyoxymorphone might be carried over into oxymorphone in a subsequent reduction reaction.

Even in spite of the improvements achieved by recent developments like the processes described in PCT/IB2013/001541, there is still a continuing need for processes for preparing oxymorphone which exhibit a reduced amount of by-products in the final product. In particular, a process for preparing oxymorphone base with a reduced amount of 8-hydroxyoxymorphone, preferably with no (detectable) 8-hydroxyoxymorphone would be advantageous.

SUMMARY OF THE INVENTION

The present invention provides a hydrogenation process for preparing oxymorphone from 14-hydroxymorphinone, which process is suitable to reduce or even completely suppress the presence of undesired byproducts of the oxidation reaction leading from oripavine to 14-hydroxymorphinone, in particular of 8-hydroxyoxymorphone, in the resulting oxymorphone.

The hydrogenation process according to the invention is useful for preparing oxymorphone base from 14-hydroxymorphinone sulfate which was made via an oxidation process as described above. Even if this starting material contains 8-hydroxyoxymorphone, the resulting oxymorphone base made via the hydrogenation process according to the invention contains very small amounts or even no detectable amounts of 8-hydroxyoxymorphone. It also contains very small amounts or even no detectable amounts of 14-hydroxymorphinone, which can be formed from 8-hydroxyoxymorphone under acidic conditions (like the acidic conditions of the hydrogenation process).

In one aspect, the present invention provides a process for preparing oxymorphone or an (optionally pharmaceutically acceptable) salt or solvate thereof, the process comprising or consisting of a conversion of a 14-hydroxymorphinone salt or a solvate thereof to oxymorphone or salt or solvate thereof, by hydrogenation of the 14-hydroxymorphinone salt or solvate thereof in the presence of trifluoroacetic acid (abbreviated as "TFA") and/or a glycol. Preferably, both trifluoroacetic acid and a glycol are present during the hydrogenation. In said process, the 14-hydroxymorphinone salt or a solvate thereof may be used as a starting material or as an intermediate material. In each of these cases, said 14-hydroxymorphinone salt or solvate thereof may be prepared by the following process starting from oripavine as described in PCT/IB2013/001541 (see also detailed description of the present invention below):

Scheme 6

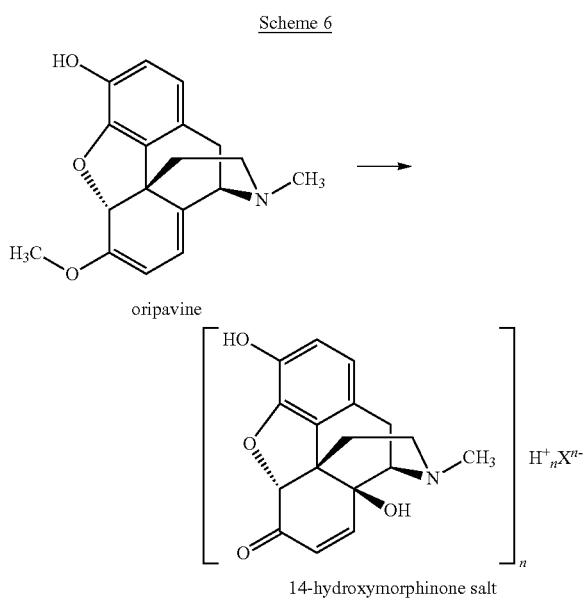

14-hydroxymorphinone salt

The process for preparing oxymorphone or an (optionally pharmaceutically acceptable) salt or solvate thereof according to the present invention is represented by the following reaction Scheme 7:

Scheme 7

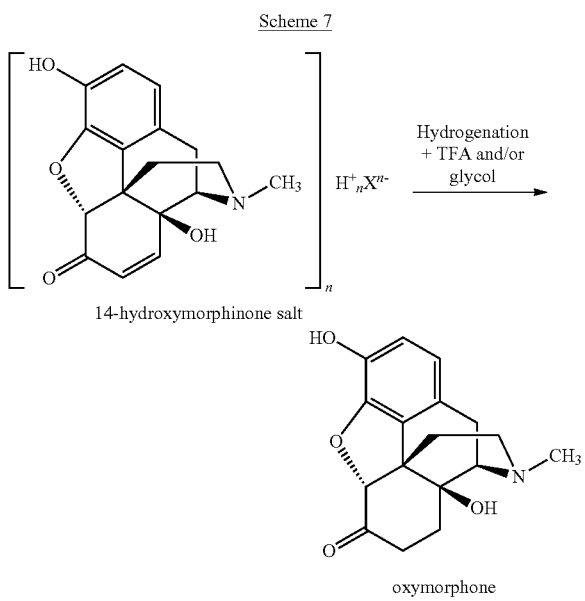

oxymorphone wherein
$X^{n-}$ is an anion selected from the group consisting of $Cl^-$, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof; and
n is 1, 2, or 3.

Preferably, $X^{n-}$ is $SO_4^{2-}$. So, the 14-hydroxymorphinone salt is preferably 14-hydroxymorphinone sulfate.

Given the ingredients of the hydrogenation reaction, depending on the subsequent workup the resulting oxymorphone could be isolated (1) as free base, (2) as salt with $X^{n-}$ as anion, (3) as oxymorphone trifluoroacetate, or (4) as a salt with a combination of $X^{n-}$ and trifluoroacetate as anion. In a preferred embodiment of the present invention, it is isolated as free base.

The 14-hydroxymorphinone salt is represented by the following structure:

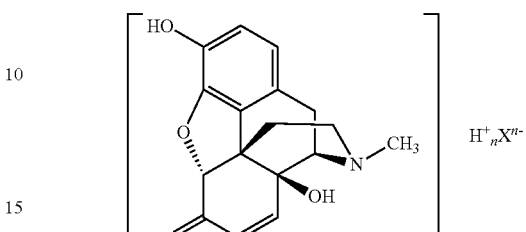

wherein $X^{n-}$ and n are defined as above.

In one embodiment, the 14-hydroxymorphinone salt is

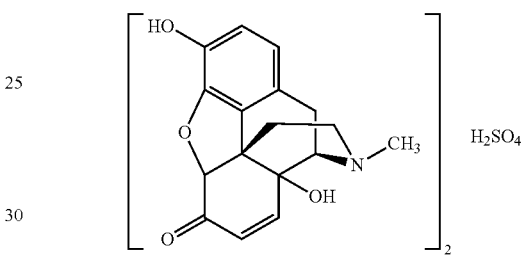

or a solvate thereof. In the context of the present invention, this compound will be designated as 14-hydroxymorphinone sulfate. Because of its stoichiometric composition, it may also be designated as bis(14-hydroxymorphinone)sulfate. The terms 14-hydroxymorphinone sulfate and bis(14-hydroxymorphinone)sulfate are used interchangeably in the context of the present invention.

In the 14-hydroxymorphinone salt, the 14-hydroxymorphinone is typically protonated by a proton ($H^+$), and thus forms a cation. For example, when n=2, the two protons and two molecules of 14-hydroxymorphinone which are present in the 14-hydroxymorphinone salt form two cations of 14-hydroxymorphinone in its protonated form.

According to the present invention, the hydrogenation is performed in the presence of trifluoroacetic acid and/or a glycol. In a preferred embodiment, TFA is present, and preferably in a substoichiometric amount. In another preferred embodiment, glycol is present. Even more preferably, both glycol and TFA are present, wherein TFA is preferably present in a substoichiometric amount.

Preferably, the glycol is selected from the group consisting of ethylene glycol, propylene glycol, 1,3-propanediol, 1,2-butanediol, 1,3-butanediol, neopentylglycol, and mixtures thereof. More preferably, the glycol is ethylene glycol, propylene glycol, or a mixture thereof.

The advantages of the hydrogenation reaction characterizing the process of the present invention are explained in the following: The presence of trifluoroacetic acid and glycol during hydrogenation has the technical effect that less 8-hydroxyoxymorphone will be present in the reaction product than in a reaction product made in the absence of trifluoroacetic acid and glycol. As shown in Example 16, by performing the hydrogenation in the presence of trifluoroacetic acid and glycol, even oxymorphone without any detectable amount of 8-hydroxyoxymorphone or 14-hydroxymorphinone can be prepared from a starting material containing 8-hydroxyoxymorphone. Said 8-hydroxyoxymorphone is an undesired by-product of the oxidation of oripavine to 14-hydroxymorphinone, and it is carried over into the final oxymorphone in conventional reduction reactions leading from 14-hydroxymorphinone (made by oxidation of oripavine) to oxymorphone. The hydrogenation reaction of the present invention can reduce or even completely suppress this carryover. Without being bound by theory, the reaction conditions of the hydrogenation reaction, in particular the low content of acid (typically a substoichiometric amount of TFA is used) in the reaction mixture, might also prevent acid-catalyzed conversion of 14-hydroxymorphinone into 8-hydroxyoxymorphone during the hydrogenation reaction. Moreover, 8-hydroxyoxymorphone might be more soluble in the reaction solvent (which contains the glycol characterizing the hydrogenation reaction of the present invention) than oxymorphone base or an oxymorphone salt. Thus, oxymorphone or a salt thereof can be purified from 8-hydroxyoxymorphone by precipitation. A preferred embodiment of the present invention makes use of this effect by precipitating and isolating the oxymorphone base.

Processes using a 14-hydroxymorphinone trifluoroacetate salt as starting material for a reduction reaction are already described in PCT/IB2013/001541. However, for performing the process of the present application, it is sufficient to use trifluoroacetic acid in substoichiometric amounts (less than 1 molar equivalent of 14-hydroxymorphinone), together with a different 14-hydroxymorphinone salt, e.g., 14-hydroxymorphinone sulfate.

In certain embodiments, trifluoroacetic acid is the sole acid added to the hydrogenation reaction mixture, and it is added in substoichiometric amounts, i.e. less than 100 mol % of the 14-hydroxymorphinone in the starting material 14-hydroxymorphinone salt. This can greatly reduce the amount of base which has to be added to precipitate the oxymorphone free base after the hydrogenation reaction. As already mentioned above, this low amount of acid in the reaction mixture might also prevent acid-catalyzed conversion of 14-hydroxymorphinone into 8-hydroxyoxymorphone during the hydrogenation reaction.

A process according to the present invention comprises the steps of providing a solution or suspension of the 14-hydroxymorphinone salt or a solvate thereof; adding trifluoroacetic acid and/or a glycol; and subsequently hydrogenating the 14-hydroxymorphinone to the oxymorphone, which may then be isolated as its base or as an (optionally pharmaceutically acceptable) salt or solvate thereof.

Hence, the present invention provides a process for preparing oxymorphone or a salt or solvate thereof from a 14-hydroxymorphinone salt or a solvate thereof

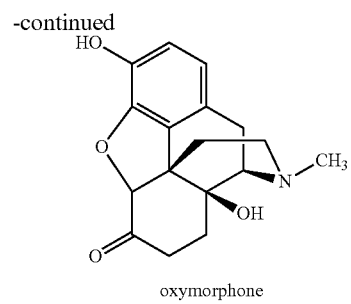

oxymorphone the process comprising or consisting of the steps of
(a) providing a solution or suspension of the 14-hydroxymorphinone salt or a solvate thereof;
(b) adding trifluoroacetic acid and/or a glycol, preferably trifluoroacetic acid and a glycol; and
(c) hydrogenating the resulting mixture, thus reducing the 14-hydroxymorphinone to oxymorphone,
wherein $X^{n-}$ and n are defined as above.

After the hydrogenation reaction, the oxymorphone may be present as its salt or solvate in the reaction mixture, e.g., as its sulfate salt and/or trifluoroacetate salt. In a subsequent step, it may be converted into its free base and/or converted into a different salt or solvate, e.g., a pharmaceutically acceptable salt or solvate. It may be isolated from the reaction mixture in one or more of these forms.

In a preferred embodiment, the oxymorphone is isolated from the reaction mixture as free base, e.g. by precipitation and subsequent isolation of the precipitate. In said embodiment, the process may be represented by the following reaction scheme:

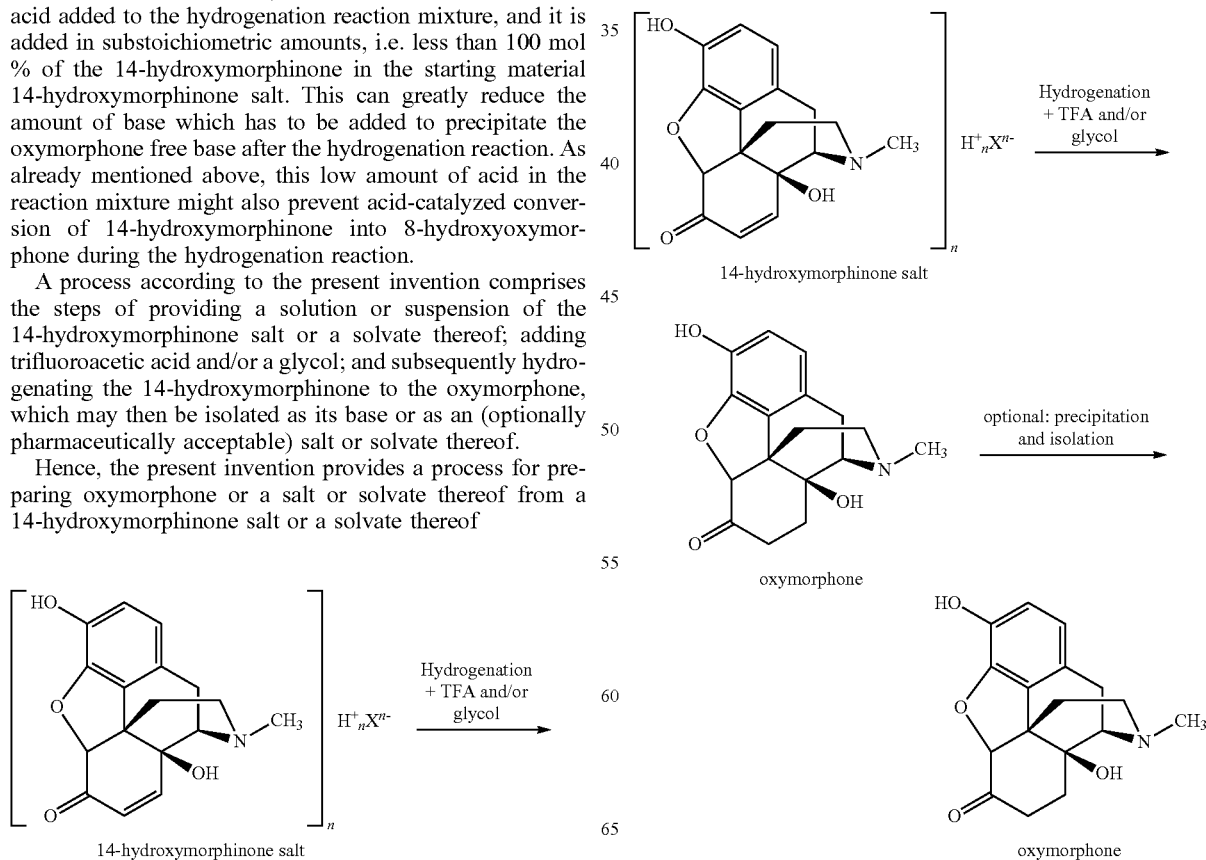

the process comprising or consisting of the steps of
(a) providing a solution or suspension of the 14-hydroxymorphinone salt or a solvate thereof;
(b) adding trifluoroacetic acid and/or a glycol, preferably trifluoroacetic acid and a glycol; and
(c) hydrogenating the resulting mixture, thus reducing the 14-hydroxymorphinone to the oxymorphone; and
(d) adding a base, thus raising the pH to a pH where the oxymorphone precipitates, and isolating the oxymorphone as its free base or a solvate thereof,
wherein $X^{n-}$ and n are defined as above, and $X^{n-}$ is preferably $SO_4^{2-}$.

In a preferred aspect of this process, 14-hydroxymorphinone sulfate (or a solvate thereof) is converted into oxymorphone base (or a solvate thereof).

Usually, the oxymorphone resulting from a conventional reduction of a 14-hydroxymorphinone salt (e.g., 14-hydroxymorphinone sulfate) may contain certain by-products, as shown in the following Scheme 8:

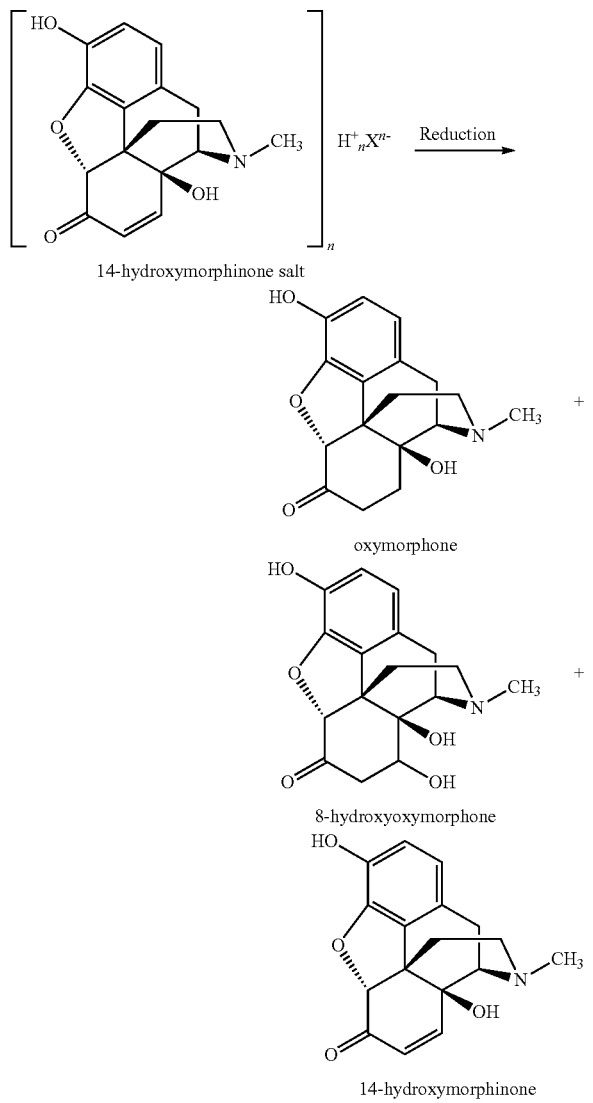

8-Hydroxyoxymorphone is undesired in the final oxymorphone because it may convert to 14-hydroxymorphinone, an ABUK, under acidic conditions, in particular when oxymorphone is converted to oxymorphone hydrochloride (the API). Apart from 8-hydroxyoxymorphone, 14-hydroxymorphinone is also undesired in the final oxymorphone. Such 14-hydroxymorphinone may be unreacted starting material, or it may be formed from 8-hydroxyoxymorphone because of the presence of acid in the hydrogenation mixture during the hydrogenation or after the hydrogenation reaction has been stopped. It is an advantage of the present invention that the hydrogenation reaction according to the present invention allows formation of oxymorphone which does neither contain 14-hydroxymorphinone nor 8-hydroxyoxymorphone.

The hydrogenation reaction characterizing the process of the present invention is suitable for reducing the amount of 8-hydroxyoxymorphone and/or 14-hydroxymorphinone in the resulting oxymorphone or salt or solvate thereof, in comparison to processes utilizing a different reduction or hydrogenation reaction which also starts with 14-hydroxymorphinone salt as starting material, and especially in comparison to processes not utilizing a salt of 14-hydroxymorphinone, in particular not 14-hydroxymorphinone sulfate, as starting material.

The hydrogenation process of the present invention differs from the hydrogenation described in PCT/IB2013/001541 and similar prior art hydrogenations in that TFA and/or glycol, preferably both TFA and glycol are present during the hydrogenation. This has the surprising effect that the resulting oxymorphone base contains very small amounts or even no detectable amounts of 8-hydroxyoxymorphone. It also contains very small amounts or even no detectable amounts of 14-hydroxymorphinone, which can be formed from 8-hydroxyoxymorphone under acidic conditions (like the acidic conditions of the hydrogenation process).

It may also be because of the use of the 14-hydroxymorphinone salt as starting material for said hydrogenation reaction that the process of the present invention is suitable for reducing the amount of 14-hydroxymorphinone and/or 8-hydroxyoxymorphone in oxymorphone or a salt or solvate thereof prepared from said 14-hydroxymorphinone salt, in comparison to processes using other intermediates or starting materials. 14-hydroxymorphinone salt made from oripavine, e.g. according to the processes described in PCT/IB2013/001541, contains reduced amounts of 8-hydroxyoxymorphone in comparison to 14-hydroxymorphinone made via other routes from oripavine. The lower amount of 8-hydroxyoxymorphone in the 14-hydroxymorphinone salt may result in less 8-hydroxyoxymorphone in oxymorphone made from said 14-hydroxymorphinone salt, which in turn may result in less 14-hydroxymorphinone in an oxymorphone salt made from said oxymorphone, because 14-hydroxymorphinone can be formed from 8-hydroxyoxymorphone during the conversion of oxymorphone to a salt thereof by acid addition.

In those embodiments of the present invention which encompass precipitation and isolation of the oxymorphone as free base, typically, at least some 8-hydroxyoxymorphone or salt or solvate thereof remains in the supernatant. Thus, a separation of the 8-hydroxyoxymorphone from the oxymorphone or solvate thereof may be achieved by the precipitation. The precipitated and optionally isolated precipitate, which contains the oxymorphone base or the solvate thereof, may contain a lower ratio of the 8-hydroxyoxymorphone to the oxymorphone than the ratio of the 8-hydroxyoxymorphone to the oxymorphone in the mother liquor.

8-hydroxyoxymorphone has the following formula:

8-hydroxyoxymorphone

The stereoconfiguration at C-8 of 8-hydroxyoxymorphone can be either alpha (8α) or beta (8β). The 8α and 8β stereoconfiguration are shown for 8-hydroxyoxymorphone in Scheme 9. The 8-hydroxyoxymorphone may be the 8α compound, or the 8β compound, or a mixture of the 8α-hydroxyoxymorphone and the 8β-hydroxyoxymorphone.

Scheme 9

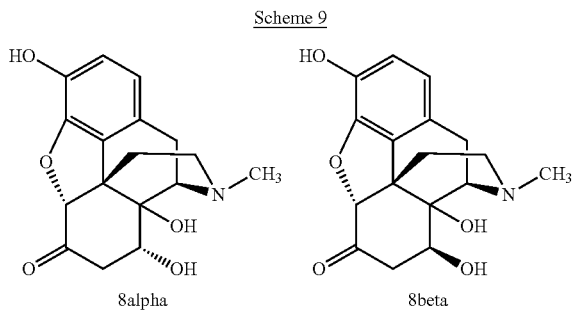 [SMILES: CN1CC[C@]23c4c5ccc(O)c4O[C@H]2C(=O)C[C@@H](O)C3(O)[C@H]1C5 ; CN1CC[C@]23c4c5ccc(O)c4O[C@H]2C(=O)C[C@H](O)C3(O)[C@H]1C5]

8alpha          8beta

Pharmaceutical compositions prepared by processes of the present invention may be quantitatively different from pharmaceutical compositions prepared by conventional processes which do not utilize the hydrogenation of 14-hydroxymorphinone salt according to the present invention, and may offer advantages over the compositions prepared by conventional processes, e.g., in terms of safety, efficiency and reduced manufacturing costs. For example, these compositions may contain less by-products and/or require less or no further processing steps after synthesis of their API.

Moreover, the hydrogenation reaction according to the present invention may allow for a more volume efficient process, as compared to the conventional hydrogenation reaction. The use of a substoichiometric amount of trifluoroacetic acid (instead of, e.g. formic acid as an excess reagent as described in conventional hydrogenation reactions, which generally use >5 molar equivalents of formic acid) requires the addition of less base after the hydrogenation if the oxymorphone shall be precipitated as its free base. This reduces the amount of base required, and also makes the reaction more volume efficient.

Oxymorphone or an (optionally pharmaceutically acceptable) salt or solvate thereof are also provided by the present invention. Oxymorphone, when prepared by a process according to present invention, may comprise only very low amounts of 8-hydroxyoxymorphone and/or 14-hydroxymorphinone. As explained above, under the conditions described in the prior art, 14-hydroxymorphinone may be formed from 8-hydroxyoxymorphone when preparing the oxymorphone or a salt or solvate thereof. In particular, the oxymorphone or the pharmaceutically acceptable salt or solvate thereof according to the present invention may comprise an amount of 14-hydroxymorphinone which is below a desired threshold amount, e.g., a threshold amount mandated by the regulatory authorities for the approval of pharmaceutical compositions for use and sale to the public, and/or it comprises an amount of 8-hydroxyoxymorphone which is insufficient to increase the amount of 14-hydroxymorphinone or a salt or solvate thereof, upon further processing of the oxymorphone or a salt or solvate thereof, above said threshold amount.

The present invention further provides pharmaceutical compositions and dosage forms, which comprise oxymorphone or a pharmaceutically acceptable salt or solvate thereof (e.g., oxymorphone hydrochloride). Said oxymorphone is preferably prepared by the process according to the present invention. In certain embodiments, these pharmaceutical compositions have a different by-product profile and may have a different efficacy than pharmaceutical compositions prepared via a different reduction reaction, rather than via the hydrogenation reaction of the present invention. In particular, the content of the 14-hydroxymorphinone in these pharmaceutical compositions differs from the content of the 14-hydroxymorphinone in pharmaceutical compositions prepared via the free base of 14-hydroxymorphinone, rather than via the 14-hydroxymorphinone salt or a solvate thereof. This encompasses pharmaceutical compositions comprising oxymorphone or the pharmaceutically acceptable salt or solvate thereof and 14-hydroxymorphinone or a salt or solvate thereof in an amount which is below a desired threshold amount, e.g., a threshold amount mandated by the regulatory authorities for the approval of these compositions for use and sale to the public. It also encompasses pharmaceutical compositions comprising, in addition to the oxymorphone or the pharmaceutically acceptable salt or solvate thereof, 8-hydroxyoxymorphone or a salt or solvate thereof in an amount which is insufficient to increase the levels of 14-hydroxymorphinone or a salt or solvate thereof, upon further processing of the pharmaceutical composition, above said desired threshold amount of the 14-hydroxymorphinone. It also encompasses pharmaceutical compositions comprising, in addition to the oxymorphone or the pharmaceutically acceptable salt or solvate thereof, 14-hydroxymorphinone or a salt or solvate thereof, and 8-hydroxyoxymorphone or a salt or solvate thereof, wherein the 8-hydroxyoxymorphone is present in an amount which is insufficient to increase the levels of the 14-hydroxymorphinone, upon further processing as described in the prior art, above said desired threshold amount.

The present invention is further directed to pharmaceutical compositions and dosage forms formed as the result of carrying out the processes of the invention, as well as methods for using these pharmaceutical compositions and dosage forms in the treatment of medical conditions. The immediate products formed by carrying out the processes of the invention may be suitable as pharmaceutical compositions themselves, without further processing steps.

These pharmaceutical compositions and dosage forms can be used to treat or prevent one or more of the following medical conditions: pain, addiction, cough, constipation, diarrhea, insomnia associated with and/or caused by pain, cough or addiction, depression associated with and/or resulting from pain, cough or addiction, or a combination of two or more of the foregoing conditions, etc. A method for treatment or prevention of one or more of these conditions by administration of oxymorphone or a salt or solvate thereof to a patient is also provided by the present invention.

The use of a pharmaceutical composition or dosage form according to the present invention, comprising oxymorphone or a pharmaceutically acceptable salt or solvate thereof, in the manufacture of a medicament for the treatment of one or more of these medical conditions is also part of the present invention.

Certain Embodiments of the Invention

The present invention encompasses the following embodiments:

(1) A process for preparing oxymorphone or a salt or solvate thereof from a 14-hydroxymorphinone salt or a solvate thereof

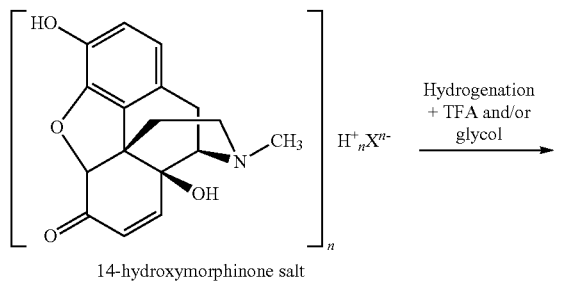

14-hydroxymorphinone salt

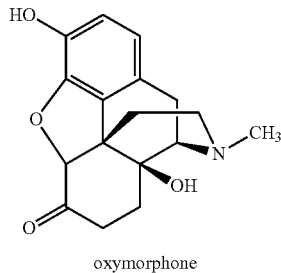

oxymorphone the process comprising or consisting of the steps of
(a) providing a solution or suspension of the 14-hydroxymorphinone salt or a solvate thereof;
(b) adding trifluoroacetic acid and/or a glycol; and
(c) hydrogenating the resulting mixture, thus reducing the 14-hydroxymorphinone to the oxymorphone, wherein
$X^{n-}$ is an anion selected from the group consisting of $Cl^-$, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof; and
n is 1, 2, or 3.

(2) The process of (1), wherein trifluoroacetic acid and a glycol are added in step (b).

(3) The process of (1) or (2), wherein n is 2 and $X^{n-}$ is $SO_4^{2-}$.

(4) The process of any one of (1) to (3), wherein the amount of trifluoroacetic acid is 99 mol % or less as compared to the molar amount of 14-hydroxymorphinone contained in the 14-hydroxymorphinone salt.

(5) The process of (4), wherein the amount of trifluoroacetic acid is from 30 mol % to 50 mol % as compared to the molar amount of 14-hydroxymorphinone contained in the 14-hydroxymorphinone salt.

(6) The process of any one of (1) to (5), wherein the glycol is selected from the group consisting of ethylene glycol, propylene glycol, 1,3-propanediol, 1,2-butanediol, 1,3-butanediol, neopentylglycol, and mixtures thereof.

(7) The process of (6), wherein the glycol is ethylene glycol, propylene glycol, or a mixture thereof.

(8) The process of (7), wherein the glycol is ethylene glycol.

(9) The process of (7), wherein the glycol is propylene glycol.

(10) The process of any one of (1) to (9), wherein the glycol added in step (b) is in the range of 1 to 8 volumes in mL in relation to the weight in g of the 14-hydroxymorphinone salt.

(11) The process of any one of (1) to (10), wherein the hydrogenation in step (c) is performed with $H_2$ and a hydrogenation catalyst.

(12) The process of (11), wherein the hydrogenation catalyst is Pd/C.

(13) The process of any one of (1) to (12), wherein a mixture of water and the glycol is used as solvent.

(14) The process of (13), wherein the mixture is in a range from 20:80 to 45:55 glycol:water.

(15) The process of (14), wherein the mixture is about 40:60 glycol:water.

(16) The process of any one of (1) to (15), additionally comprising the step:
(d) adding a base, thus raising the pH to a pH where the oxymorphone precipitates as its free base, and isolating the oxymorphone as its free base or a solvate thereof.

(17) The process of (16), wherein the base added in step (d) is NaOH.

(18) A process for preparing oxymorphone or a salt or solvate thereof from oripavine, the process comprising or consisting of the steps

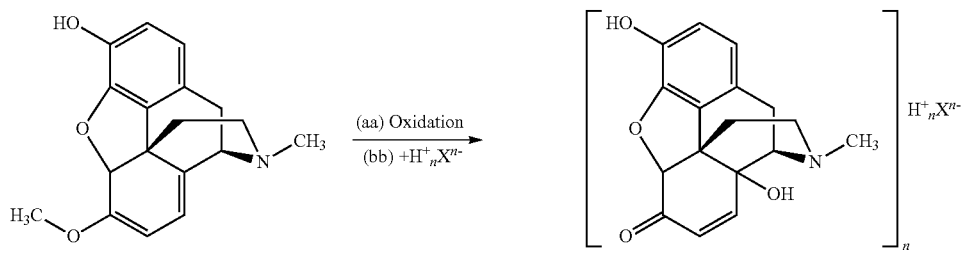

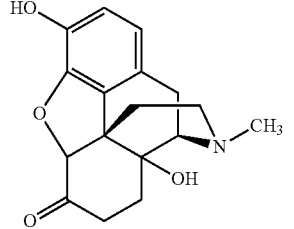

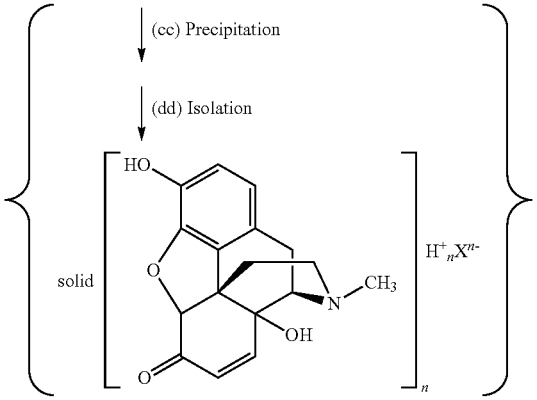

(aa) oxidizing the oripavine to 14-hydroxymorphinone;
(bb) adding an acid to the reaction mixture before, during and/or after the oxidation reaction;
(cc) optionally precipitating the resulting 14-hydroxymorphinone as 14-hydroxymorphinone salt or a solvate thereof;
(dd) optionally isolating the precipitated 14-hydroxymorphinone salt or solvate thereof; and
(ee) performing the process according to any one of (1) to (17),
wherein
$X^{n-}$ is an anion selected from the group consisting of $Cl^-$, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof; and
n is 1, 2, or 3.

(b) adding trifluoroacetic acid and/or a glycol; and
(c) hydrogenating the resulting mixture, thus reducing the 14-hydroxymorphinone to the oxymorphone.

(21) The process of (1), wherein said process consists of the steps of
(a) providing a solution or suspension of the 14-hydroxymorphinone salt or a solvate thereof;
(b) adding trifluoroacetic acid and/or a glycol; and
(c) hydrogenating the resulting mixture, thus reducing the 14-hydroxymorphinone to the oxymorphone.

(22) The process of (18), wherein said process comprises the steps

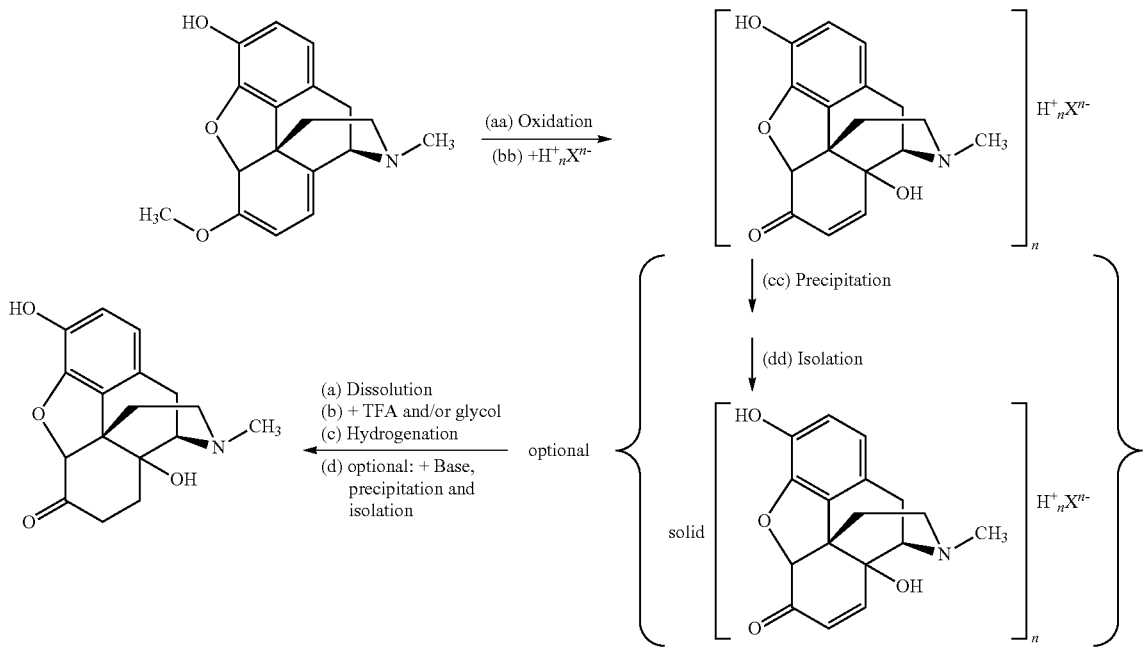

(19) The process of (18), wherein n is 2 and $X^{n-}$ is $SO_4^2$
(20) The process of (1), wherein said process comprises the steps of
(a) providing a solution or suspension of the 14-hydroxymorphinone salt or a solvate thereof;

(aa) oxidizing the oripavine to 14-hydroxymorphinone;
(bb) adding an acid $H^+_n X^{n-}$ to the reaction mixture before, during and/or after the oxidation reaction;
(cc) optionally precipitating the resulting 14-hydroxymorphinone as 14-hydroxymorphinone salt or a solvate thereof;

(dd) optionally isolating the precipitated 14-hydroxymorphinone salt or solvate thereof; and
(ee) performing the process according to any one of (1) to (17).
(23) The process of (18), wherein said process consists of the steps

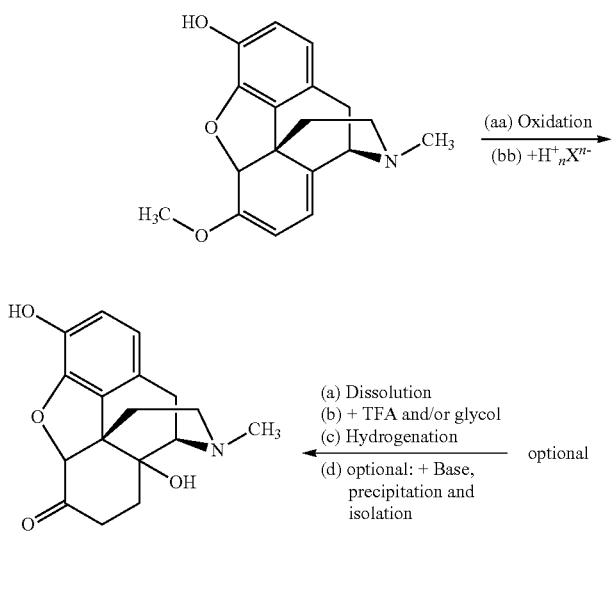

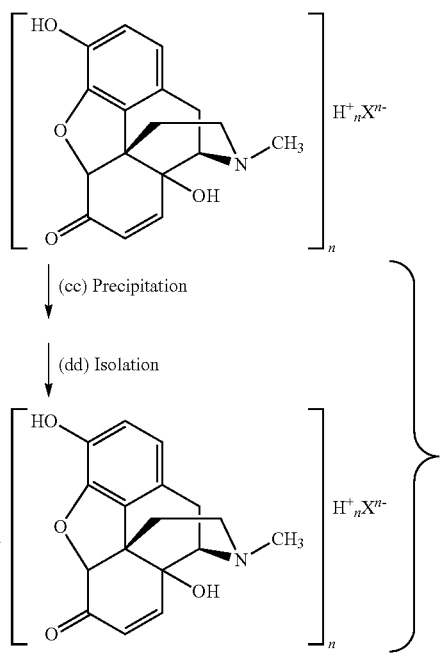

(aa) oxidizing the oripavine to 14-hydroxymorphinone;
(bb) adding an acid $H^+_n X^{n-}$ to the reaction mixture before, during and/or after the oxidation reaction;
(cc) optionally precipitating the resulting 14-hydroxymorphinone as 14-hydroxymorphinone salt or a solvate thereof;
(dd) optionally isolating the precipitated 14-hydroxymorphinone salt or solvate thereof; and
(ee) performing the process according to any one of (1) to (17).
(24) Oxymorphone prepared by the process of any one of (1) to (23).
(25) The oxymorphone of (24), which contains less than 1 ppm 8-hydroxyoxymorphone and less than 1 ppm 14-hydroxymorphinone.
(26) A pharmaceutical composition comprising the oxymorphone according to (24) or (25) and a pharmaceutically acceptable excipient.
(27) The oxymorphone of (24) or (25), or the pharmaceutical composition of (26), for use in the treatment of pain.

Definitions

Unless otherwise specified, the following abbreviations and definitions are used in the context of the present invention.

The undefined article "a" or "an" is intended to mean one or more of the species designated by the term following said article. For example, "a compound of formula II" encompasses one or more molecules of the compound of formula II.

The term "about" in the context of the present application means a value within 15% (±15%) of the value recited immediately after the term "about," including any numeric value within this range, the value equal to the upper limit (i.e., +15%) and the value equal to the lower limit (i.e., −15%) of this range. For example, the phrase "about 100" encompasses any numeric value that is between 85 and 115, including 85 and 115 (with the exception of "about 100%", which always has an upper limit of 100%). In a preferred aspect, "about" means±10%, even more preferably ±5%, even more preferably ±1% or less than ±1%.

"TFA" means trifluoroacetic acid.

An "opioid" in its broadest sense encompasses all compounds usually designated with said term in the art, including opioids which act as an agonist on opioid receptors and opioids which act as an antagonist on opioid receptors. Partial agonists and partial antagonists are also known and are encompassed by the term "opioid". Opioid agonists include, e.g., oxymorphone, oxycodone, noroxymorphone, nalfurafine and salts and solvates of any of the foregoing. Opioid antagonists include, e.g., naltrexone, methylnaltrexone, naloxone, nalmefene, and salts and solvates of any of the foregoing. In the context of the present application, the term "opioid" shall encompass a compound having one of the following scaffolds (which will be designated as "morphine scaffold" in the context of present invention):

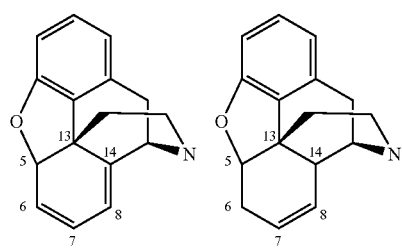

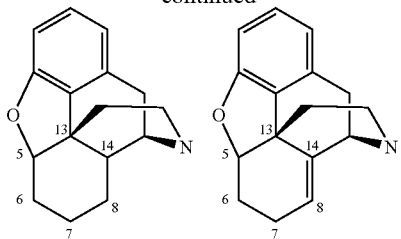

The degree of unsaturation in the ring formed by atoms 5, 6, 7, 8, 14 and 13 may vary (the ring may, e.g., just contain single bonds as in 8-hydroxyoxymorphone, contain just one double bond as in 14-hydroxymorphinone, or contain two double bonds as in oripavine).

The "threshold amount" of 14-hydroxymorphinone in pharmaceutical compositions and dosage forms may be set by regulatory authorities such as the U.S. Food and Drug Administration (FDA) and can then be learned from the latest version of the FDA guidelines ("Guidelines") or, if not addressed in said Guidelines, from the latest version of the ICH Guidelines. In the context of the present invention, the threshold amount may be 10 ppm or less.

The term "8-hydroxy compound" in the context of the present application means a compound containing a hydroxyl group in position 8 of the morphine scaffold. In a narrower sense, it means 8-hydroxyoxymorphone or a salt or solvate thereof. The term "8-hydroxy compound" includes the 8α-hydroxyoxymorphone and/or the 8β-hydroxyoxymorphone.

It should be apparent to a person skilled in the art that the terms "salt" and "solvate" in the present specification encompass "a pharmaceutically acceptable salt" and "a pharmaceutically acceptable solvate", respectively. The formation of a pharmaceutically acceptable salt or solvate may be achieved either directly or by the preparation of a pharmaceutically unacceptable salt or solvate and a subsequent conversion to the pharmaceutically acceptable salt or solvate. A conversion of one pharmaceutically acceptable salt or solvate to another pharmaceutically acceptable salt or solvate is also possible.

The term "solvate" in the context of the present application in its broadest sense means an association product of a compound or salt of the present invention with a solvent molecule. The molar ratio of solvent molecule(s) per compound molecule may vary. The molar ratio of solvent to compound/salt in the solvate may be 1 (e.g., in a monohydrate), more than 1 (e.g., 2, 3, 4, 5 or 6 in a polyhydrate), or less than 1 (e.g., 0.5 in a hemihydrate). The molar ratio need not be an integer ratio, it can also be, e.g., 0.5 (as in a hemihydrate) or 2.5. For example, 1 molecule water per molecule of 14-hydroxymorphinone sulfate is bound in 14-hydroxymorphinone sulfate monohydrate. Applied to oxymorphone, 8-hydroxyoxymorphone, 14-hydroxymorphinone or, where appropriate, to salts thereof, the solvate is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate is a hydrate wherein the ratio of water per molecule is within the range of from 1 to 8. In certain embodiments, the solvate is a hydrate wherein the ratio of water per molecule is within the range of from 1 to 6, i.e. a mono- to hexahydrate. In certain embodiments, it is a monohydrate or a pentahydrate.

The terms "precipitating"/"precipitate"/"precipitation" in the context of the present application shall encompass "crystallizing"/"crystallize"/"crystallization" unless stated otherwise. In certain embodiments, the precipitate described herein is amorphous. In certain embodiments, the precipitate is a mixture of amorphous and crystalline components. In certain embodiments, the precipitate described herein is crystalline. For example, 14-hydroxymorphinone sulfate may precipitate in a crystalline form, whilst oxymorphone base typically is an amorphous precipitate.

The acronym "ppm" means parts per million. For purposes of the present application, the numeric ppm amount values of opioids contained in a composition containing more than one opioid are given in relation to the amount of the opioid ("reference opioid") constituting the majority of the opioids contained in said composition. Such reference opioid will typically be oxymorphone (in the final product oxymorphone of the hydrogenation reaction) or 14-hydroxymorphinone (in the starting material 14-hydroxymorphinone salt of the hydrogenation reaction). The ppm values can be determined by performing a chromatographic resolution of the composition and subsequent calculation of the relative or absolute amounts of the opioid components based on the peak area. For purposes of the present invention, an HPLC method (e.g., as described in Example 11 for oxymorphone and its precursors and by-products) can be performed. The composition components can be detected at a certain wavelength (e.g., at 292 nm for oxymorphone and its precursors and by-products). The HPLC peak area ratio of a certain opioid component to the reference opioid determines the ppm value. The numeric ppm amount value of the one opioid compound constituting the majority of the opioids in the composition (i.e. of the reference opioid, which may be oxymorphone or 14-hydroxymorphinone) can be obtained from the percent area of the peak of this compound in relation to the area sum of all opioid peaks.

Under the HPLC conditions used in the context of the present invention (e.g., the HPLC conditions as described in Example 11 for oxymorphone and its precursors and by-products; or any other reverse phase HPLC conditions), any salt will not be determined in its salt form, but in a dissociated form. For example, the 14-hydroxymorphinone moiety of 14-hydroxymorphinone sulfate will be detected and quantified in its dissolved form, i.e. as 14-hydroxymorphinone. Consequently, the HPLC peak area detectable for an opioid salt of the present invention will be the HPLC peak area which is detected for the opioid moiety comprised in said salt. In case a salt contains more than one opioid moieties per anion, the HPLC method does not detect the absolute/relative amount of the salt itself, but of its opioid moiety. If in such a salt two opioid moieties per anion are present (such as in 14-hydroxymorphinone sulfate wherein n is 2), the peak area detected in the HPLC is due to the presence of the two opioid moieties contained in said salt. In case of a 14-hydroxymorphinone salt wherein n is 3, the peak area detected in the HPLC is due to the presence of the three opioid moieties contained in said 14-hydroxymorphinone salt.

This has the following consequence: As defined above, the numeric ppm value for an opioid is the ratio of peak area for said opioid in relation to the peak area of the reference opioid. In case the present application refers to numeric ppm values for a ratio of 8-hydroxyoxymorphone to a 14-hydroxymorphinone salt, in fact the ratio of the peak area for the 8-hydroxymorphone to the peak area of the 14-hydroxymorphinone (which is contained in the 14-hydroxymorphinone salt) is provided. A 14-hydroxymorphinone salt comprises n-times the structural unit of 14-hydroxymorphinone (e.g., two times for a sulfate salt, three times for a phosphate salt, etc.). All ppm values given in the description are based on the original peak area ratio of the opioid moiety, without adjusting them by dividing them by n. For example, if a peak area ratio of 4 ppm is determined via HPLC for a 14-hydroxymorphinone salt wherein n is 2, the corresponding ppm value will also be 4 (and not 2). This way of giving compound ratios in ppm will be designated as "HPLC peak area ratio" in the following.

The opioid peaks which are typically considered in this determination method are peaks having an UV-Vis spectrum which is typical for an opioid. For 14-hydroxymorphinone sulfate (or another 14-hydroxymorphinone salt or solvate thereof) and for oxymorphone, typically the peaks of oxymorphone N-oxide, pseudo-oxymorphone (i.e., 2,2'-bisoxymorphone), 14-hydroxymorphine, 14-hydroxyisomorphine, 10-ketooxymorphone, 14-hydroxymorphinone N-oxide, 10-hydroxyoxymorphone, 8-hydroxyoxymorphone, 14-hydroxymorphinone, hydromorphone, oxymorphone, 6α-oxymorphol, 6β-oxymorphol, oripavine, 8,14-dihydrooripavine, oxycodone (see, e.g., Example 11) may be considered (if present). However, not all of these peaks have to be considered. It is usually sufficient to consider just some of them, for example 8-hydroxyoxymorphone, 14-hydroxymorphinone, oxymorphone, 6α-oxymorphol, and oripavine.

A reverse phase HPLC method may be used for determination of ppm values.

The detection of the sample components may be performed using a UV/VIS detector, e.g., at a wavelength of 292 nm.

Alternatively, the detection of the sample components may be performed using a mass spectrometer. The amount of a certain component may be determined by using a tritiated internal standard. However, this method of detection does not require the "HPLC peak area ratio" described above, as it uses an internal standard.

In the preferred embodiments, a HPLC method described in Example 11 is used for determination of ppm values. In one embodiment, the HPLC method of Example 11B is used.

"No detectable amount", "not detectable", "not in detectable amounts" or a similar formulation means an amount of the compound in question (e.g. 14-hydroxymorphinone or 8-hydroxyoxymorphone) below the LOD (limit of detection). In the context of the present invention, this means an amount of less than 5 ppm, preferably less than 3 ppm, more preferably less than 1 ppm of the compound in question (e.g. 14-hydroxymorphinone or 8-hydroxyoxymorphone in relation to oxymorphone) (HPLC peak area ratio). In a specific aspect of the invention, this mean the absence (i.e. 0 ppm) of the compound in question.

The term "API" in the context of the present invention means "active pharmaceutical ingredient" (e.g., oxymorphone hydrochloride) and shall be used in its broadest sense as a synonym for a pharmaceutically active compound in the context of the present invention. When an API is used in preparing a pharmaceutical composition or dosage form, the API is the pharmaceutically active component of said pharmaceutical composition or dosage form. Pharmaceutical compositions or dosage forms containing an API may be approved by a governmental agency for sale and use in a patient (e.g., a human). Examples of APIs described in the context of the present invention include oxymorphone and oxymorphone hydrochloride.

The term "pharmaceutical composition" in the context of the present application means a composition which contains an API and is suitable for use in a patient (e.g., a human). It may be approved by a governmental agency for sale and use in a patient. Examples for pharmaceutical compositions described in the context of the present invention are among the compositions containing oxymorphone or oxymorphone hydrochloride. Pharmaceutical compositions may be compositions prepared according to the invention if they comply with regulatory requirements for pharmaceutical compositions containing the same API.

The term "salt" in the context of the present application means a compound comprising at least one cation (e.g., one or two 14-hydroxymorphinone cations resulting from protonation of 14-hydroxymorphinone (free base) by a Bronsted acid (like sulfuric acid)) and at least one anion (e.g., a sulfate anion). A salt may be the result of the neutralization reaction between an acid and a base (e.g., a Bronsted acid and a Bronsted base, or a Lewis acid and a Lewis base). In its solid form, the salt may have a crystalline structure. The term "salt" as used in the present application includes anhydrous, solvated, or hydrated forms of the salt. Whenever a solution or mixture containing a salt is mentioned, the term "salt" shall also encompass the dissolved form of the salt. The term also encompasses pharmaceutically acceptable salts, in particular when it refers to a salt of a compound which can serve as API. In the context of present invention, whenever a 14-hydroxymorphinone salt is mentioned, this refers to a salt containing a 14-hydroxymorphinone cation, resulting, e.g., from protonation of the 14-hydroxymorphinone. The same applies to other salts containing a cation with a morphine scaffold, e.g., a salt of 8-hydroxyoxymorphone. An example for a 14-hydroxymorphinone salt is a salt which consists of two molecules of 14-hydroxymorphinone and one molecule of $H_2SO_4$, i.e. which comprises two 14-hydroxymorphinone cations per sulfate anion (14-hydroxymorphinone sulfate). In this salt, the cation results from the protonation of two molecules of 14-hydroxymorphinone and the anion is the resulting sulfate. In preferred embodiments of the present invention, a salt which is a 14-hydroxymorphinone salt is in its solid form. Another example for a salt is a salt of oxymorphone or a solvate thereof. An example for such salt of oxymorphone is a salt which consists of two molecules of oxymorphone and one molecule of $H_2SO_4$, i.e. which comprises two oxymorphone cations per sulfate anion (oxymorphone sulfate). In this salt, the cation results from the protonation of two molecules of oxymorphone and the anion is the resulting sulfate. In preferred embodiments of the present invention, a salt of oxymorphone is in its solid form.

Whenever a compound or formula mentioned herein contains an atom or structural element which could be a stereocenter (e.g., a chiral carbon atom or the morphine scaffold structure), it shall cover all possible stereoisomers, unless indicated otherwise.

For compounds containing the morphine scaffold, the natural stereoconfiguration of the morphine scaffold as shown in the following shall be preferred:

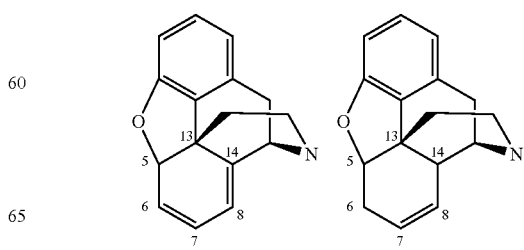

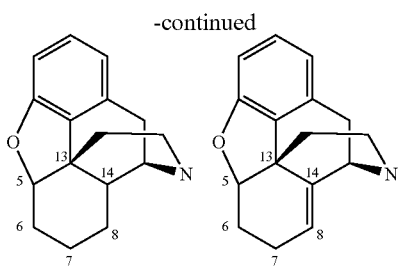

wherein the degree of unsaturation in the ring formed by atoms 5, 6, 7, 8, 14 and 13 may vary (the ring may, e.g., just contain single bonds as in 8-hydroxyoxymorphone, or contain just one double bond as in 14-hydroxymorphinone, or contain two double bonds as in oripavine). At position 5, the following stereoconfiguration is preferred (exemplified for the morphine scaffold of oripavine):

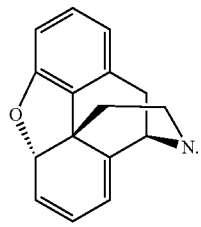

For the 8-hydroxy compounds, an α or a β configuration is possible at position 8 as illustrated in the following:

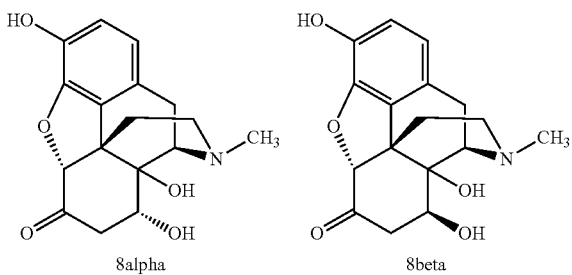 [SMILES: CN1CC[C@]23c4c5ccc(O)c4O[C@H]2C(=O)C[C@@H](O)C3(O)[C@H]1C5 ; CN1CC[C@]23c4c5ccc(O)c4O[C@H]2C(=O)C[C@H](O)C3(O)[C@H]1C5]

8alpha                8beta

In the compounds and compositions of the present invention, either both configurations or only one configuration at position 8 may be present.

For all compounds containing a hydroxyl group at position 14, the following stereoconfiguration occurs at position 14 as exemplified for 14-hydroxymorphinone in the following:

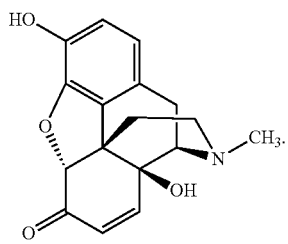 [SMILES: CN1CC[C@]23c4c5ccc(O)c4O[C@H]2C(=O)C=C[C@@]3(O)[C@H]1C5]

DETAILED DESCRIPTION OF THE INVENTION

I. Compounds

Figure 1:
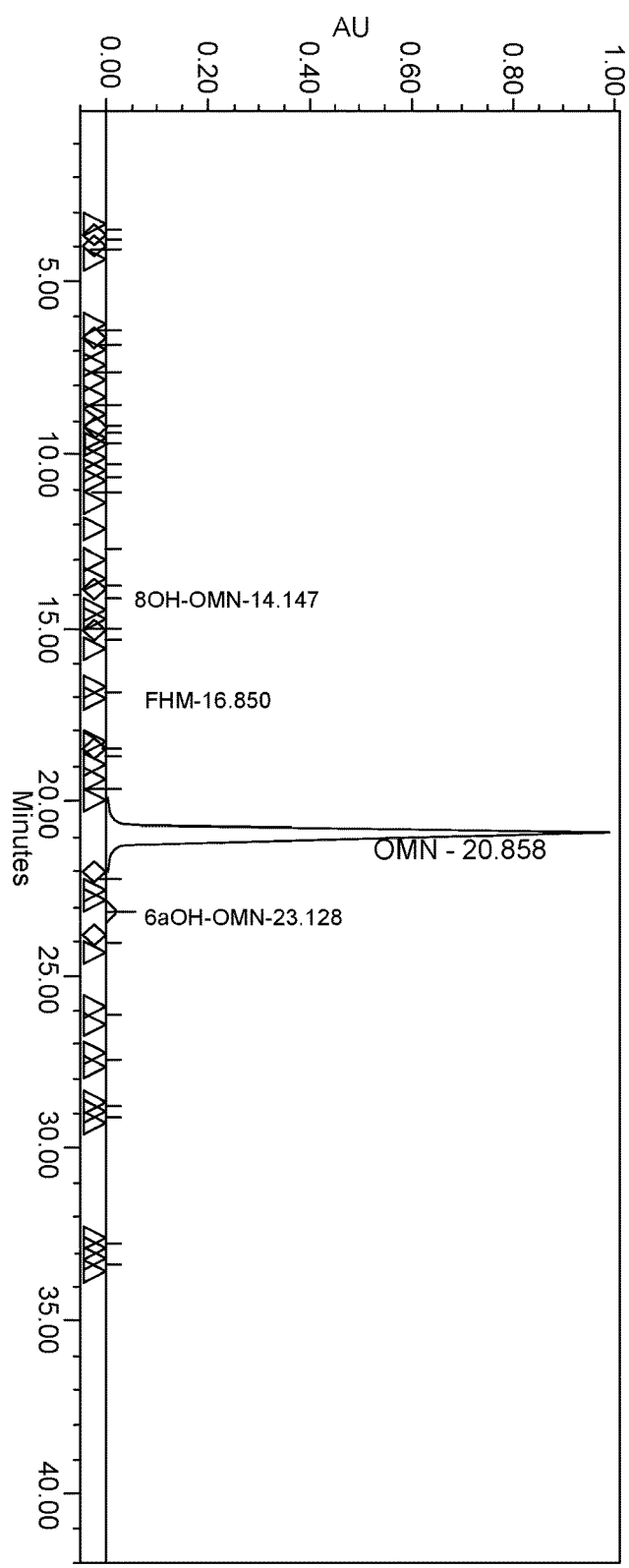
FIG. 1 shows the auto-scaled chromatograph and peak results of the analysis of the precipitated oxymorphone of Comparative Example 1.

In the context of the present invention, compounds which are oripavine, oxymorphone, 14-hydroxymorphinone, 8-hydroxyoxymorphone, and salts and solvates thereof, and mixtures of two or more of any of the foregoing compounds are described. They may be used as starting materials, intermediates or products of the processes according to present invention. To these compounds, the following applies:

In all formulae containing stereocenters, any stereoconfiguration may be present, unless indicated otherwise. If a compound is the product of a process according to the present invention, those stereocenters of the starting material which are not taking part in the reaction will maintain their stereoconfiguration. In certain embodiments, the stereoconfiguration is as described in the Definitions section above.

In all formulae containing $X^{n-}$, $X^{n-}$ may be an inorganic or organic anion wherein n is 1, 2, or 3, preferably is 1 or 2, and more preferably is 2.

$X^{n-}$ may be any anion of a known opioid salt, including, but not limited to, bromide, chloride, iodide, lactate, nitrate, acetate, tartrate, valerate, citrate, salicylate, meconate, barbiturate, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof.

Preferably, $X^{n-}$ is selected from the group consisting of $Cl^-$, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof. More preferably, $X^{n-}$ is $HSO_4^-$, $SO_4^{2-}$, methanesulfonate, tosylate, trifluoroacetate, or a mixture thereof. Even more preferably, $X^{n-}$ is $HSO_4^-$, $SO_4^{2-}$, methanesulfonate or trifluoroacetate. Even more preferably, $X^{n-}$ is $HSO_4^-$, $SO_4^{2-}$, or trifluoroacetate. Even more preferably, $X^{n-}$ is $HSO_4^-$ or $SO_4^{2-}$. Most preferably, $X^{n-}$ is $SO_4^{2-}$.

$X^{n-}$ may be polymer-supported if n is 2 or 3.

Oripavine may be contained in a concentrate of a poppy straw comprising oripavine as a main alkaloid (CPS-O), or it may be purified oripavine, oripavine obtained from a botanical source, synthetic oripavine, semi-synthetic oripavine, oripavine bioengineered by, e.g., bacteria or plant cell cultures, or a combination of two or more of any of the foregoing.

The 14-hydroxymorphinone salt is preferably

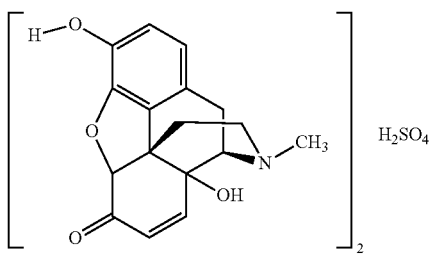

or a solvate (e.g., a hydrate) thereof, respectively. As already mentioned above, this compound will in the context of the present invention be designated as 14-hydroxymorphinone sulfate. Because of its stoichiometric composition, it may also be designated as bis(14-hydroxymorphinone)sulfate. The terms 14-hydroxymorphinone sulfate and bis(14-hydroxymorphinone)sulfate are used interchangeably in the context of the present invention.

When a solvate of a 14-hydroxymorphinone salt is addressed, it may be any association product of a 14-hydroxymorphinone salt with a solvent molecule. The molar ratio of solvent molecule(s) per molecule of 14-hydroxymorphinone salt may vary. The molar ratio of solvent to compound/salt in the solvate may be 1 (e.g., in a monohydrate), more than 1 (e.g., 2, 3, 4, 5 or 6 in a polyhydrate), or less than 1 (e.g., 0.5 in a hemihydrate). The molar ratio need not be an integer ratio, it can also be, e.g., 0.5 (as in a hemihydrate) or 2.5. For example, 1 molecule water per molecule of 14-hydroxymorphinone sulfate is bound in 14-hydroxymorphinone sulfate monohydrate. The solvate of the 14-hydroxymorphinone salt is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate of the 14-hydroxymorphinone salt is a hydrate wherein the ratio of water per molecule is within the range of from 1 to 8. In certain embodiments, the solvate of the 14-hydroxymorphinone salt is a hydrate wherein the ratio of water per molecule is within the range of from 1 to 6, i.e. a mono- to hexahydrate. In certain embodiments, the solvate of the 14-hydroxymorphinone salt is a monohydrate or a pentahydrate. The same applies to other solvates in the context of the present invention, e.g. solvates of oxymorphone or of a salt thereof.

II. Processes for Preparation of Oxymorphone or (Pharmaceutically Acceptable) Salts or Solvates Thereof by Hydrogenation in the Presence of Trifluoroacetic Acid and/or Glycol The present invention provides a process for preparing oxymorphone or an (optionally pharmaceutically acceptable) salt or solvate thereof from a 14-hydroxymorphinone salt or a solvate thereof as represented in the following Scheme 10:

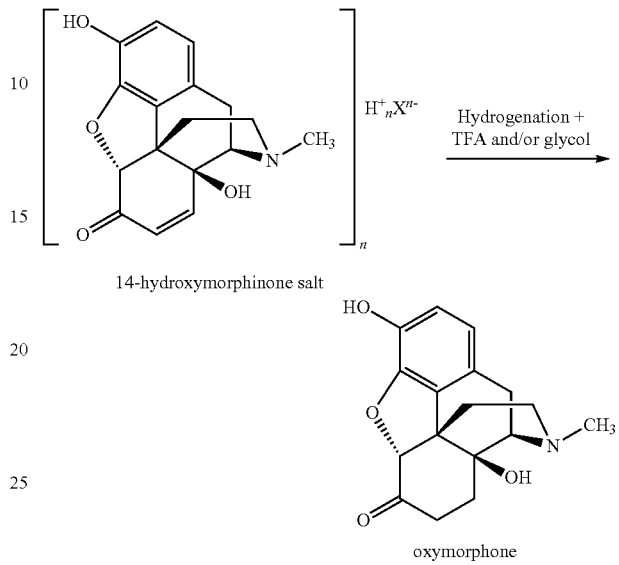

the process comprising or consisting of the steps of (a) providing a solution or suspension of the 14-hydroxymorphinone salt or a solvate thereof;

(b) adding trifluoroacetic acid and/or a glycol, preferably trifluoroacetic acid and a glycol; and (c) hydrogenating the resulting mixture, thus reducing the 14-hydroxymorphinone to the oxymorphone, wherein $X^{n-}$ and n are defined as above.

In certain embodiments, the solution or suspension comprising the 14-hydroxymorphinone salt or the solvate thereof is provided in step (a) by performing steps (a) to (b) of the process described in Section II of PCT/IB2013/001541, steps (a) to (c) of the process described in Section II of PCT/IB2013/001541, or steps (a) to (d) of the process described in Section II of PCT/IB2013/001541 (said steps (a) to (d) of the process described in Section II of PCT/IB2013/001541 correspond to steps (aa) to (dd) described herein below). When steps (a) to (d) described in Section II of PCT/IB2013/001541 are performed, the 14-hydroxymorphinone salt or solvate thereof isolated in step (d) thereof is dissolved or suspended to provide the solution or suspension of said compound in step (a) of the process according to the present invention.

In certain embodiments, the solution or suspension comprising the 14-hydroxymorphinone salt or the solvate thereof is the composition described in Section IV-A of PCT/IB2013/001541.

The hydrogenation of step (c) may be hydrogenation with $H_2$ or transfer hydrogenation. Typically, the hydrogenation is performed in the presence of a hydrogenation catalyst. Preferably, the hydrogenation is performed with $H_2$ and a hydrogenation catalyst.

An exemplary hydrogenation reaction is depicted in Scheme 11:

Scheme 11

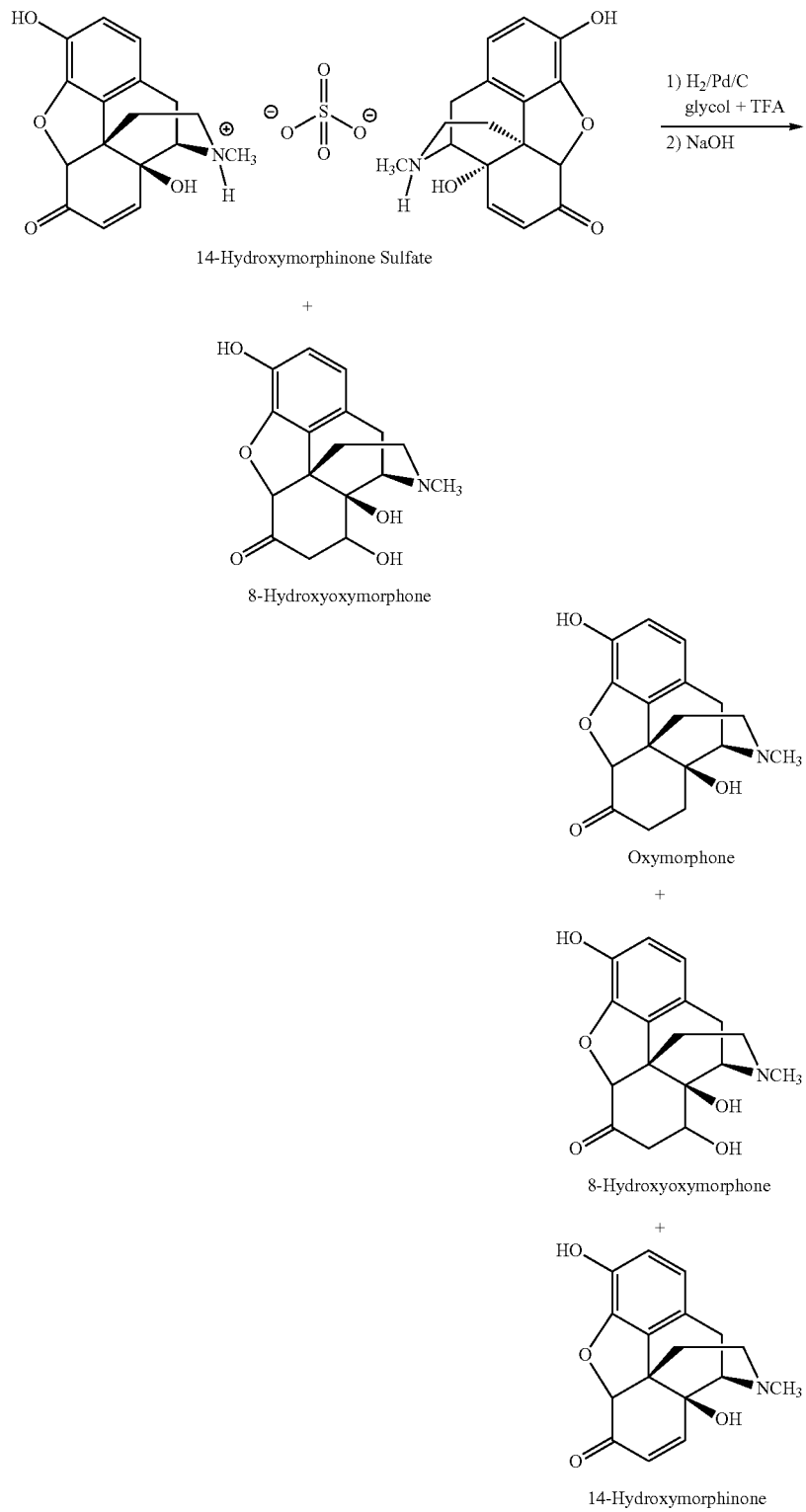

Scheme 11 takes into account that 8-hydroxyoxymorphone or a salt thereof may be present in the starting material in addition to 14-hydroxymorphinone sulfate (or any other 14-hydroxymorphinone salt). Said 8-hydroxy compound may carry over during the hydrogenation reaction. Or, as the hydrogenation is performed under acidic conditions, said 8-hydroxy compound may be converted partially or completely to the corresponding 14-hydroxy compound 14-hydroxymorphinone during the hydrogenation reaction. Thus, 14-hydroxymorphinone and 8-hydroxyoxymorphone may be present in the reaction product which contains oxymorphone as main hydrogenation product. However, typically, neither 8-hydroxyoxymorphone nor 14-hydroxymorphinone are present in the final oxymorphone when the preferred embodiments of the hydrogenation reaction of the present invention are performed.

In the context of the present invention, it is also considered to precipitate and isolate the oxymorphone as its free base. The precipitation and isolation of the free base of the oxymorphone can result in a further purification effect, as the precipitated base may contain less 8-hydroxyoxymorphone and/or 14-hydroxymorphinone than the mother liquor. In particular, 8-hydroxymorphone can be removed by precipitation because its majority remains in the supernatant when oxymorphone is precipitated as its free base.

As the hydrogenation is performed under acidic conditions, the by-products present in the starting material and in the product may be present in their protonated form, or as a salt or solvate thereof.

The amount of TFA added in step (b) may be in the range from 5 to 99 mol % as compared to the molar amount of 14-hydroxymorphinone contained in the starting material. Preferably, TFA is used in a substoichiometric amount, that is, less TFA is added (in mol) than 14-hydroxymorphinone (in mol) which is contained in the starting material. Thus, it is preferred that the amount of TFA added in step (b) is 99 mol % or less (0.99 equivalents or less), more preferably from 10 to 70 mol % (0.1 to 0.7 equivalents), even more preferably from 30 to 50 mol % (0.3 to 0.5 equivalents), even more preferably from 35 to 45 mol % (0.35 to 0.45 equivalents) as compared to the molar amount of 14-hydroxymorphinone contained in the starting material. Thus, the amount of TFA, and the total amount of acid in the reaction mixture is lower than in conventional hydrogenation reactions leading from 14-hydroxymorphinone to oxymorphone, resulting in the advantages described under Summary of the Invention in connection with the substoichiometric amount of TFA.

The amount of glycol added in step (b) is typically in the range from 1 to 8 volumes/weight (vol/w), preferably from 1.5 to 5 vol/w, more preferably from 2 to 3 vol/w, calculated for the glycol volume in mL in relation to the weight in g of 14-hydroxymorphinone salt (for example, in Example 16, 23 g 14-hydroxymorphinone sulfate and 60 mL of propylene glycol are used, resulting in 2.61 vol/w propylene glycol).

Preferably, the glycol is selected from the group consisting of ethylene glycol, propylene glycol, 1,3-propanediol, 1,2-butanediol, 1,3-butanediol, neopentylglycol, and mixtures thereof. More preferably, the glycol is ethylene glycol, propylene glycol, or a mixture thereof.

A combination of TFA with glycol is especially preferred. In said combination, the glycol is preferably selected from the group consisting of ethylene glycol, propylene glycol, 1,3-propanediol, 1,2-butanediol, 1,3-butanediol, neopentylglycol, and mixtures thereof. More preferably, the glycol is ethylene glycol, propylene glycol, or a mixture thereof. In said combination, the volume ratio of TFA to glycol is preferably from 1:15 to 1:45 (vol/vol), more preferably from 1:20 to 1:40 (vol/vol), and even more preferably from 1:25 to 1:35 (vol/vol). A particular embodiment is an embodiment where said ratio is about 1:30 (vol/vol).

The hydrogenation is generally performed at a temperature of from about 25° C. to about 85° C., preferably from about 25° C. to about 60° C., more preferably from about 25° C. to about 50° C., more preferably from about 25° C. to about 45° C., more preferably from about 25° C. to about 40° C., and even more preferably from about 28° C. to about 36° C. (e.g., at 30° C. as in Examples 16 and 17).

Preferably, the hydrogenation is performed with hydrogen gas.

The hydrogenation using hydrogen gas is performed at a suitable pressure. In certain embodiments, the hydrogenation is performed at a pressure of from about ambient pressure (about 14.7 psia, 101.35 kPa) to about 100 psia (689.48 kPa). In certain embodiments, it is performed at a pressure of from about 35 psia (241.32 kPa) to about 80 psia (551.58 kPa), e.g., at about 60 psia (413.69 kPa). In preferred embodiments, it is performed at a pressure of from about 14.7 psia (101.35 kPa) to about 60 psia (413.69 kPa).

The hydrogenation reaction may be run from about 0.5 minute to about 48 hours, from about 1 minute to about 42 hours, from about 2 minutes to about 26 hours, from about 1 minute to about 24 hours, from about 3 minutes to about 22 hours, from about 4 minutes to about 20 hours, from about 5 minutes to about 18 hours, from about 7 minutes to about 16 hours, from about 10 minutes to about 12 hours, from about 12 minutes to about 12 hours, from about 20 minutes to about 12 hours, from about 30 minutes to about 4 hours, from about 2 hours to about 6 hours, or from about 3 hours to about 6 hours. In certain embodiments, the hydrogenation reaction is run from about 1 hour to about 48 hours.

In certain embodiments, the hydrogenation reaction is run for about 10 minutes, about 15 minutes, about 20 minutes, about 25 minutes, about 30 minutes, about 1 hour, about 1.5 hours, about 2 hours, about 2.5 hours, about 3 hours, about 3.5 hours, about 4 hours, about 4.5 hours, about 5 hours, about 5.5 hours, or about 6 hours.

In certain embodiments, the hydrogenation reaction is run for about 8 hours, about 12 hours, about 16 hours, about 20 hours, or about 24 hours.

In certain embodiments, the hydrogenation reaction is run for about 26 hours, about 30 hours, about 34 hours, about 38 hours, about 42 hours, or about 48 hours.

Generally, the hydrogenation reaction is run until completion, i.e. until 14-hydroxymorphinone has disappeared from the reaction mixture. This can be monitored by any suitable detection method, e.g. by the HPLC methods described herein, in particular the HPLC method of Example 11B.

An exemplary non-limiting list of hydrogenation catalysts includes, e.g., Pd/C, palladium-charcoal, a combination of diphenylsilane and Pd/C, Pd(Ph$_3$P)/ZnCl$_2$, a combination of Pd/C with sodium hypophosphite (e.g., in aqueous trifluoroacetic acid), Pt/C, Ru/C, Rh/C, PdO$_2$, PtO$_2$, zinc, magnesium. In certain embodiments, the catalyst is a palladium catalyst. Preferably, the catalyst is Pd/C, in particular Pd/C with 5% Pd.

In certain embodiments, the hydrogenation catalyst is not a metal, e.g., when the hydrogenation is a metal-free transfer hydrogenation as described in Yang, J. W. et al., Angew. Chem. Int. Ed. (2004) 43:6660-6662.

In certain embodiments, a solid support catalyst is used, e.g., to ensure reaction completion upon contact and/or potentially prevent or minimize the formation of any new 14-hydroxymorphinone from 8-hydroxyoxymorphone.

Transfer hydrogenation involves the use of a hydrogen transfer reagent.

Suitable hydrogen transfer reagents include HCO$_2$H, HCO$_2$H/HCO$_2$Na, HCO$_2$H/NEt$_3$, HCHO, H$_2$SO$_4$, HCO$_2$Na/NEt$_3$, H$_2$SO$_4$/NEt$_3$, H$_3$CSO$_2$NHNH$_2$/NEt$_3$, a combination thereof, and the like. Other hydrogen donors, like isopropanol, indoline, cyclohexene, sodium borohydride, tetrahydroquinoline, 2,5-dihydrofuran, phosphoric acid, sodium dithionite, and combinations thereof, might also be useful. In certain embodiments, the hydrogen transfer reagent is a dihydropyridine, e.g., as described in Yang, J. W. et al., Angew. Chem. Int. Ed. (2004) 43:6660-6662.

The hydrogenation may be done by a batch method or in a continuously flowing stream.

In certain embodiments, the hydrogenation is done by a batch method. In an exemplary batch method, a catalyst (e.g., palladium on carbon) is charged into a batch reactor. A solution or suspension of the 14-hydroxymorphinone salt or the solvate thereof is added, or the 14-hydroxymorphinone salt and the solvent are added separately. Trifluoroacetic acid and/or glycol are added. If necessary, water is also added. The batch reactor is then sealed and hydrogenated (e.g., at 14.7 psia (101.35 kPa), and 30° C.) for a time period sufficient to complete hydrogenation (e.g., for 48 hours). The catalyst is then removed by filtration.

The resulting oxymorphone may then be precipitated as its free base by addition of a base, e.g., of sodium hydroxide or ammonium hydroxide. Preferably, sodium hydroxide is used, because the resulting precipitate shows a better behavior in subsequent reactions. The precipitation may be enhanced by adding an antisolvent. The precipitated solids are then optionally washed and dried. The precipitation step (d) is described in more detail below.

In certain embodiments, the hydrogenation reaction is conducted in a continuously flowing stream. A reaction in a continuously flowing stream of the reactants allows for the transport of matter into and out of the reaction mixture as the reaction is taking place. Running the reaction in a continuously flowing stream allows, e.g., better control over reaction conditions (including, e.g., time, temperature, equivalents of reagents, pressure, temperature, time of exposure of reactants to catalysts, pH, etc.), and isolation and/or removal of the oxymorphone from the reaction mixture as it is being formed and/or before any undesired compound is formed. In certain embodiments, the oxymorphone is removed from the reaction mixture as it is being formed.

In certain embodiments, conducting the reaction in a continuously flowing stream allows for conducting the reaction at a temperature which exceeds the boiling point of the solvent, because the pressure can be safely maintained.

In certain embodiments, conducting the reaction in a continuously flowing stream increases the yield of the reaction, increases the volume efficiency of the reaction and/or decreases the number and amounts of by-products formed during the hydrogenation reaction, as the oxymorphone is removed before it reacts with and/or is degraded by the remaining reactants.

The 14-hydroxymorphinone salt or solvate thereof is taken up in a suitable solvent in step (a) of the process according to the present invention. Thus, a suspension or solution of the 14-hydroxymorphinone salt is formed. The hydrogenation product formed during the process typically dissolves in the solvent. In certain embodiments, the solution or suspension of step (a) is provided by using the glycol of step (b) as solvent. In said embodiments, the glycol is either the sole solvent, or it is mixed with other suitable solvents. In particular, it is preferably mixed with water, because water is advantageous if the pH shall be raised after the hydrogenation is complete in order to isolate the oxymorphone as its free base. Preferably, said glycol is selected from the group consisting of ethylene glycol, propylene glycol, 1,3-propanediol, 1,2-butanediol, 1,3-butanediol, neopentylglycol, and mixtures thereof. More preferably, the glycol is ethylene glycol, propylene glycol, or a mixture thereof. Other suitable solvents for the process according to the present invention include or consist of, e.g., methanol, tetrahydrofuran, isopropanol, acetone, ethanol, 1-methoxy-2-propanol, 2-ethoxyethanol, tert-amyl alcohol, isobutanol, 2-methyl-tetrahydrofuran, n-propanol, 1-butanol, 2-butanol, tert-butanol, isopropyl acetate, and di(ethylene glycol) or a mixture of water with any one of the foregoing, or consist of water; preferably, the other suitable solvents include or consist of methanol, tetrahydrofuran, isopropanol, acetone, ethanol, 1-methoxy-2-propanol, 2-ethoxyethanol, tert-amyl alcohol, or a mixture of water with any one of the foregoing, or consist of water.

Water or a mixture of water with any of the foregoing solvents, in particular with the foregoing glycol, is preferred.

In certain embodiments, the suitable solvent is a 20:80 ethylene glycol:water mixture, 30:70 ethylene glycol:water mixture, 40:60 ethylene glycol:water mixture, 50:50 ethylene glycol:water mixture, 60:40 ethylene glycol:water mixture, 70:30 ethylene glycol:water mixture, 80:20 ethylene glycol:water mixture, 90:10 ethylene glycol:water mixture, 100:0 ethylene glycol:water mixture, a 20:80 propylene glycol:water mixture, 30:70 propylene glycol:water mixture, 40:60 propylene glycol:water mixture, 50:50 propylene glycol:water mixture, 60:40 propylene glycol:water mixture, 70:30 propylene glycol:water mixture, 80:20 propylene glycol:water mixture, 90:10 propylene glycol:water mixture, 100:0 propylene glycol:water mixture, a 50:50 methanol:water mixture, 60:40 methanol:water mixture, 70:30 methanol:water mixture, 80:20 methanol:water mixture, 90:10 methanol:water mixture, 100:0 methanol:water mixture, 50:50 ethanol:water mixture, 60:40 ethanol:water mixture, 70:30 ethanol:water mixture, 80:20 ethanol:water mixture, 90:10 ethanol:water mixture, 100:0 ethanol:water mixture, 90:10 tetrahydrofuran:water mixture, 100:0 tetrahydrofuran:water mixture, 90:10 isopropanol:water mixture, 70:30 acetone:water mixture, 80:20 acetone:water, or 90:10 acetone:water mixture. 8-Hydroxyoxymorphone is more soluble in these mixtures than oxymorphone base and therefore may remain in solution while the oxymorphone free base may be precipitated by addition of a base at the end of the hydrogenation.

In certain preferred embodiments, the suitable solvent comprises or consists of a mixture of glycol and water. Preferably, said glycol is selected from the group consisting of ethylene glycol, propylene glycol, 1,3-propanediol, 1,2-butanediol, 1,3-butanediol, neopentylglycol, and mixtures thereof. More preferably, the glycol is ethylene glycol, propylene glycol, or a mixture thereof.

In certain embodiments, the suitable solvent comprises or consists of a mixture of ethylene glycol and water.

In certain embodiments, the suitable solvent comprises or consists of a mixture of propylene glycol and water.

It is preferable to have more water than glycol in the hydrogenation reaction mixture. I.e., a glycol:water mixture containing less than 50 parts glycol per 50 parts of water is preferred. Preferred mixtures are 30:70 glycol:water mixtures, 35:65 glycol:water mixtures, 40:60 glycol:water mixtures, and 45:55 glycol:water mixtures, and ratios between these ratios, The preferred range is from 20:80 to less than 50:50 glycol:water mixtures, more preferably from 30:70 to 45:55 glycol:water mixtures, and more preferably from 35:65 to 45:55 glycol:water mixtures. In particular, mixtures of about 40:60 glycol:water are preferred. Especially preferred are mixtures of from 35:65 to 45:55, preferably about 40:60 ethylene glycol:water, or of from 35:65 to 45:55, preferably about 40:60 propylene glycol:water.

In certain embodiments, the suitable solvent used in step (a) comprises or consists of water and the glycol is added in step (b). In certain other embodiments, both glycol and water are added simultaneously (either separately or as mixture) to the reaction mixture at the beginning of the hydrogenation process; in said embodiments, the solution or suspension of step (a) is provided by using the glycol of step (b) as solvent.

Once the hydrogenation is completed, the oxymorphone may be precipitated as its free base or a salt or solvate thereof.

In certain embodiments, the oxymorphone is precipitated as its salt or a solvate thereof. In said salt, the anion may be trifluoroacetate, or the same $X^{n-}$ as in the starting material 14-hydroxymorphinone salt, or a mixture thereof.

Preferably, the oxymorphone is precipitated as its free base, in particular by step (d):
(d) adding a base, thus raising the pH to a pH where the oxymorphone precipitates, and isolating the oxymorphone as its free base or a solvate thereof.

Said step (d) is combined with steps (a) to (c) in a preferred process according to the present invention, and said preferred process either comprises steps (a) to (d) or consists of steps (a) to (d). Without being bound by theory, it is assumed that the combination of the precipitation and isolation step (d) with the hydrogenation reaction of steps (a) to (c) gives the best results, i.e. results in the lowest amount of 8-hydroxyoxymorphone and 14-hydroxymorphinone in the final oxymorphone base.

The pH where the oxymorphone precipitates can be determined by routine measures. However, it is generally in the range from 8.5 to 9.2, preferably at about 9.0.

The base added in step (d) may be any Bronsted base, provided that its components do not form an insoluble salt with other components of the reaction mixture. The base is preferably selected from the group consisting of NaOH, KOH, $Na_2CO_3$, $K_2CO_3$, $NaHCO_3$, $KHCO_3$, $HCO_2Na$, $CH_3CO_2Na$, $NEt_3$, $NH_4OH$ or any mixtures thereof. More preferably, it is a base containing hydroxide as anion, even more preferably it is an alkali hydroxide or pseudo-alkali hydroxide. Even more preferably, it is ammonium hydroxide or sodium hydroxide, and most preferably it is sodium hydroxide. Sodium hydroxide is preferably used, because the resulting precipitate shows a better behavior in subsequent reactions than the precipitate resulting from ammonium hydroxide. Ammonium hydroxide forms ammonium sulfate or ammonium trifluoroacetate salts that might precipitate with the oxymorphone base. These ammonium salts can interfere, e.g., with the conversion of oxymorphone to naloxone. It is believed that they react with N-demethylation agents. The product resulting from sodium hydroxide has less impact on further conversions of oxymorphone base.

The amount of base added in step (d) has to be sufficient to achieve precipitation of the oxymorphone in its free base form. Thus, it is preferably in the range from 0.5 to 2.0 molar equivalents, more preferably from 0.8 to 1.7 equivalents, even more preferably from 1.1 to 1.4 molar equivalents relative to the oxymorphone base. From 1.2 to 1.3 molar equivalents base are particularly preferred. Preferably, said base is sodium hydroxide.

In certain embodiments, the precipitation of the oxymorphone or salt or solvate thereof is enhanced by one or more of the following:
(i) adjusting (e.g., lowering) the temperature of the reaction mixture to the precipitation temperature;
(ii) addition of an antisolvent;
(iii) addition of a seed crystal;
(iv) changing the ionic strength of the reaction mixture (e.g., by addition of a salt);
(v) concentrating the reaction mixture;
(vi) reducing or stopping agitation of the reaction mixture;
or any other conventional method for initiating or enhancing precipitation or crystallization.

When the temperature is adjusted to the precipitation temperature, this means that the precipitation of the oxymorphone base or salt or solvate thereof is initiated and/or enhanced by adjusting the temperature of the reaction mixture to or beyond a temperature at which said compound precipitates ("precipitation temperature"). The temperature is either adjusted by performing the reaction at the precipitation temperature, or by lowering the temperature of the reaction mixture during the reaction or after completion of the reaction.

In certain embodiments, the reaction mixture is adjusted to a temperature of ≤40° C. to initiate precipitation, i.e. the precipitation temperature is ≤40° C. In certain embodiments, the precipitation is initiated at a precipitation temperature of about −20° C., about −15° C., about −10° C., about −5° C., about 0° C., about 5° C., about 10° C., about 15° C., about 17° C., about 19° C., about 21° C., about 23° C., about 25° C., about 27° C., about 29° C., about 31° C., about 33° C., about 35° C., about 37° C., or about 40° C.

In certain embodiments, the precipitation temperature is in a range of from about −20° C. to about 40° C., preferably from about −10° C. to about 40° C., more preferably from about −5° C. to about 35° C.

In certain embodiments, the precipitation temperature is in a range of from about −10° C. to about 22° C., preferably from about −5° C. to about 10° C., more preferably from about −5° C. to about 5° C.

In certain embodiments, an antisolvent is used in addition to adjusting the temperature to the precipitation temperature. Generally, however, precipitation will also occur without adding an antisolvent.

Precipitation may also be achieved or enhanced by adding an antisolvent to a solution of the oxymorphone or oxymorphone salt, or by preparing a supersaturated solution (e.g. by cooling or concentrating a reaction mixture) from which the resulting oxymorphone or salt or solvate thereof is precipitated, e.g. by cooling beyond the precipitation temperature or by adding a seed crystal. The precipitated solids are then optionally washed and dried. In one aspect, this precipitation may be achieved by adding one or more of acetone, 1-methoxy-2-propanol, 2-butanol, and tert-butyl methyl ether to a reaction mixture. In a specific embodiment, tert-butyl methyl ether is added to a reaction mixture which already may comprise water (which may be the sole solvent in the reaction mixture). In another specific embodiment, 2-butanol is added to a reaction mixture which already may comprise water. In one aspect, this precipitation may be achieved by using a mixture of water and an antisolvent, in particular a mixture of water, or a mixture of water and tert-butyl methyl ether, or a mixture of water, tetrahydrofuran, and tert-butyl methyl ether. Said mixture may replace the reaction solvent after completion of the hydrogenation reaction. The mixture can also be prepared by adding antisolvent after completion of the hydrogenation reaction. 2-Butanol is the most preferred antisolvent.

Further suitable antisolvents may be the antisolvents described in Section IV. I.e., a suitable antisolvent may comprise or consist of tert-butyl methyl ether, diethyl ether, hexane(s), tert-amyl alcohol, methanol, ethanol, n-propanol, isopropanol, 1-butanol, 2-butanol, tert-butanol, isobutanol, heptanes, xylenes, toluene, acetone, 2-butanone, ethyl acetate, isopropyl acetate, tetrahydrofuran, 2-methyl-tetrahydrofuran, 1,2-dichloroethane, chloroform, dichloromethane, 1-methoxy-2-propanol, 2-ethoxyethanol, 1,4-dioxane, methyl formate, methyl acetate, or a mixture of two or more of any of the foregoing. The listed alcohols and ethers are the preferred antisolvents, the alcohols being even more preferred. In some preferred embodiments, the antisolvent is isopropanol or 2-butanol. The most preferred antisolvent is 2-butanol.

The resulting precipitate may then be isolated, thus removing it from the mother liquor and advantageously further purifying the free base from 8-hydroxyoxymorphone and/or 14-hydroxymorphinone which remains in the mother liquor.

Preferably, the oxymorphone is isolated as its free base. The resulting oxymorphone in its form as free base comprises lower amounts of 8-hydroxyoxymorphone and/or 14-hydroxymorphinone (or salt or solvate thereof) as compared to oxymorphone made by a process which does not involve the hydrogenation according to the present invention.

Oxymorphone and compositions comprising said oxymorphone which can be prepared via the process of present invention are described, e.g., in Section VI below. The amounts of 8-hydroxyoxymorphone and 14-hydroxymorphinone which may be present in the compositions comprising the oxymorphone are described in Section VI below. In certain embodiments, this oxymorphone or these compositions comprising the oxymorphone are the product of the process described in the present section or in the subsequent Section III.

In certain embodiments, the compositions comprising the oxymorphone which are the product of the process described in the present section or in the subsequent Section III can be used as pharmaceutical compositions without further processing or purification steps, in particular without further hydrogenation steps.

In certain embodiments of this process, the 14-hydroxymorphinone salt is 14-hydroxymorphinone sulfate or a solvate thereof.

In certain embodiments of this process, the 14-hydroxymorphinone salt is 14-hydroxymorphinone trifluoroacetate or a solvate thereof.

III. Processes for Preparing Oxymorphone Starting from Oripavine

Present invention further provides a process for preparing oxymorphone from oripavine via a 14-hydroxymorphinone salt or a solvate thereof. In this process, the 14-hydroxymorphinone salt or solvate thereof serves as an intermediate. Said intermediate 14-hydroxymorphinone salt or the solvate thereof may either be isolated or converted to oxymorphone or a salt or solvate thereof without further isolation. In certain preferred embodiments, said intermediate 14-hydroxymorphinone salt or the solvate thereof is isolated before its conversion to the oxymorphone or a salt or solvate thereof.

Thus, present invention provides a process for preparing oxymorphone or a salt or solvate thereof from oripavine or a salt or solvate thereof, the process comprising or consisting of (Scheme 12):

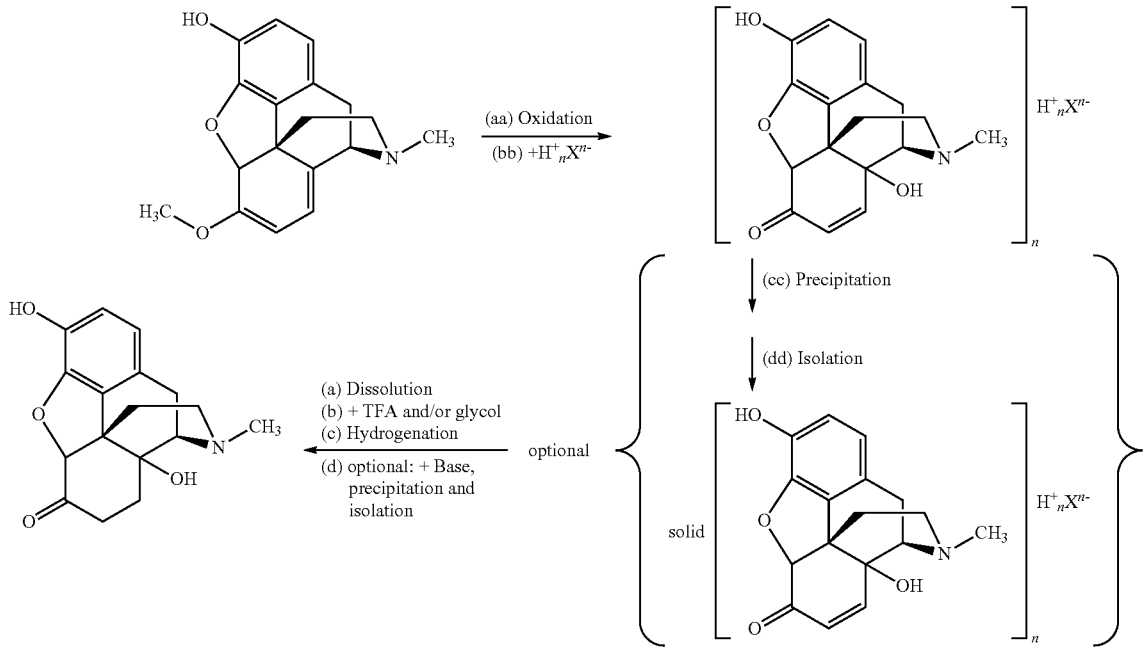

(aa) oxidizing the oripavine to 14-hydroxymorphinone;
(bb) adding an acid $H^+_n X^{n-}$ to the reaction mixture before, during and/or after the oxidation reaction;
(cc) optionally precipitating the resulting 14-hydroxymorphinone as 14-hydroxymorphinone salt or a solvate thereof;
(dd) optionally isolating the precipitated 14-hydroxymorphinone salt or solvate thereof;
(a) providing a solution or suspension of the 14-hydroxymorphinone salt or a solvate thereof;
(b) adding trifluoroacetic acid and/or a glycol, preferably trifluoroacetic acid and a glycol; and
(c) hydrogenating the resulting mixture, thus reducing the 14-hydroxymorphinone to oxymorphone,
wherein $X^{n-}$ and n are defined as above.

In certain embodiments, the 14-hydroxymorphinone salt or solvate thereof is precipitated and/or isolated in steps (cc) and/or (dd) before the hydrogenation via steps (a) to (c).

In certain embodiments, said process will contain a further step, namely (d) adding a base, thus raising the pH to a pH where the oxymorphone precipitates, and isolating the oxymorphone as its free base or a solvate thereof. See above, Section II.

In certain embodiments, step (c) of the process results in a pharmaceutically acceptable salt or solvate of the oxymorphone. In certain embodiments, step (c) of the process results not only in such pharmaceutically acceptable salt or solvate of the oxymorphone, but the complete resulting composition can be used as pharmaceutical composition without requiring further processing (e.g., purification). In particular, it may be used without an additional hydrogenation to remove by-products, e.g., 14-hydroxymorphinone. For example, the process may result in an oxymorphone salt composition which is suitable for incorporation into a dosage form, the oxymorphone salt composition being directly prepared from the hydrogenation product of step (c) by a conversion which does not include a further/additional hydrogenation step.

In certain embodiments, the salt or solvate of oxymorphone which results from step (c) is not a pharmaceutically acceptable salt or solvate.

In certain embodiments, the oxymorphone or salt or solvate thereof resulting from step (c) may be converted into a pharmaceutically acceptable salt or solvate thereof in an additional step at the end of the process. Methods for such conversion are known in the art (e.g., anion exchange).

In certain embodiments, the 14-hydroxymorphinone salt or solvate thereof which is an intermediate of the process will have the properties as described in Section IV of PCT/IB2013/001541.

All elements of steps (a) to (d) of said process and the embodiments of said elements have already been described above. All elements of steps (aa) to (dd) of said process and the embodiments of said elements have already been described in PCT/IB2013/001541 (as steps (a) to (d) in Section II of PCT/IB2013/001541). Oxymorphone which can be prepared via the process, and the amounts of 8-hydroxyoxymorphone and 14-hydroxymorphinone which may be present in compositions comprising said oxymorphone are described in Section VI below. In certain embodiments, these compounds are the product of the process described in the present section.

In the following, an exemplary embodiment of said process will be described. Therein the starting compound for the oxidation reaction is oripavine or a salt or solvate thereof, the oxidation agent comprises or is performic acid formed in situ from hydrogen peroxide and formic acid, the acid $H^+_nX^{n-}$ in step (bb) is sulfuric acid which is added to the reaction mixture, the 14-hydroxymorphinone salt is 14-hydroxymorphinone sulfate or a solvate thereof, and the product is oxymorphone or a salt or solvate thereof.

In a preferred embodiment, the oxymorphone is precipitated and isolated as its free base.

IV. Processes for Preparing a 14-Hydroxymorphinone Salt

A 14-hydroxymorphinone salt, the starting material for the process according to the present invention, can be prepared according to the processes for preparing a compound of formula V described in Section II of PCT/IB2013/001541. The contents of this Section II of PCT/IB2013/001541 are explicitly incorporated herein by reference.

Hence, in certain embodiments, the 14-hydroxymorphinone salt or a solvate thereof

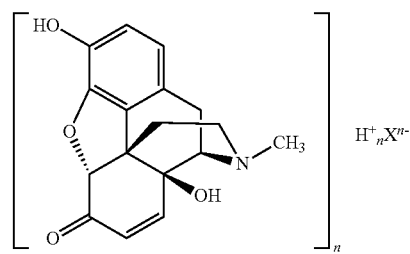

can be prepared from oripavine or a salt or solvate thereof, the process comprising:

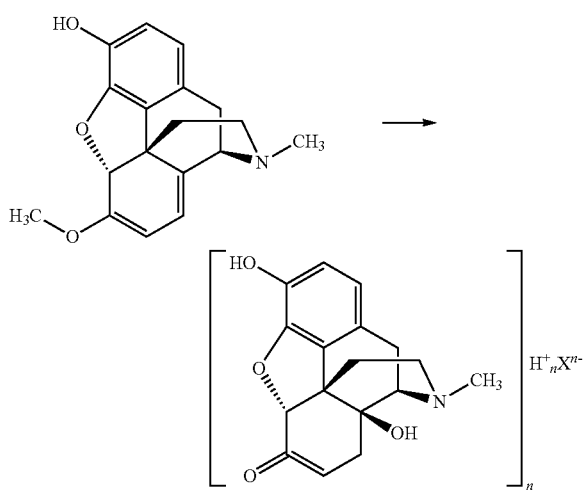

(aa) oxidizing the oripavine to 14-hydroxymorphinone; and
(bb) adding an acid $H^+_nX^{n-}$ to the reaction mixture before, during and/or after the oxidation reaction, wherein
$X^{n-}$ and n are defined as above.

In a preferred embodiment, the acid $H^+_nX^{n-}$ is added to the reaction mixture before or during the oxidation reaction. More preferably, the acid $H^+_nX^{n-}$ is present in the reaction mixture during the complete oxidation reaction, i.e. it is added before the start of the oxidation reaction, or at the start of the oxidation reaction.

In addition to the 14-hydroxymorphinone salt, the oxidation of oripavine may generate 8-hydroxyoxymorphone or a salt or solvate thereof. The 8-hydroxyoxymorphone may be formed as follows:

Scheme 3

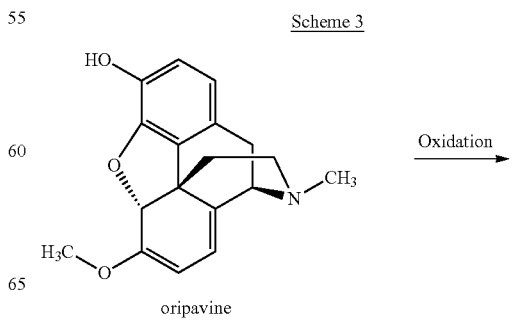

oripavine

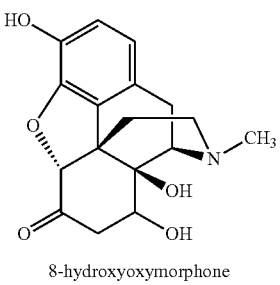

8-hydroxyoxymorphone

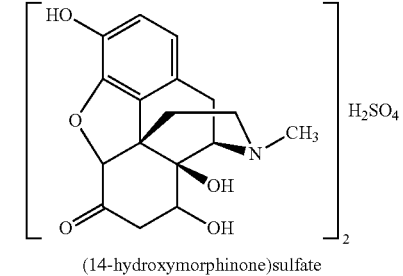

(14-hydroxymorphinone)sulfate

The use of the 14-hydroxymorphinone salt or solvate thereof as starting material in the hydrogenation process of the present invention can reduce the amount of the 8-hydroxyoxymorphone which is present at the beginning of the hydrogenation, as compared to a process for preparation of oxymorphone without involving the 14-hydroxymorphinone salt.

The formation of a 14-hydroxymorphinone salt and the isolation of the precipitated salt appear to prevent or reduce (i) the formation of 8-hydroxyoxymorphone during oxidation of oripavine, as compared to processes which do not involve the formation of the 14-hydroxymorphinone salt, (ii) the presence of 8-hydroxyoxymorphone in a composition comprising oxymorphone base made via a 14-hydroxymorphinone salt, and (iii) the presence of 8-hydroxyoxymorphone or a salt thereof and 14-hydroxymorphinone or a salt thereof in an oxymorphone salt or in a pharmaceutical composition comprising an oxymorphone salt made via a 14-hydroxymorphinone salt.

Pharmaceutical compositions prepared by processes of the present invention may be quantitatively different from pharmaceutical compositions prepared by conventional processes which do not utilize the hydrogenation reaction conditions of the present invention, and may offer advantages over the compositions prepared by conventional processes, e.g., in terms of safety, efficiency and reduced manufacturing costs. For example, these compositions may contain less by-products and/or require less or no further processing steps after synthesis of their API.

An exemplary embodiment of a process for preparing a 14-hydroxymorphinone salt is a process for preparing 14-hydroxymorphinone as its sulfate salt (or a solvate thereof), which encompasses the oxidation of oripavine illustrated in Scheme 13:

Scheme 13

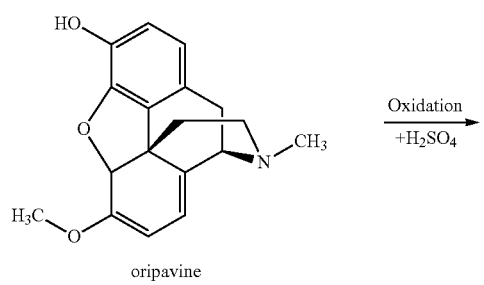

oripavine

In a preferred embodiment of the present invention, the 14-hydroxymorphinone salt is

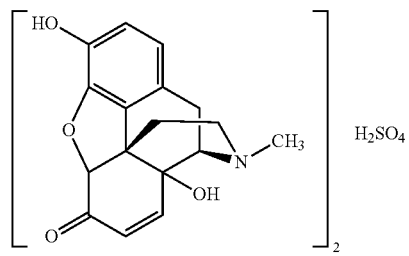

(14-hydroxymorphinone sulfate) or a solvate thereof.

As described above, 8-hydroxyoxymorphone may be converted to 14-hydroxymorphinone during further processing of the 14-hydroxymorphinone salt to oxymorphone or a salt or solvate thereof. If less 8-hydroxyoxymorphone is formed during the oxidation reaction, less 8-hydroxyoxymorphone and ultimately less 14-hydroxymorphinone may finally be present in oxymorphone or an (optionally pharmaceutically acceptable) salt or solvate thereof (e.g., oxymorphone hydrochloride) made via or from the 14-hydroxymorphinone salt or a solvate thereof, as compared to oxymorphone or a salt or solvate thereof made via a different intermediate. Less 8-hydroxyoxymorphone and ultimately less 14-hydroxymorphinone may then also finally be present in a pharmaceutical composition or dosage form containing said oxymorphone or a pharmaceutically acceptable salt or solvate thereof. Ultimately, the use of the 14-hydroxymorphinone salt as starting material for the hydrogenation process of the present invention may therefore contribute to the result that the amount of 8-hydroxyoxymorphone and 14-hydroxymorphinone formed during preparation of oxymorphone or salt or solvate thereof is insufficient to increase the total amount of the 14-hydroxymorphinone in said oxymorphone above an undesired level, e.g., above a desired threshold amount of 14-hydroxymorphinone.

In certain embodiments, the oxidation step (aa) is partially or completely performed in the presence of the acid $H^+_n X^{n-}$ in the reaction mixture. That is, the acid $H^+_n X^{n-}$ is added before or during the oxidation reaction, preferably before the oxidation reaction. The acid $H^+_n X^{n-}$ is preferably present in the reaction mixture during the complete oxidation reaction, i.e. it is added before the start of the oxidation reaction, or at the start of the oxidation reaction.

The 14-hydroxymorphinone salt may precipitate in certain embodiments of the oxidation reaction.

The formation of the 14-hydroxymorphinone salt or solvate thereof may occur via a salt formed from the oripavine, via 14-hydroxymorphinone in its free base form or in its salt or solvate form, via both of said routes, or via a combination of one or both of said routes with other reaction routes known to a person skilled in the art. During this reaction, at least a part or all of the oripavine and/or 14-hydroxymorphinone are protonated. This may happen, e.g., under acidic reaction conditions.

In certain embodiments of the oxidation reaction, the formation of the 14-hydroxymorphinone salt or a solvate thereof in this process allows for a more volume efficient oxidation of the oripavine in comparison to a process wherein no 14-hydroxymorphinone salt is formed.

In certain embodiments of the oxidation reaction, the formation of the 14-hydroxymorphinone salt results in a lower ratio of 8-hydroxyoxymorphone to the 14-hydroxymorphinone in the product, as compared to a process wherein no 14-hydroxymorphinone salt or solvate thereof is formed.

In certain embodiments of the oxidation reaction, said result may be achieved because the formation of the 14-hydroxymorphinone salt or a solvate thereof has the effect that less 8-hydroxy compound is formed during the oxidation reaction in comparison to an oxidation reaction where no 14-hydroxymorphinone salt or solvate thereof is formed. In other words, the formation of the 14-hydroxymorphinone salt allows for an improvement of the by-product profile of the reaction product.

In these embodiments, the oxidation reaction is typically completely or partially performed in the presence of the acid $H^+{}_nX^{n-}$.

One example for such embodiment may be the formation of a 14-hydroxymorphinone salt, wherein n is 2 and preferably wherein $X^{n-}$ is sulfate. Another example for such embodiment may be the formation of a 14-hydroxymorphinone salt, wherein n is 1 and preferably wherein $X^{n-}$ is trifluoroacetate. Another example for such embodiment may be the formation of a 14-hydroxymorphinone salt, wherein n is 3 and preferably wherein $X^{n-}$ is phosphate.

In certain embodiments of the oxidation reaction said result may be achieved because the formation of the 14-hydroxymorphinone salt or a solvate thereof has the effect that 8-hydroxyoxymorphone can be separated from the 14-hydroxymorphinone salt or the solvate thereof, e.g., by precipitation of the 14-hydroxymorphinone salt or the solvate thereof from the reaction mixture. One example for such an embodiment may be the formation of a 14-hydroxymorphinone salt wherein $X^n$ is sulfate.

In certain embodiments a combination of these effects takes place, i.e., said result is achieved because both less 8-hydroxyoxymorphone is formed during the oxidation and because said compound can be separated from the 14-hydroxymorphinone salt or solvate thereof. One example for such an embodiment may be the formation of a 14-hydroxymorphinone salt wherein $X^{n-}$ is sulfate.

Preferably, the formation of the 14-hydroxymorphinone salt or a solvate thereof reduces the formation of 8-hydroxy compounds during the oxidation reaction and/or the presence of 8-hydroxy compounds in the oxidation product, as compared to an oxidation reaction which does not involve the step of forming the 14-hydroxymorphinone salt or a solvate thereof. The presence of 8-hydroxyoxymorphone in the product may be reduced by precipitation of the 14-hydroxymorphinone salt. This may reduce the formation of 14-hydroxymorphinone during subsequent reactions (e.g., during conversion of oxymorphone made from a 14-hydroxymorphinone salt to oxymorphone hydrochloride), as compared to reactions which do not involve the step of forming the 14-hydroxymorphinone salt or a solvate thereof.

The process for preparing the 14-hydroxymorphinone salt or a solvate thereof may be performed by oxidizing oripavine with an oxidizing agent in the presence of one or more acids such that the 14-hydroxymorphinone salt is formed. An 8-hydroxy compound or a salt or solvate thereof may be formed as by-product during the oxidation. At the end of the preparation of the 14-hydroxymorphinone salt or a solvate thereof, said 14-hydroxymorphinone salt or solvate thereof may be provided as a solid, a solution, or a suspension. The 14-hydroxymorphinone salt or a solvate thereof is the starting material or intermediate for the hydrogenation process of the present invention, i.e., the process for preparing oxymorphone or an (optionally pharmaceutically acceptable) salt or solvate thereof. The 14-hydroxymorphinone salt and the solvate thereof will be described in more detail below. However, the subsequent description of the oxidation process shall also apply to the 14-hydroxymorphinone salt and the solvate thereof per se where applicable (e.g., when the 14-hydroxymorphinone salt is described as a reaction product of such oxidation process).

The process step for preparing said 14-hydroxymorphinone salt is depicted in the following Scheme 14:

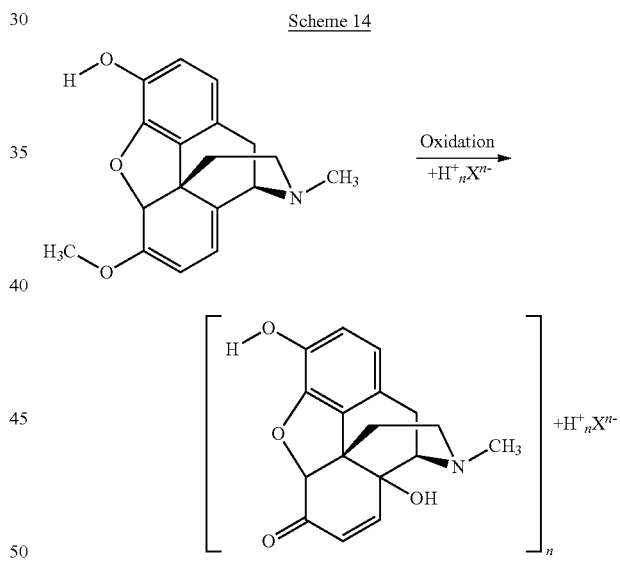

Scheme 14

In certain embodiments of this process, the acid $H^+{}_nX^{n-}$ is sulfuric acid.

The process for preparing a 14-hydroxymorphinone salt may be performed as one-pot-reaction, wherein steps (aa) and (bb) are performed concomitantly. In said one-pot-reaction, at least a part of the acid $H^+{}_nX^{n-}$ is typically added before the oxidizing agent, or concomitantly with the oxidizing agent. In certain embodiments, all of the acid $H^+{}_nX^{n-}$ is added before the oxidizing agent, or concomitantly with the oxidizing agent.

An exemplary one-pot reaction for forming a 14-hydroxymorphinone salt, namely 14-hydroxymorphinone sulfate, is depicted in Scheme 15:

Scheme 15

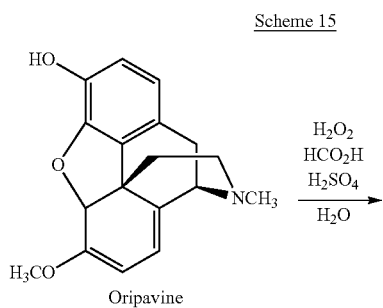

Oripavine

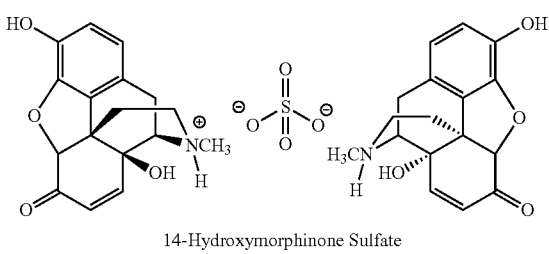

14-Hydroxymorphinone Sulfate

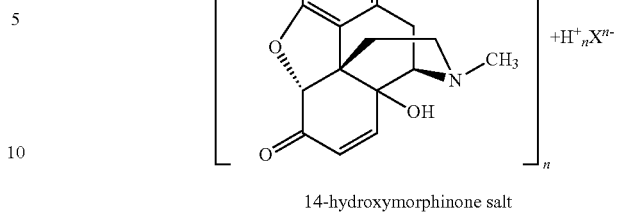

14-hydroxymorphinone salt

In the oxidation reaction depicted in this Scheme, a peracid formed from hydrogen peroxide and formic acid is used as at least one oxidizing agent, and sulfuric acid is used as the acid $H^+{}_nX^{n-}$. It should be noted that it is not excluded that at least part of the sulfuric acid also forms a peracid in the presence of the hydrogen peroxide, which peroxide may also take part in the oxidation reaction.

The reaction conditions of steps (aa) and (bb) (e.g., time, temperature, pH, relative proportions of the reagents) will be described in detail in the following. In a typical embodiment of the present invention, they are adjusted such that the resulting product containing the 14-hydroxymorphinone salt is free from, or contains about 2500 ppm or less, about 2000 ppm or less, about 1500 ppm or less, about 1000 ppm or less, about 500 ppm or less, or about 100 ppm or less of 8-hydroxyoxymorphone.

Oxidation Reaction

The oxidation reaction of step (aa) of the process is represented in Scheme 16 and results in the formation of 14-hydroxymorphinone, which in turn is part of the 14-hydroxymorphinone salt:

Scheme 16

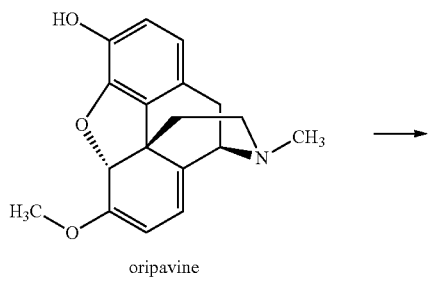

oripavine

The oxidation reaction of step (aa) is generally run until at least about 90%, about 92%, about 95%, about 97%, about 98%, about 99% or about 100% of the oripavine is consumed by the reaction. The amount of said compound remaining in the reaction may be determined by any conventional determination method, e.g., by HPLC, for example the HPLC method described in Example 11A.

The oxidizing reaction time can be anywhere from about 1 minute to about 36 hours, from about 10 minutes to about 34 hours, from about 20 minutes to about 32 hours, from about 30 minutes to about 30 hours, from about 45 minutes to about 28 hours, from about 1 hour to about 24 hours, from about 3 hours to about 21 hours, from about 5 hours to about 18 hours. In certain embodiments, the reaction time is about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

The reaction mixture may be maintained at a temperature of from about 0° C. to about 100° C., from about 10° C. to about 90° C., from about 15° C. to about 80° C., from about 20° C. to about 70° C., from about 20° C. to about 60° C., from about 20° C. to about 55° C., from about 20° C. to about 45° C., from about 20° C. to about 40° C., or from about 20° C. to about 35° C.

In certain embodiments, e.g., in a reaction conducted in a flow reactor, the reaction mixture may be maintained at a temperature as listed in the preceding sentence, or it may be maintained at a temperature exceeding some of the upper temperature limits of the preceding sentence, e.g., at a temperature of from about 40° C. to about 95° C.

In certain embodiments, the reaction mixture is maintained at from about 20° C. to about 45° C., preferably from about 25° C. to about 40° C. In certain embodiments, the reaction mixture is maintained more preferably at from about 25° C. to about 35° C., even more preferably at about 30° C. In certain especially preferred embodiments, the reaction mixture is maintained more preferably at from about 30° C. to about 38° C., more preferably at from about 32° C. to about 36° C., even more preferably at about 35° C. Typically, the oxidation reaction will be finished after about 24 hours or even less hours (e.g., 16 or 20 hours) when these preferred temperatures are used.

Typically, the oxidation of the oripavine during step (aa) is taking place in the presence of an oxidizing agent. Said oxidizing agent is either added to the reaction mixture, or it is formed in situ in the reaction mixture (e.g., performic acid may be formed in situ in a reaction mixture comprising formic acid and hydrogen peroxide). The oripavine is then oxidized to the 14-hydroxymorphinone salt, which will result when the acid $H^+_n X^{n-}$ is present.

The oripavine may be provided for step (aa) in a solution or suspension comprising the oripavine and a suitable solvent. A suitable solvent may comprise or consist of water; an alcohol (e.g., methanol, ethanol, n-propanol, isopropanol, 1-butanol, 2-butanol, isobutanol, tert-butanol, tert-amyl alcohol, 2-ethoxyethanol, 1-methoxy-2-propanol, etc.); an aromatic hydrocarbon (e.g., benzene, toluene, xylol, etc.); an ether (e.g., 1,4-dioxane, tetrahydrofuran, 2-methyl-tetrahydrofuran, diethylether, tert-butyl methyl ether, etc.); a ($C_1$-$C_4$) alkyl ester of a ($C_1$-$C_4$) alkanoic acid (e.g., methyl formate, methyl acetate, ethyl acetate, isopropyl acetate, etc.); an amide (e.g., dimethylformamide, diethylformamide, dimethylacetamide, or other N—($C_1$-$C_4$) alkyl substituted ($C_1$-$C_4$) alkanoic acid amides); N-methylpyrrolidone; formylmorpholine; or any mixtures of any of the foregoing. In certain embodiments, the reagent providing an acid for the process (e.g., 88% formic acid in water), or the acid itself can act as solvent. In certain embodiments, the solvent comprises or consists of water, an ether, an alcohol, or a combination thereof. In certain embodiments, the solvent comprises or consists of methanol, tetrahydrofuran, n-propanol, isopropanol, 1-butanol, 2-butanol, isobutanol, tert-butanol, acetone, ethanol, 1-methoxy-2-propanol, 2-ethoxyethanol, tert-amyl alcohol, or a mixture of water with any one of the foregoing. In certain embodiments, the solvent comprises or consists of tetrahydrofuran, isopropanol, methanol, ethanol, 1-butanol, 2-butanol, isobutanol, tert-butanol, tert-amyl alcohol, n-propanol or any combination thereof. In certain embodiments, the solvent is water or a combination of water with another solvent. In certain embodiments, the solvent is isopropanol or a mixture of isopropanol and water. In certain embodiments, the solvent is 2-butanol or a mixture of 2-butanol and water. In certain other embodiments, the solvent is free or substantially free from water (e.g., when the reaction is performed in chloroform using MCPBA as oxidizing agent). In certain preferred embodiments, the solvent comprises or consists of water.

The ratio of the oripavine to the solvent is selected such that the oripavine is dissolved in the solvent, i.e. such that a suspension or preferably a solution of the oripavine is formed. If the oxidizing agent contains or is generated with an acid which acts as a solvent (e.g., formic acid), or if the acid $H^+_n X^{n-}$ acts as a solvent, said acid contributes to the total amount of solvent in the reaction mixture or is the sole solvent in the reaction mixture. The ratio of the oripavine (in mmol) to the solvent (in mL) may be defined as molarity by the following formula:

molarity=(mmol of oripavine)/(milliliters of solvent).

For example, when 33.7 mmol of oripavine and 23.6 mL water plus formic acid are used, this results in a molarity of 1.43 (33.7/23.6). In the present process, the molarity of the oripavine in relation to the solvent is preferably ≥0.8. In certain embodiments, the molarity is from 0.8 to 1.8, preferably from 1.2 to 1.7, more preferably from 1.2 to 1.6 and even more preferably from 1.3 to 1.5. In comparison, in WO 2008/130553, the molarity is 0.67 ((10 mmol oripavine)/(15 mL water plus formic acid)). The less solvent is used, the more volume efficient steps (aa) and (bb) may be if the process yield remains constant. Thus, this process allows for the use of less solvent, which in turn may reduce the environmental burden and/or production costs.

In certain embodiments, the solvent comprises or consists of water, e.g. in the oxidation reactions described in the Examples. The ratio of the oripavine (in mmol) to water (in mL) in said embodiments is preferably from about 1:1 to about 5:1, more preferably from about 1.2:1 to about 4:1, more preferably from about 1.5:1 to about 3:1, more preferably from about 1.6:1 to about 2.4:1, even more preferably from about 1.7:1 to about 2.2:1. E.g., in a preferred embodiment, from about 1.5 mL to about 2.0 mL, preferably from about 1.6 to about 1.9 mL water per g oripavine are used. This calculation does not take into account water contained in one of the acids or other reagents (in particular, hydrogen peroxide) used in the oxidation reaction.

Before the oxidation reaction is initiated (e.g., by adding or generating an oxidizing agent), the oripavine may be present in any percentage of the reaction mixture. In certain embodiments, it is present in a starting amount of from about 1% to about 60%, from about 5% to about 50%, from about 10% to about 40%, from about 15% to about 35%, from about 20 to about 33%, or from about 20% to about 30% per weight of the complete reaction mixture. In certain preferred embodiments, the oripavine comprises from about 20 to about 33% of the reaction mixture by weight. In certain preferred embodiments, the oripavine comprises from about 20% to about 30% of the reaction mixture by weight. As the oxidation takes place, the concentration of the oripavine decreases and may finally approach 0%.

The oxidizing agent may be a peracid, a peroxide (which encompasses hydrogen peroxide and peroxide salts), a periodinane, singlet oxygen or any combination thereof. For example, an oxidizing agent may be hydrogen peroxide, potassium peroxymonosulfate (e.g., OXONE®), performic acid, peracetic acid (AcOOH), persulfuric acid, m-chloroperoxybenzoic acid (MCPBA), trifluoro peracetic acid, singlet oxygen, iodosylbenzene, $K_2O_2$, $Na_2O_2$, $Li_2O_2$, $Cs_2O_2$, $Cs_2O_2$, $K_2SO_5$, $NaSO_5$, or an appropriate mixture of any two or more of the foregoing. Said oxidizing agent may be either generated in situ in the reaction mixture (e.g., performic acid from hydrogen peroxide and an acid), or it may be added to the reaction mixture (e.g., MCPBA).

In certain embodiments, the oxidizing agent is a peracid. Said peracid may either be generated in situ in the reaction mixture from hydrogen peroxide and an acid or from another combination of reagents leading to the formation of a peracid (e.g., from a peroxide salt and an acid), or it may be added to the reaction mixture (e.g., MCPBA, or a peracid generated ex situ, i.e. separately from the reaction mixture before its addition to the reaction mixture). If the peracid is generated in situ, the peroxide may be added after the acid and/or at a pH of the reaction mixture which is less than 7.

In certain embodiments, the peracid may be performic acid, peracetic acid, MCPBA, potassium peroxymonosulfate (which contains one peracid group), trifluoro peracetic acid, persulfuric acid, or a combination of any two or more thereof. When said peracid is generated in situ, the corresponding starting acid is formic acid, acetic acid, 3-chlorobenzoic acid, potassium monosulfate, trifluoroacetic acid, sulfuric acid, or a mixture of any two or more of the foregoing.

In certain embodiments, the peracid comprises or is performic acid. When the performic acid is generated in situ or ex situ, it is in one embodiment generated from formic acid and hydrogen peroxide.

In certain embodiments, the peracid comprises or is a combination of performic acid and persulfuric acid. When said combination is generated in situ or ex situ, it is in one embodiment generated from formic acid, sulfuric acid and hydrogen peroxide.

In certain embodiments, the oxidizing agent is or is generated from hydrogen peroxide (e.g., added to the reaction mixture in 5, 10, 15, 20, 25, 30, 35, 40, 45, 50, 60, or 70% aqueous solution). In certain embodiments, 35% aqueous solution of hydrogen peroxide is added to the reaction mixture. In certain embodiments, at the beginning of the reaction, hydrogen peroxide may comprise about 8-10% of the reaction mixture by volume, and, as the oxidation reaction takes place, the concentration of hydrogen peroxide decreases and may even reach 0%.

In general, the oxidizing agent, e.g., a peracid generated from an acid and hydrogen peroxide, is present in an amount of from about 0.8 to about 5 moles per mole of the oripavine. In certain embodiments, from about 1 to about 2 moles of the oxidizing agent per 1 mole of the oripavine are utilized. In certain embodiments, about 1, about 1.1, about 1.2, about 1.3, about 1.4, about 1.5, about 1.6, about 1.8, or about 1.9 moles of the oxidizing agent per mole of the oripavine are used. In certain embodiments, from about 1 to about 1.6 moles of the oxidizing agent per mole of the oripavine are utilized. In certain embodiments, from about 1 to about 1.4 moles of the oxidizing agent per mole of the oripavine are utilized. In certain embodiments, from about 1.2 to about 1.4 moles of the oxidizing agent per mole of the oripavine are utilized. In certain embodiments, from about 1.2 to about 1.3 moles (e.g., 1.25 molar equivalents) of the oxidizing agent per mole of the oripavine are utilized. In certain embodiments, from about 1 to about 1.25 moles of the oxidizing agent per mole of the oripavine are utilized. In certain embodiments, from about 1.05 to about 1.15 moles (e.g., 1.05 molar equivalents) of oxidizing agent per mole of the oripavine are used. In embodiments wherein a peracid is generated in situ, the molar amount of the starting component containing the peroxy group (e.g., hydrogen peroxide) is deemed to represent the molar amount of the resulting peracid in the reaction mixture.

In those embodiments wherein the oxidizing agent is a peracid generated in situ from hydrogen peroxide and an acid in the reaction mixture, preferably from about 1 to about 1.6 moles of hydrogen peroxide per mole of the oripavine are utilized. In certain embodiments, from about 1 to about 1.5 moles of hydrogen peroxide per mole of the oripavine are utilized. In certain embodiments, from about 1.2 to about 1.4 moles of hydrogen peroxide per mole of the oripavine are utilized. In certain embodiments, from about 1.2 to about 1.3 moles (e.g., 1.25 molar equivalents) of the oxidizing agent per mole of the oripavine are utilized. In certain embodiments, from about 1 to about 1.25 moles of hydrogen peroxide per mole of the oripavine are utilized. In certain embodiments, from about 1.05 to about 1.15 moles (e.g., 1.05 molar equivalents) of hydrogen peroxide per mole of the oripavine are used.

In a preferred embodiment, from about 1 to about 1.5 moles of the oxidizing agent per mole of the oripavine are utilized, and more preferably, especially in cases where full conversion shall be achieved within about 24 hours or less, from about 1.2 to about 1.5 moles or from about 1.2 to about 1.4 moles of the oxidizing agent per mole of the oripavine are utilized. This means that in said preferred embodiment, when the oxidizing agent is a peracid generated in situ from hydrogen peroxide and an acid in the reaction mixture, from about 1 to about 1.5 moles of hydrogen peroxide per mole of the oripavine are utilized, and more preferably, from about 1.2 to about 1.4 moles of hydrogen peroxide per mole of the oripavine are utilized. In a particular aspect of said preferred embodiment, from about 1.2 to about 1.3 moles (e.g., about 1.25 moles) of hydrogen peroxide per mole of the oripavine are utilized.

In those embodiments wherein the oxidizing agent is a peracid generated in situ from hydrogen peroxide and an acid in the reaction mixture, the acid for generating the peracid preferably is or comprises formic acid. This also encompasses processes wherein the peracid is generated from a combination of formic acid and sulfuric acid.

The molar amount of an acid used for generating a peracid in situ may be less than, equal to, or exceeding the molar amount of the oripavine. In certain embodiments, an excess of said acid over the amount of the oripavine will be utilized. In certain embodiments, said acid is used in excess over the amount of the peroxide (e.g., hydrogen peroxide) which is used to generate the peracid. In certain embodiments, the amount of the acid used for generating the peracid (e.g., of formic acid) is from about 0.5 to about 14 molar equivalents per molar equivalent of the oripavine, preferably from about 1 to about 12 molar equivalents, more preferably from about 1 to about 7 molar equivalents, more preferably from about 1.5 to about 6 molar equivalents, more preferably from about 2 to about 5 molar equivalents, more preferably from about 2.5 to about 4.5 molar equivalents, even more preferably from about 2.5 to 4 molar equivalents per molar equivalent of the oripavine.

In a specific aspect of the oxidation reaction, the molar amount of the acid used for generating the peracid in situ is from about 2.5 to about 4.5 equivalents per molar equivalent of the oripavine, and the molar amount of the peroxide is from about 1 to about 1.5 moles, preferably from about 1.2 to about 1.4 moles, more preferably from about 1.2 to about 1.3 moles per mole of the oripavine. In said aspect, the acid is preferably formic acid, and the peroxide is preferably hydrogen peroxide.

When an acid is used for generating the oxidizing agent in situ, two acids may be used during a process encompassing steps (aa) and (bb): a first acid (which is used to generate at least a part of the peracid in situ in step (aa)), and a second acid (which is the acid $H^+{}_nX^{n-}$ of step (bb), which in certain embodiments may also generate a part of the peracid in situ in step (aa)). The second acid may be added before, simultaneously with, or after addition of the first acid. In certain embodiments, the acids are pre-mixed and the pre-mixture is added to the solution or suspension. In certain embodiments, the first acid and the second acid may each be independently added all at once or in divided portions. In certain embodiments, the first acid is formic acid and the second acid is sulfuric acid.

The acid $H^+{}_nX^{n-}$ of step (bb) may be added as acid $H^+{}_nX^{n-}$ or may be generated in situ in the reaction mixture from a salt containing an anion $X^{n-}$.

The acid $H^+{}_nX^{n-}$ may be added (or generated in situ) before, during or after the oxidation reaction of step (aa), or at any combination of these time points. It may be added once, in several batches or continuously over a certain period of time. It may be added at or during several points in time in relation to the oxidation reaction, e.g., before, during and after the oxidation, or before and during the oxidation reaction. If it is added (or generated) before and/or during the oxidation reaction, the process comprising steps (aa) and (bb) is performed as a one-pot-reaction. Said one-pot-reaction may be more cost-, time- and/or volume-efficient and may therefore be preferred. Especially preferred is a process wherein the acid $H^+{}_nX^{n-}$ is added to (or generated in) the reaction mixture before the oxidation reaction of step (aa).

In certain embodiments, a portion or all of the acid $H^+{}_nX^{n-}$ is added after some or substantially all of the oripavine has been oxidized. In certain embodiments, $H^+{}_nX^{n-}$ is added after substantially all of the oripavine has been consumed.

In certain embodiments, step (bb) of the process is performed by adding $H^+{}_nX^{n-}$ (e.g., $H_2SO_4$) to the reaction mixture.

$H^+{}_nX^{n-}$ may be any acid containing an anion $X^{n-}$ as defined herein. It may, for example, be HCl, $H_2SO_4$ or its monosalt, methanesulfonic acid, tosylic acid, trifluoroacetic acid, $H_3PO_4$ or one of its mono- or disalts, oxalic acid, perchloric acid, or any mixtures thereof. In certain embodiments, it may be HCl, $H_2SO_4$, methanesulfonic acid, tosylic acid, trifluoroacetic acid, or a mixture thereof. In certain embodiments, it is $H_2SO_4$, methanesulfonic acid, or trifluoroacetic acid or a mixture thereof. In certain embodiments, it is trifluoroacetic acid. In certain embodiments, it is $H_2SO_4$. In certain embodiments, it is methanesulfonic acid.

$H^+{}_nX^{n-}$ may in certain embodiments be polymer supported if n is 2 or 3.

The molar amount of $H^+{}_nX^{n-}$ present in step (bb) may be the same as or different from the molar amount of the oripavine provided for step (aa). For example, in embodiments wherein n is 2, the salt or acid added in step (bb), e.g., $H_2SO_4$ or a salt thereof, may be added in an amount of from about 0.1 to about 1.5 molar equivalents, preferably of from about 0.1 to about 1.2 molar equivalents, more preferably of from about 0.1 to about 1 molar equivalents, even more preferably of from about 0.25 to about 0.75 molar equivalents, even more preferably of from about 0.4 to about 0.6 molar equivalents, even more preferably of from about 0.45 to about 0.55 molar equivalents or from about 0.5 to about 0.6 molar equivalents per molar equivalent of the oripavine. In certain embodiments wherein n is 2, the salt or acid added in step (bb), e.g., $H_2SO_4$ or a salt thereof, is added in an amount of about 0.5 to about 0.6 equivalents, e.g. of about 0.51 to about 0.55 molar equivalents per molar equivalent of the oripavine.

In certain embodiments, the amount of $H^+$ provided by $H^+{}_nX^{n-}$ in step (bb) is in a slight molar excess in comparison to the oripavine. In certain embodiments, the molar amount of $H^+{}_nX^{n-}$ present in step (bb) is within a range of about 1/n+10% to about 1/n+20% molar equivalents per one molar equivalent of the oripavine.

In certain embodiments, the acid $H^+{}_nX^{n-}$ is the only acid used during the process encompassing steps (aa) and (bb). In those embodiments where a peracid is used as oxidizing agent, said acid $H^+{}_nX^{n-}$ is capable to form a peracid and will be used for generating said peracid.

In certain other embodiments, one or more additional acids are added to the reaction mixture. In those embodiments where a peracid is used as oxidizing agent, there may be used an acid for generating the peracid which is different from the acid $H^+{}_nX^{n-}$. This acid is then an additional acid. In other embodiments, a further additional acid may be added to the reaction mixture in addition to the acid $H^+{}_nX^{n-}$ and the acid for generating the peracid. Such further acid may be any remaining acid selected from the acids defined as the acid $H^+{}_nX^{n-}$ and as the acid for generating the peracid in the present description, or any mixture of said remaining acids.

The total amount of acid used during steps (aa) and (bb) of the oxidation process is important, because it may influence whether or not the 14-hydroxymorphinone salt precipitates from the reaction mixture during the process. It also determines the amount of base which will be required after completion of the reaction if a neutralization of the reaction mixture is desired. The total amount of acid includes the acid $H^+{}_nX^{n-}$ and, if present, the acid used for generating a peracid and any further acid added to the reaction mixture during steps (aa) and (bb). The total amount of acid may range from about 0.6 to about 14.0 molar equivalents of total acid per molar equivalent of the oripavine.

In certain embodiments, from about 1 to about 12 molar equivalents of total acid per molar equivalent of the oripavine are used. In certain embodiments, from about 1 to about 10, from about 1 to about 8, from about 1 to about 7, from about 1 to about 6.5, from about 1 to about 6, from about 1 to about 5.5, from about 1 to about 5, from about 1 to about 4.5, from about 1 to about 4, from about 1 to about 3.5, or from about 1.5 to about 3.5 molar equivalents of total acid per molar equivalent of the oripavine are used.

In certain embodiments, from about 1 to about 8 molar equivalents, preferably from about 1 to about 5 molar equivalents, more preferably from about 1.5 to about 4.5 molar equivalents, even more preferably from about 3 to about 4 molar equivalents of total acid per molar equivalent of the oripavine are used.

In certain embodiments, from about 1.2 to about 4.5 molar equivalents of total acid per molar equivalent of the oripavine are used.

In certain embodiments, from about 2.5 to about 5.5 molar equivalents, preferably from about 3 to about 5 molar equivalents of total acid per molar equivalent of the oripavine are used.

In certain embodiments where an acid $H^+{}_nX^{n-}$ and an acid used for generating the peracid (which is different from $H^+{}_nX^{n-}$) are used, the molar ratio of the acid $H^+{}_nX^{n-}$ to the acid used for generating the peracid (e.g., of sulfuric acid to formic acid) is from about 1:20 to about 1:0.5, from about 1:17 to about 1:1, from about 1:15 to about 1:1, from about 1:14 to about 1:1, from about 1:12 to about 1:1, from about 1:10 to about 1:1, from about 1:9 to about 1:2, from about 1:8 to about 1:3, from about 1:7 to about 1:3, from about 1:7 to about 1:5, or a numeric value lying within these ranges. In certain embodiments, the molar ratio of the acid $H^+{}_nX^{n-}$ to the acid used for generating the peracid is from about 1:9 to about 1:4, preferably from about 1:7.5 to about 1:4, more preferably from about 1:7 to about 1:5, or a numeric value lying within these ranges.

In certain embodiments, from about 2.5 to about 4.5 molar equivalents of the acid used for generating a peracid per molar equivalent of the oripavine are used, and from about 0.1 to about 1.5, from about 0.1 to about 1, from about 0.2 to about 0.9, from about 0.25 to about 0.75, from about 0.4 to about 0.6, or from about 0.5 to about 0.6 molar equivalents of the acid $H^+{}_nX^{n-}$ per molar equivalent of the oripavine are used. In said embodiments, said first acid may be formic acid, and said second acid may be sulfuric acid.

In certain embodiments, from about 0.5 to about 4 molar equivalents of the acid used for generating a peracid per molar equivalent of the oripavine are used, and from about 0.1 to about 1.5, from about 0.1 to about 1, from about 0.2 to about 0.9, from about 0.25 to about 0.75, from about 0.4 to about 0.6, or from about 0.5 to about 0.6 molar equivalents of the acid $H^+{}_nX^{n-}$ per molar equivalent of the oripavine are used. In said embodiments, said first acid may be formic acid, and said second acid may be sulfuric acid.

In certain embodiments, from about 0.5 to about 3.5 molar equivalents of the acid used for generating a peracid per molar equivalent of the oripavine are used, and from about 0.1 to about 1.5, from about 0.1 to about 1, from about 0.2 to about 0.9, from about 0.25 to about 0.75, from about 0.4 to about 0.6, or from about 0.5 to about 0.6 molar equivalents of the acid $H^+{}_nX^{n-}$ per molar equivalent of the oripavine are used. In said embodiments, said first acid may be formic acid, and said second acid may be sulfuric acid.

In certain embodiments, from about 1 to about 3 molar equivalents of the acid used for generating a peracid per molar equivalent of the oripavine are used, and from about 0.4 to about 0.6, or from about 0.5 to about 0.6 molar equivalents of the acid $H^+{}_nX^{n-}$ per molar equivalent of the oripavine are used. In said embodiments, said first acid may be formic acid, and said second acid may be sulfuric acid.

In a preferred embodiment utilizing formic acid and sulfuric acid, the oxidation is performed by oxidizing the oripavine in the presence of about 12 molar equivalents or less, about 10 molar equivalents or less, about 8 molar equivalents or less, about 7 molar equivalents or less, about 6 molar equivalents or less, about 5 molar equivalents or less, about 4 molar equivalents or less, about 3 molar equivalents or less, about 2 molar equivalents or less, or about 1 molar equivalents (e.g., 1.05 molar equivalents) or less of total acid per one molar equivalent of the oripavine, wherein from about 0.1 to about 1.5 molar equivalents of total acid comes from the acid $H^+{}_nX^{n-}$. In one particular embodiment, the oripavine is oxidized to the 14-hydroxymorphinone salt by exposing each molar equivalent of the oripavine to (i) from about 1.0 to about 1.6, preferably from about 1.2 to about 1.4 molar equivalents of hydrogen peroxide, (ii) from about 0.3 to about 9, from about 0.5 to about 8, from about 0.5 to about 4.5, or from about 2.5 to about 4.5 molar equivalents of the acid used for generating the peracid, and (iii) from about 0.1 to about 1.5, from about 0.25 to about 0.9, or from about 0.4 to about 0.6 molar equivalents of the acid $H^+{}_nX^{n-}$. In certain embodiments, from about 2.5 to about 4 molar equivalents of the acid used for generating the peracid per one molar equivalent of the oripavine are used. In certain embodiments, from about 0.4 to about 0.6 molar equivalents of the acid $H^+{}_nX^{n-}$, and from about 2.5 to about 4 molar equivalents of the acid used for generating the peracid are used. In certain embodiments, from about 0.4 to about 0.6 molar equivalents of the acid $H^+{}_nX^{n-}$, and from about 1 to about 3 molar equivalents of the acid used for generating the peracid are used. In certain embodiments, from about 0.5 to about 0.6 molar equivalents of the acid $H^+{}_nX^{n-}$, and from about 2.5 to about 4.5 molar equivalents of the acid used for generating the peracid are used. In certain embodiments, conducting the oxidation reaction under these conditions may improve the volume efficiency of the reaction and may reduce the number and amounts of by-products formed during the oxidation reaction.

In certain embodiments, a portion or all of the $H^+{}_nX^{n-}$ (e.g., $H_2SO_4$) is added to the reaction mixture before the acid or the peroxide used for generating the peracid is added, or at the same point in time.

In certain embodiments, $H^+{}_nX^{n-}$ (e.g., $H_2SO_4$) is added after the acid used for generating the peracid (e.g., formic acid). In certain embodiments, the reaction mixture may already comprise formic acid, and sulfuric acid is then added.

In preferred embodiments, the 14-hydroxymorphinone salt is precipitated from the reaction mixture, either because the presence of the acid $H^+{}_nX^{n-}$ (e.g., $H_2SO_4$) induces the precipitation of the 14-hydroxymorphinone salt or a solvate thereof during the oxidation reaction, or because in addition to said presence the precipitation is started or enhanced by other measures, e.g., by adjusting the temperature of the solution and/or adding a suitable antisolvent to the solution, as described in more detail below. In certain embodiments, precipitation is achieved by adding a suitable antisolvent. In certain embodiments, precipitation is achieved by lowering the temperature below the reaction temperature of the oxidation reaction.

The reaction steps (aa) and (bb) are typically performed in a solvent. The amount of said solvent is described above with regard to molarity.

In certain embodiments, the oxidizing agent is or comprises performic acid generated, e.g., from hydrogen peroxide and formic acid, and the solvent is water, an alcohol, a mixture of two or more alcohols, or a mixture of an alcohol and water. The solvent may be methanol or a mixture of methanol and water. The solvent may be isopropanol or a mixture of isopropanol and water. The solvent may be water.

In certain embodiments, the oxidizing agent is or comprises performic acid and persulfuric acid generated, e.g., from hydrogen peroxide and formic acid and sulfuric acid, and the solvent is water, an alcohol, a mixture of two or more alcohols, or a mixture of an alcohol and water. The solvent may be methanol or a mixture of methanol and water. The solvent may be isopropanol or a mixture of isopropanol and water. The solvent may be water.

In certain embodiments, the oxidizing agent is or comprises peracetic acid, and the solvent is water, an alcohol, a mixture of two or more alcohols, or a mixture of an alcohol and water.

In certain embodiments, step (aa) is performed with an oxidizing agent formed from an acid and hydrogen peroxide. In certain embodiments, the amount of total acid present in the reaction mixture is about 12 molar equivalents or less, about 10 molar equivalents or less, about 8 molar equivalents or less, about 7 molar equivalents or less, about 6 molar equivalents or less, about 5 molar equivalents or less, about 4 molar equivalents or less, about 3 molar equivalents or less, about 2 molar equivalents or less, or about 1 molar equivalents (e.g., 1.05 molar equivalents) or less per molar equivalent of oripavine. In one particular embodiment, the oripavine is oxidized to the 14-hydroxymorphinone by exposing each molar equivalent of the oripavine to from about 1.0 to about 1.6, preferably from about 1.2 to about 1.4 molar equivalents of hydrogen peroxide, from about 0.3 to about 9 molar equivalents, from about 0.5 to about 8 molar equivalents, or from about 2.5 to about 4.5 molar equivalents of formic acid, and from about 0.4 to about 0.6 molar equivalents of sulfuric acid. In certain embodiments, from about 0.5 to about 5 molar equivalents of formic acid per one molar equivalent of oripavine are used. In certain embodiments, from about 2.5 to about 4.5 molar equivalents of formic acid per one molar equivalent of oripavine are used. In certain embodiments, from about 2.5 to about 4 molar equivalents of formic acid per one molar equivalent of oripavine are used.

In certain embodiments, the oxidation process is performed by: (i) forming a solution or a suspension comprising oripavine and from about 1.5 to about 4 molar equivalents of a first acid (e.g., formic acid) per molar equivalent of oripavine, (ii) adding from about 0.4 to about 0.6 molar equivalents of the acid $H^+{}_nX^{n-}$ (e.g., sulfuric acid) per molar equivalent of oripavine to the solution or the suspension, (iii) adding from about 1 to about 1.6 molar equivalents of hydrogen peroxide to the solution or the suspension from (ii), and (iv) precipitating the 14-hydroxymorphinone salt from the solution or suspension (e.g., by adjusting the temperature of the solution and/or adding a suitable antisolvent to the solution, as described in more detail below). In certain embodiments, precipitation is achieved by adding a suitable antisolvent. In certain embodiments, precipitation is achieved by lowering the temperature below the reaction temperature of the oxidation reaction.

In certain embodiments, the oxidation process is performed by: (i) forming a solution or a suspension comprising oripavine and from about 2.5 to about 4.5 molar equivalents of a first acid (e.g., formic acid) per molar equivalent of oripavine, (ii) adding from about 0.5 to about 0.6 molar equivalents of the acid $H^+_n X^{n-}$ (e.g., sulfuric acid) per molar equivalent of oripavine to the solution or the suspension, (iii) adding from about 1.0 to about 1.4 molar equivalents, preferably from about 1.2 to about 1.4 molar equivalents, and more preferably from about 1.2 to about 1.3 molar equivalents of hydrogen peroxide to the solution or the suspension from (ii), and (iv) precipitating the 14-hydroxymorphinone salt from the solution or suspension (e.g., by adjusting the temperature of the solution and/or adding a suitable anti solvent to the solution, as described in more detail below). In certain embodiments, precipitation is achieved by adding a suitable antisolvent. In certain embodiments, precipitation is achieved by lowering the temperature below the reaction temperature of the oxidation reaction.

In certain embodiments, the amount of 8-hydroxyoxymorphone in the oxidation reaction product containing the 14-hydroxymorphinone salt is less than about 2500 ppm, less than about 2000 ppm, less than about 1500 ppm, less than about 1000 ppm, less than about 500 ppm, less than about 100 ppm, less than about 50 ppm, less than about 10 ppm, less than about 5 ppm, or less than about 1 ppm of the 14-hydroxymorphinone. In certain embodiments, the amount of 8-hydroxyoxymorphone in the reaction product containing the 14-hydroxymorphinone salt is the amount described in Section V. In certain embodiments, the oxidation reaction product is free from 8-hydroxyoxymorphone.

In certain embodiments, oripavine is oxidized to 14-hydroxymorphinone, wherein the reaction mixture comprises more than one acid (e.g., two acids), and comprises less than about 14 molar equivalents of total acid per molar equivalent of oripavine (e.g., from about 0.5 to about 11, from about 1 to about 10.5, from about 1.5 to about 5, or from about 3 to about 5 molar equivalents of acid per molar equivalent of oripavine).

In certain embodiments, oripavine is oxidized to 14-hydroxymorphinone, wherein the reaction mixture comprises more than one acid (e.g., two acids), and comprises less than about 8 molar equivalents of total acid per molar equivalent of oripavine (e.g., from about 0.5 to about 7, from about 1 to about 5, from about 1.2 to about 4.5, from about 2.5 to about 4.5, or from about 3 to about 4 molar equivalents of total acid per molar equivalent of oripavine).

In certain embodiments of the process, oripavine is oxidized to 14-hydroxymorphinone in a solution or suspension containing a mixture of formic acid and sulfuric acid, the mixture comprising not more than about 14 molar equivalents of total acid per one molar equivalent of oripavine (e.g., from about 0.5 to about 11, from about 1 to about 10.5, from about 1.5 to about 5, or from about 3 to about 5 molar equivalents of acid per one molar equivalent of oripavine).

There are also alternative ways to perform step (bb) than by adding to the reaction mixture. In step (bb) of the process, the $H^+_n X^{n-}$ can be generated by adding a salt containing $X^{n-}$. Said salt may have the formula

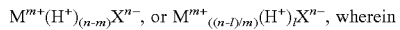

$M^{m+}$ is a monovalent or polyvalent metal cation;
m and n are independently from each other an integer selected from 1, 2, and 3, provided that m is ≤n; and
l is an integer selected from 0, 1, and 2, provided that l<n.

The metal cation may be an alkali metal cation, an alkaline earth metal cation or a Group III cation. Exemplary cations are $Na^+$, $K^+$, $Ca^{2+}$. Exemplary salts are $NaHSO_4$, $KHSO_4$, $Na_2SO_4$, $K_2SO_4$, $NaH_2PO_4$, $Na_2HPO_4$, $Na_3PO_4$, $KH_2PO_4$, $K_2HPO_4$, $K_3PO_4$.

The oxidation reaction may be prepared in any suitable reaction vessel. In certain embodiments, the reaction vessel is a flow reactor. In certain other embodiments, the reaction vessel is not a flow reactor. In certain embodiments, the reaction vessel is a continuous flow reactor. In certain other embodiments, the reaction vessel is not a continuous flow reactor.

Precipitation and/or Isolation of the 14-Hydroxymorphinone Salt

The 14-hydroxymorphinone salt or the solvate thereof may be provided as a solid, or in solution or suspension as a result of the oxidation process encompassing steps (aa) and (bb). In certain preferred embodiments, the process is performed under conditions wherein the 14-hydroxymorphinone salt or a solvate thereof is insoluble in the reaction mixture. In these embodiments, the process may comprise an additional step (cc) of precipitating the 14-hydroxymorphinone salt or the solvate thereof from the reaction mixture.

As already pointed out in the Definitions section, "precipitating" encompasses "crystallizing" unless stated otherwise.

The precipitation may start as soon as $H^+_n X^{n-}$ is present in the reaction mixture (e.g., after addition of an acid $H^+_n X^{n-}$), or it may start at a later point in time. In other words, it may take place during and/or after the oxidation reaction.

The precipitation of the 14-hydroxymorphinone salt or the solvate thereof may be caused by the presence of the acid $H^+_n X^{n-}$ in the reaction mixture. It may be enhanced by adding an additional amount of the acid $H^+_n X^{n-}$ or the salt containing $X^{n-}$ to the reaction mixture during step (bb).

In certain embodiments, the precipitation of the 14-hydroxymorphinone salt or the solvate thereof may require the cooling of the reaction mixture and/or the addition of an antisolvent.

In certain embodiments wherein the 14-hydroxymorphinone salt or a solvate thereof precipitates from the reaction mixture, the acid $H^+_n X^{n-}$ is $H_2SO_4$ or its monosalt, methanesulfonic acid, tosylic acid, trifluoroacetic acid, $H_3PO_4$ or one of its mono- or disalts, oxalic acid, perchloric acid, or any mixtures thereof. In certain embodiments, it may be $H_2SO_4$, methanesulfonic acid, tosylic acid, trifluoroacetic acid, or a mixture thereof. In certain embodiments, it is $H_2SO_4$, methanesulfonic acid, or trifluoroacetic acid or a mixture thereof. In certain embodiments, it is trifluoroacetic acid. In certain embodiments, it is $H_2SO_4$. In certain embodiments, it is methanesulfonic acid. Preferably, it is $H_2SO_4$.

The 14-hydroxymorphinone salt or the solvate thereof, once precipitated, may either be isolated (i.e. separated from the reaction mixture), or it may be converted without preceding isolation to oxymorphone or a salt or solvate thereof. Preferably, it is isolated before the hydrogenation process of the present invention is performed.

Precipitation of the 14-hydroxymorphinone salt may be influenced by the molar ratio of the anion $X^{n-}$ to the oripavine (see above), by the amount of total acid present during the oxidation reaction (as compared to molar equivalents of the oripavine), by the temperature before, during or after the oxidation reaction, by the kind and amount of solvent (e.g., water) present in the reaction mixture, by the presence of an antisolvent added to the reaction mixture, by the rate at which the reactants are added during the process to the reaction mixture, or by a combination of any of the foregoing.

In certain embodiments, the precipitation of the 14-hydroxymorphinone salt or a solvate thereof is initiated and/or enhanced by one or more of the following:
(i) adjusting (e.g., lowering) the temperature of the reaction mixture to the precipitation temperature;
(ii) addition of an antisolvent;
(iii) addition of a seed crystal;
(iv) lowering the pH;
(v) changing the ionic strength of the reaction mixture (e.g., by addition of a salt);
(vi) concentrating the reaction mixture;
(vii) reducing or stopping agitation of the reaction mixture; or any other conventional method for initiating or enhancing precipitation or crystallization.

When the temperature is adjusted to the precipitation temperature, this means that the precipitation of the 14-hydroxymorphinone salt or the solvate thereof is initiated and/or enhanced by adjusting the temperature of the reaction mixture to or beyond a temperature at which said compound precipitates ("precipitation temperature"). The temperature is either adjusted by performing the oxidation reaction at the precipitation temperature, or by lowering the temperature of the reaction mixture during the reaction or after completion of the reaction.

In certain embodiments, the reaction mixture is adjusted to a temperature of ≤40° C. to initiate precipitation, i.e. the precipitation temperature is ≤40° C. In certain embodiments, the precipitation is initiated at a precipitation temperature of about −20° C., about −15° C., about −10° C., about −5° C., about 0° C., about 5° C., about 10° C., about 15° C., about 17° C., about 19° C., about 21° C., about 23° C., about 25° C., about 27° C., about 29° C., about 31° C., about 33° C., about 35° C., about 37° C., or about 40° C.

In certain embodiments, the precipitation temperature is in a range of from about −20° C. to about 40° C., preferably from about 0° C. to about 40° C., more preferably from about 5° C. to about 35° C., more preferably from about 5° C. to about 30° C., even more preferably from about 5° C. to about 20° C.

In certain embodiments, the precipitation temperature is in a range of from about 5° C. to about 22° C., preferably from 5° C. to about 18° C., more preferably from about 8° C. to about 15° C.

In certain embodiments, the precipitation temperature is in a range of from about 5° C. to about 18° C.; or from about 8° C. to about 15° C.

In certain embodiments, an antisolvent is used in addition to adjusting the temperature to the precipitation temperature. In certain embodiments, e.g., when the 14-hydroxymorphinone salt is 14-hydroxymorphinone sulfate, precipitation will also occur without adding an antisolvent.

If an antisolvent is used for initiating precipitation, the precipitation temperature may be in a range of from about −20° C. to about 40° C., from about 0° C. to about 40° C., from about 5° C. to about 35° C., from about 5° C. to about 22° C., from about 5° C. to about 18° C.; or from about 8° C. to about 15° C.

In certain embodiments, the reaction mixture is cooled at a controlled rate during precipitation. In certain embodiments, the cooling rate is about 1° C., about 2° C., about 3° C., about 4° C., or about 5° C. per hour.

An important factor influencing the precipitation of a 14-hydroxymorphinone salt or a solvate thereof in the oxidation process may be the temperature of the reaction mixture. A further factor influencing the precipitation appears to be the total amount of acid in the reaction mixture. Another factor influencing the precipitation appears to be the molarity of the reaction mixture. The addition of an antisolvent also appears to be a factor that can influence precipitation of a 14-hydroxymorphinone salt or a solvate thereof. It is presently believed that the precipitation temperature will rise when the total amount of acid is lowered.

Hence, in a process wherein the 14-hydroxymorphinone salt or the solvate thereof is precipitated and wherein the total amount of acid present in the reaction mixture is from about 0.6 to about 14.0 molar equivalents of total acid per molar equivalent of oripavine, the precipitation temperature may be ≤40° C. (i.e. 40° C. or less). In a process wherein the total amount of acid present in the reaction mixture is from about 1 to about 8 molar equivalents, preferably from about 1 to about 5 molar equivalents of total acid per molar equivalent of the oripavine, the precipitation temperature may be in a range of from about 0° C. to about 40° C., preferably from about 0° C. to about 35° C. In a process wherein the total amount of acid present in the reaction mixture is from about 1 to about 4 molar equivalents, preferably from about 1 to about 3 molar equivalents of total acid per molar equivalent of the oripavine, the precipitation temperature may be in a range of from about 5° C. to about 22° C.; preferably from about 8° C. to about 20° C., more preferably from about 8° C. to about 15° C. Further examples of such correlations can be found in the Examples section of PCT/IB2013/001541.

In certain embodiments, an antisolvent is added to precipitate a 14-hydroxymorphinone salt or a solvate thereof. When an antisolvent is added to the reaction mixture, it is added either during or after step (bb) and in an effective amount to initiate and/or enhance precipitation. In certain embodiments, addition of a suitable antisolvent increases the yield of the reaction. Addition of a suitable antisolvent may also enhance retention of 8-hydroxyoxymorphone in the supernatant. A suitable antisolvent may comprise or consist of tert-butyl methyl ether, diethyl ether, hexane(s), tert-amyl alcohol, methanol, ethanol, isopropanol, 2-butanol, heptanes, xylenes, toluene, acetone, 2-butanone, ethyl acetate, tetrahydrofuran, 1,2-dichloroethane, chloroform, dichloromethane, 1-methoxy-2-propanol, 2-ethoxyethanol, n-propanol, 1-butanol, tert-butanol, isobutanol, isopropyl acetate, 1,4-dioxane, 2-methyl-tetrahydrofuran, methyl formate, methyl acetate, or a mixture of two or more of any of the foregoing. 14-Hydroxymorphinone sulfate has very low/no solubility in these solvents at room temperature. The listed alcohols and ethers are the preferred antisolvents. In some embodiments, said antisolvent is an alcohol, e.g., methanol, isopropanol or 2-butanol. In some embodiments, said antisolvent is an ether, e.g., tert-butyl methyl ether and/or tetrahydrofuran. In some preferred embodiments, said antisolvent is isopropanol or 2-butanol. In some embodiments, said antisolvent is a mixture of an alcohol (e.g., methanol) and an ether (e.g., tert-butyl methyl ether and/or tetrahydrofuran), for example a mixture of methanol and tert-butyl methyl ether, or a mixture of methanol and tetrahydrofuran, or a mixture of tert-butyl methyl ether and tetrahydrofuran, or a mixture of methanol, tert-butyl methyl ether, and tetrahydrofuran. When two or more antisolvents are used (e.g., in a mixture), they can be added as a mixture or separately.

When an antisolvent is added, it is preferably added in an amount of from about 0.5 to about 7 mL anti solvent per 1 g oripavine, more preferably in an amount of from about 0.5 to about 5 mL antisolvent per 1 g oripavine, more preferably in an amount of from about 0.5 to about 4 mL antisolvent per 1 g oripavine. For example, in a preferred embodiment, from about 1 to about 4 mL 2-butanol (e.g., 3.6 mL) per 1 g of oripavine are added. Within these ranges, the yield is especially increased and/or the retention of 8-hydroxyoxymorphone in the supernatant is especially enhanced.

When a seed crystal is added, said seed crystal is a crystal of the 14-hydroxymorphinone salt or a solvate thereof. This seed crystal may act as crystallization nucleus if the solution of the 14-hydroxymorphinone salt resulting from step (bb) is metastable. It may be made metastable by concentrating the reaction mixture.

In certain embodiments, the precipitate may be isolated from the reaction mixture (isolation step (dd)).

In said isolation step (dd), the precipitate may be separated from the supernatant in any conventional manner, e.g., by filtration, centrifugation, decanting, or any other conventional method for separating a solid phase from a liquid phase. In certain embodiments, the ratio of 8-hydroxyoxymorphone (either in its free base form or bound in a salt or solvate) to 14-hydroxymorphinone (which may be bound in the 14-hydroxymorphinone salt) in the precipitate is less than the ratio of 8-hydroxyoxymorphone to 14-hydroxymorphinone in the supernatant.

In cases where the 14-hydroxymorphinone salt or a solvate thereof is not precipitated, it may be isolated by concentrating the reaction mixture, e.g., by drying, vacuum distillation, spray drying or lyophilization.

Further Processing of the 14-Hydroxymorphinone Salt or the Solvate Thereof

In certain embodiments, the precipitate containing the 14-hydroxymorphinone salt or the solvate thereof can be further processed.

In certain embodiments, the isolated precipitate containing the 14-hydroxymorphinone salt or solvate thereof may be washed with and/or (re)crystallized in an organic solvent or aqueous solvent in which 8-hydroxyoxymorphone or a salt or solvate thereof is more soluble than the 14-hydroxymorphinone salt or solvate thereof. The washing and/or (re)crystallization may further reduce the amount of 8-hydroxyoxymorphone in the isolated precipitate containing the 14-hydroxymorphinone salt or solvate thereof. The washing and/or the (re)crystallization may be performed more than once, or they may also be combined sequentially.

In certain embodiments, the isolated precipitate containing the 14-hydroxymorphinone salt or solvate thereof is washed with and/or is (re)crystallized in a solvent containing or consisting of an ether, a ketone, an ester, an alcohol, water, an (optionally halogenated) alkane, an (optionally halogenated) aromatic solvent or any mixtures thereof. The solvent may contain or consist of one or more of the following solvents: methanol, ethanol, isopropanol, 1-butanol, 2-butanol, isobutanol, tert-butanol, acetone, tetrahydrofuran, ethyl acetate, heptane, tert-butyl methyl ether, 1,2-dichloroethane, toluene, 2-butanone (MEK), tert-amyl alcohol, chloroform, xylene, and water.

In certain embodiments, the isolated precipitate containing the 14-hydroxymorphinone salt or solvate thereof is washed and/or (re)crystallized in a solvent consisting of an ether, an alcohol, water, chloroform, or any mixture thereof. In certain embodiments, said solvent may be methanol, ethanol, n-propanol, isopropanol, 1-butanol, 2-butanol, isobutanol, tert-butanol, acetone, tetrahydrofuran, chloroform, or a mixture of water with any of the foregoing.

In certain embodiments, the isolated precipitate containing the 14-hydroxymorphinone salt or solvate thereof is washed and/or (re)crystallized with a solvent which is tert-butyl methyl ether, tetrahydrofuran, methanol, ethanol, acetone, isopropanol, 2-butanol, or a mixture of methanol:water, THF:water, acetone:water, isopropanol:water, 2-butanol:water, or ethanol:water. In certain embodiments, the isolated precipitate containing the 14-hydroxymorphinone salt or solvate thereof is washed and/or (re)crystallized with a solvent which is tert-butyl methyl ether, tetrahydrofuran, methanol, a 2-butanol:water mixture, or a methanol:water mixture.

In certain embodiments, preferably wherein the 14-hydroxymorphinone salt is 14-hydroxymorphinone sulfate, the isolated precipitate containing the 14-hydroxymorphinone salt or solvate thereof is washed with and/or (re)crystallized in a 90:10 methanol:water mixture; 80:20 methanol:water mixture, 70:30 methanol:water or 60:40 methanol:water mixture. In certain embodiments, the isolated precipitate containing the 14-hydroxymorphinone salt or solvate thereof is washed with and/or (re)crystallized in a 80:20 or 70:30 methanol:water mixture. 8-Hydroxyoxymorphone (and its corresponding protonated species) is more soluble in these mixtures than 14-hydroxymorphinone sulfate and therefore it is assumed that 8-hydroxyoxymorphone may be removed from the isolated 14-hydroxymorphinone salt or solvate thereof by the washing and/or (re)crystallization.

In certain embodiments, preferably wherein the 14-hydroxymorphinone salt is 14-hydroxymorphinone sulfate, the isolated precipitate containing the 14-hydroxymorphinone salt or solvate thereof is washed with and/or (re)crystallized in a 90:10 ethanol:water mixture, 80:20 ethanol:water mixture or 70:30 ethanol:water mixture. In certain embodiments, the isolated precipitate containing the 14-hydroxymorphinone salt or solvate thereof is washed with and/or (re)crystallized in 90:10 ethanol/water mixture. 8-Hydroxyoxymorphone (and its corresponding protonated species) is more soluble in these mixtures than 14-hydroxymorphinone sulfate and therefore it is assumed that 8-hydroxyoxymorphonc may be removed from the isolated 14-hydroxymorphinone salt or solvate thereof by the washing and/or (re)crystallization.

In certain embodiments, preferably wherein the 14-hydroxymorphinone salt is 14-hydroxymorphinone sulfate, the isolated precipitate containing the 14-hydroxymorphinone salt or solvate thereof is washed with and/or (re)crystallized in tetrahydrofuran or in 90:10 tetrahydrofuran:water mixture. 8-Hydroxyoxymorphone (and its corresponding protonated species) is more soluble in these mixtures than 14-hydroxymorphinone sulfate and therefore it is assumed that 8-hydroxyoxymorphone may be removed from the isolated 14-hydroxymorphinone salt or solvate thereof by the washing and/or (re)crystallization.

In certain embodiments, preferably wherein the 14-hydroxymorphinone salt is 14-hydroxymorphinone sulfate, the isolated precipitate containing the 14-hydroxymorphinone salt or solvate thereof is washed with and/or (re)crystallized in a 90:10 isopropanol:water mixture, 80:20 isopropanol:water mixture or 70:30 isopropanol:water mixture. In certain embodiments, the isolated precipitate containing the 14-hydroxymorphinone salt or solvate thereof is washed with and/or (re)crystallized in a 90:10 isopropanol:water mixture. 8-Hydroxyoxymorphone (and its corresponding protonated species) is more soluble in these mixtures than 14-hydroxymorphinone sulfate and therefore it is assumed that 8-hydroxyoxymorphone may be removed from the isolated 14-hydroxymorphinone salt or solvate thereof by the washing and/or (re)crystallization.

In certain embodiments, preferably wherein the 14-hydroxymorphinone salt is 14-hydroxymorphinone sulfate, the isolated precipitate containing the 14-hydroxymorphinone salt or solvate thereof is washed with and/or (re)crystallized in a 90:10 2-butanol:water mixture, 80:20 2-butanol:water mixture, 70:30 2-butanol:water mixture, 60:40 2-butanol:water mixture, or 20:10 2-butanol:water mixture. In certain embodiments, the isolated precipitate containing the 14-hydroxymorphinone salt or solvate thereof is washed with and/or (re)crystallized in a 20:10 2-butanol:water mixture. 8-Hydroxyoxymorphone (and its corresponding protonated species) is more soluble in these mixtures than 14-hydroxymorphinone sulfate and therefore it is assumed that 8-hydroxyoxymorphone may be removed from the isolated 14-hydroxymorphinone salt or solvate thereof by the washing and/or (re)crystallization.

In certain embodiments, preferably wherein the 14-hydroxymorphinone salt is 14-hydroxymorphinone sulfate, the isolated precipitate containing the 14-hydroxymorphinone salt or solvate thereof is washed with and/or (re)crystallized in a 70:30 acetone:water mixture or 80:20 acetone:water mixture. 8-Hydroxyoxymorphone (and its corresponding protonated species) is more soluble in these mixtures than 14-hydroxymorphinone sulfate and therefore it is assumed that 8-hydroxyoxymorphone may be removed from the isolated 14-hydroxymorphinone salt or solvate thereof by the washing and/or (re)crystallization.

The washing of the isolated precipitate containing the 14-hydroxymorphinone salt or solvate thereof may be performed in any way conventional in the art, e.g., by forming a slurry of the compound.

In certain embodiments, the ratio of 8-hydroxyoxymorphone to 14-hydroxymorphinone in the supernatant after the precipitation of the 14-hydroxymorphinone salt or solvate thereof is higher than the ratio of 8-hydroxyoxymorphone to 14-hydroxymorphinone in the precipitate.

Preferred Process Conditions

A preferred set of reaction conditions for the oxidation process and the subsequent isolation of the 14-hydroxymorphinone salt is described in the following. Therein, the 14-hydroxymorphinone salt is preferably 14-hydroxymorphinone sulfate.

The process is performed by: (i) forming a solution or a suspension comprising the oripavine, from about 1.5 to about 2.0 mL water per g oripavine, and from about 2.5 to about 4.5 molar equivalents of formic acid per molar equivalent of oripavine, (ii) adding from about 0.5 to about 0.6 molar equivalents of sulfuric acid per molar equivalent of the oripavine to the solution or the suspension, (iii) adding from about 1.0 to about 1.4 molar equivalents, preferably from about 1.2 to about 1.4 molar equivalents, more preferably from about 1.2 to about 1.3 molar equivalents of hydrogen peroxide to the solution or the suspension from (ii), then incubating the mixture at a temperature of from about 30° C. to about 38° C., preferably of from about 32° C. to about 36° C., more preferably of about 35° C., until the conversion is complete, and (iv) precipitating the 14-hydroxymorphinone salt from the resulting solution or suspension. Step (iv) may be performed by adding a suitable anti solvent to the solution, as described in detail above. A preferred antisolvent may be an alcohol, in particular isopropanol or 2-butanol. Preferably, from about 2 to about 4 mL antisolvent per 1 g oripavine are added.

When the 14-hydroxymorphinone salt is 14-hydroxymorphinone sulfate, the process is preferably performed by: (i) forming a solution or a suspension by mixing the oripavine, from about 1.5 to about 2.0 mL water per g oripavine, and from about 2.5 to about 4.5 molar equivalents of formic acid per molar equivalent of oripavine, (ii) adding from about 0.5 to about 0.6 molar equivalents of sulfuric acid per molar equivalent of oripavine to the solution or the suspension, (iii) adding from about 1.0 to about 1.4 molar equivalents, preferably from about 1.2 to about 1.4 molar equivalents, more preferably from about 1.2 to about 1.3 molar equivalents of hydrogen peroxide to the solution or the suspension from (ii), then incubating the mixture at a temperature of from about 30° C. to about 38° C., preferably of from about 32° C. to about 36° C., more preferably of about 35° C., until the conversion is complete, and (iv) precipitating the 14-hydroxymorphinone sulfate from the resulting solution or suspension. Step (iv) may be performed by adding a suitable antisolvent to the solution, as described in detail above. A preferred antisolvent may be an alcohol, in particular isopropanol or 2-butanol. Preferably, from about 2 to about 4 mL antisolvent per 1 g oripavine are added.

In the oxidation process, the formation of the 14-hydroxymorphinone salt or a solvate thereof may have the effect that less 8-hydroxy compound is formed during the oxidation reaction in comparison to an oxidation reaction where no 14-hydroxymorphinone salt or solvate thereof is formed. In other words, the formation of the 14-hydroxymorphinone salt allows for an improvement of the by-product profile of the reaction product. One example for such oxidation reaction may be the formation of a 14-hydroxymorphinone salt wherein n is 2 and preferably wherein $X^{n-}$ is sulfate. Another example for such oxidation reaction may be the formation of a 14-hydroxymorphinone salt wherein n is 1 and preferably wherein $X^{n-}$ is trifluoroacetate.

The formation of the 14-hydroxymorphinone salt or a solvate thereof may also have the effect that 8-hydroxyoxymorphone can be separated from the 14-hydroxymorphinone salt or the solvate thereof, e.g., by precipitation of the 14-hydroxymorphinone salt or the solvate thereof from the reaction mixture. One example for such an effect may be the formation of a 14-hydroxymorphinone salt wherein $X^{n-}$ is sulfate. One example for such an effect may be the use of one of the antisolvents described in the present Section IV.

A combination of these effects may also take place. That is, both less 8-hydroxyoxymorphone is formed during the oxidation and said compound can be separated from the 14-hydroxymorphinone salt or solvate thereof. One example may be the formation of a 14-hydroxymorphinone salt wherein $X^{n-}$ is sulfate, preferably in combination with one of the antisolvents described in the present Section IV.

V. 14-Hydroxymorphinone Salt

The present invention uses a 14-hydroxymorphinone salt having the following formula or a solvate thereof

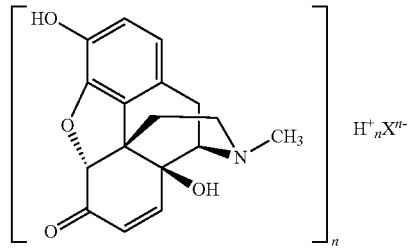

wherein $X^{n-}$ and n are defined as above, in particular in Section I, as starting material for the hydrogenation process according to the invention. Present invention may use said 14-hydroxymorphinone salt or solvate thereof as a solid, in solution or as a suspension.

The 14-hydroxymorphinone salt or solvate thereof comprises one or more protonated molecules of 14-hydroxymorphinone and at least one anion X. The anion may be an organic or inorganic anion. The anion may be mono- or polyvalent (e.g., divalent or trivalent). In its solid form, the components of the 14-hydroxymorphinone salt are present in stoichiometric amounts. However, other molecular ratios may also be present either in micro- or macrostructures of the salt, depending e.g., on the type of the anion and valency thereof, the solvent (which might also form part of the salt) and the ambient pH.

In certain embodiments, said 14-hydroxymorphinone salt or solvate thereof is provided in its isolated, solid form, which in certain embodiments is its crystalline form, as starting material for the hydrogenation reaction.

Said 14-hydroxymorphinone salt or solvate thereof may be obtainable or obtained by the process described in Section IV. Preferably, it is obtained by said process.

Said 14-hydroxymorphinone salt or solvate thereof is a starting material or intermediate for the hydrogenation reaction according to the present invention which results in the synthesis of oxymorphone or (pharmaceutically acceptable) salts or solvates thereof.

In certain embodiments of the 14-hydroxymorphinone salt or solvate thereof, n is 1 or 2, and is preferably 2.

In certain embodiments, $X^{n-}$ is $SO_4^{2-}$ or trifluoroacetate, and is preferably $SO_4^{2-}$.

In certain embodiments, the 14-hydroxymorphinone salt is provided as its solvate. Said solvate may be any association product of a 14-hydroxymorphinone salt with a solvent molecule. The molar ratio of solvent molecule(s) per molecule of 14-hydroxymorphinone salt may vary. The molar ratio of solvent to compound/salt in the solvate may be 1 (e.g., in a monohydrate), more than 1 (e.g., 2, 3, 4, 5 or 6 in a polyhydrate), or less than 1 (e.g., in a hemihydrate). The molar ratio need not be an integer ratio, it can also be, e.g., 0.5 (as in a hemihydrate) or 2.5. For example, 1 molecule water per molecule of 14-hydroxymorphinone sulfate is bound in 14-hydroxymorphinone sulfate monohydrate. The solvate of the 14-hydroxymorphinone salt is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate of the 14-hydroxymorphinone salt is a hydrate wherein the ratio of water per molecule is within the range of from 1 to 8. In certain embodiments, the solvate of the 14-hydroxymorphinone salt is a hydrate wherein the ratio of water per molecule is within the range of from 1 to 6, i.e. a mono- to hexahydrate. In certain embodiments, the solvate of the 14-hydroxymorphinone salt is a monohydrate or a pentahydrate.

In certain embodiments, the 14-hydroxymorphinone salt is

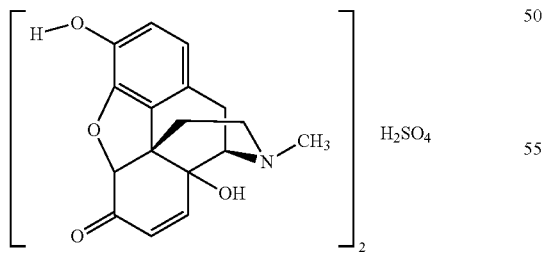

or a solvate thereof. The solvate may be a hydrate. The molar ratio of solvent to compound/salt in the solvate may be 1 (e.g., in a monohydrate), more than 1 (e.g., 2, 3, 4, 5 or 6 in a polyhydrate), or less than 1 (e.g., in a hemihydrate). The molar ratio need not be an integer ratio, it can also be, e.g., 0.5 (as in a hemihydrate) or 2.5. For example, 1 molecule water per molecule of 14-hydroxymorphinone sulfate is bound in 14-hydroxymorphinone sulfate monohydrate. The solvate is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate is a hydrate wherein the ratio of water per molecule is within the range of from 1 to 8. In certain embodiments, the solvate is a hydrate wherein the ratio of water per molecule is within the range of from 1 to 6, i.e. a mono- to hexahydrate. In certain embodiments, the solvate is a monohydrate or a pentahydrate.

Pharmaceutical compositions and dosage forms produced from said 14-hydroxymorphinone salt or solvate thereof, preferably, contain less 8-hydroxyoxymorphone and/or 14-hydroxymorphinone than pharmaceutical compositions prepared via a different intermediate, i.e. without the 14-hydroxymorphinone salt.

In certain embodiments, the 14-hydroxymorphinone salt is prepared as described in Section IV.

In certain embodiments, the 14-hydroxymorphinone salt or solvate thereof additionally comprises 8-hydroxyoxymorphone.

Said 8-hydroxyoxymorphone is a by-product of the oxidation reaction described above, as illustrated in the following reaction Scheme 17:

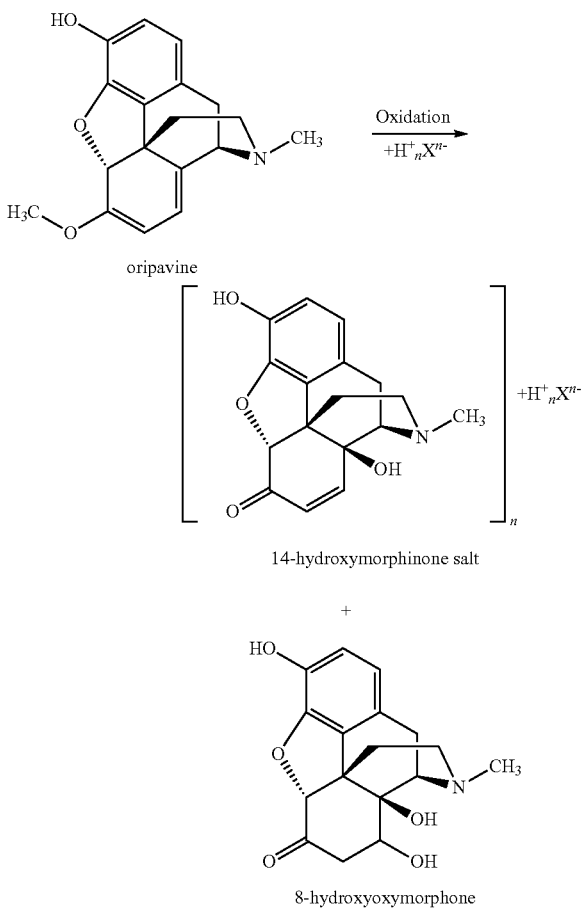

Said 8-hydroxyoxymorphone may be present in the form of its free base, or in the form of its salt or solvate.

Whenever 8-hydroxyoxymorphone is comprised in the 14-hydroxymorphinone salt (thus forming a composition), it is present in a certain amount which shall be specified in the following.

In certain embodiments, the amount of the 8-hydroxyoxymorphone or salt or solvate thereof in the 14-hydroxymorphinone salt or solvate thereof is less than about 2500 ppm, less than about 2250 ppm, less than about 2000 ppm, less than about 1750 ppm, less than about 1500 ppm, or less than about 1250 ppm of the 14-hydroxymorphinone salt (HPLC peak area ratio).

In certain embodiments, the amount of the 8-hydroxyoxymorphone or salt or solvate thereof in the 14-hydroxymorphinone salt or solvate thereof is less than about 1000 ppm, less than about 750 ppm, less than about 500 ppm, or less than about 400 ppm of the 14-hydroxymorphinone salt or solvate thereof (HPLC peak area ratio).

In certain embodiments, the amount of the 8-hydroxyoxymorphone or salt or solvate thereof in the 14-hydroxymorphinone salt or solvate thereof is less than about 300 ppm, less than about 275 ppm, less than about 250 ppm, less than about 225 ppm, less than about 200 ppm, less than about 175 ppm, less than about 150 ppm, or less than about 125 ppm of the 14-hydroxymorphinone salt or solvate thereof (HPLC peak area ratio).

In certain embodiments, the amount of the 8-hydroxyoxymorphone or salt or solvate thereof in the 14-hydroxymorphinone salt or solvate thereof is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm of the 14-hydroxymorphinone salt or solvate thereof (HPLC peak area ratio).

In certain embodiments, the amount of the 8-hydroxyoxymorphone or salt or solvate thereof in the 14-hydroxymorphinone salt or solvate thereof is less than about 10 ppm, less than about 8 ppm, less than about 6 ppm, less than about 4 ppm, or less than about 2 ppm of the 14-hydroxymorphinone salt or solvate thereof (HPLC peak area ratio).

In certain embodiments, the amount of the 8-hydroxyoxymorphone or salt or solvate thereof in the 14-hydroxymorphinone salt or solvate thereof is less than about 1 ppm, less than about 0.8 ppm, less than about 0.6 ppm, less than about 0.4 ppm, less than about 0.3 ppm, less than about 0.2 ppm, or less than about 0.1 ppm of the 14-hydroxymorphinone salt or solvate thereof (e.g., the amount of 8-hydroxyoxymorphone is from about 0.05 ppm to about 0.7 ppm of the 14-hydroxymorphinone sulfate) (HPLC peak area ratio).

In certain embodiments, the 14-hydroxymorphinone salt or solvate thereof does not contain 8-hydroxyoxymorphone.

In certain embodiments, the 14-hydroxymorphinone salt is 14-hydroxymorphinone sulfate, and the amount of 8-hydroxyoxymorphone therein is less than about 300 ppm, less than about 275 ppm, less than about 250 ppm, less than about 225 ppm, less than about 200 ppm, less than about 175 ppm, less than about 150 ppm, less than about 125 ppm, less than about 100 ppm, less than about 80 ppm, less than about 60 ppm, less than about 40 ppm, less than about 30 ppm, or less than about 20 ppm of the 14-hydroxymorphinone sulfate (HPLC peak area ratio). In certain embodiments, it is less than about 10 ppm, less than about 8 ppm, less than about 6 ppm, less than about 4 ppm, less than about 2 ppm, less than about 1 ppm, less than about 0.8 ppm, less than about 0.6 ppm, less than about 0.4 ppm, less than about 0.3 ppm, less than about 0.2 ppm, or less than about 0.1 ppm of the 14-hydroxymorphinone sulfate (HPLC peak area ratio).

In certain embodiments, the 14-hydroxymorphinone sulfate does not contain 8-hydroxyoxymorphone.

In certain embodiments, the amount of the 8-hydroxyoxymorphone or salt or solvate thereof in the 14-hydroxymorphinone salt or solvate thereof has a lower limit of about 0.01 ppm of the 14-hydroxymorphinone salt or solvate thereof (HPLC peak area ratio). In certain embodiments, the lower limit is about 0.05 ppm, 0.1 ppm, about 0.3 ppm, about 0.5 ppm, about 0.7 ppm, about 1 ppm, about 1.5 ppm, about 2 ppm, or about 3 ppm. For example, the amount of the 8-hydroxyoxymorphone or salt or solvate thereof in the 14-hydroxymorphinone salt or solvate thereof may range from about 0.05 ppm to 1 ppm in a certain embodiment, and from about 1 ppm to about 10 ppm in a certain other embodiment.

The 14-hydroxymorphinone salt or solvate thereof in certain embodiments comprises from about 0.01 ppm to about 2500 ppm, from about 0.05 to about 2250 ppm, from about 0.1 ppm to about 2000 ppm, from about 0.3 to about 1750 ppm, from about 0.5 ppm to about 1500 ppm, or from about 1 ppm to about 1250 ppm 8-hydroxyoxymorphone or a salt or solvate thereof in relation to the 14-hydroxymorphinone salt (HPLC peak area ratio).

The 14-hydroxymorphinone salt or solvate thereof in certain embodiments comprises from about 0.05 ppm to about 1000 ppm, from about 0.1 ppm to about 800 ppm, from about 0.1 ppm to about 700 ppm, from about 0.2 ppm to about 600 ppm, from about 0.3 ppm to about 500 ppm, or from about 0.5 ppm to about 400 ppm 8-hydroxyoxymorphone or salt or solvate thereof in relation to the 14-hydroxymorphinone salt.

The 14-hydroxymorphinone salt or solvate thereof in certain embodiments comprises from about 0.05 ppm to about 350 ppm, from about 0.1 ppm to about 300 ppm, from about 0.2 ppm to about 275 ppm, from about 0.3 ppm to about 250 ppm, from about 0.4 ppm to about 225 ppm, or from about 0.5 ppm to about 200 ppm 8-hydroxyoxymorphone or salt or solvate thereof in relation to the 14-hydroxymorphinone salt.

The 14-hydroxymorphinone salt may comprise the 8-hydroxyoxymorphone as (i) 8α isomer, (ii) 8β isomer or (iii) a combination of 8α and 8β isomer. Preferably, at least a portion of the 8-hydroxyoxymorphone is the 8α isomer.

Preferably, the 14-hydroxymorphinone salt is 14-hydroxymorphinone sulfate.

VI. Oxymorphone

Present invention further provides oxymorphone or a salt or solvate thereof, which is obtainable or preferably has been obtained by the hydrogenation process according to the present invention.

The salt or solvate of the oxymorphone may be a pharmaceutically acceptable salt or solvate. Such salts or solvates are known in the art.

The oxymorphone according to the present invention is preferably in its free base form or in the form of a solvate thereof.

The oxymorphone according to the present invention may be comprised in a composition, which may be a solid or a liquid. Said composition may the product of the hydrogenation process according to the present invention.

In certain embodiments, the oxymorphone is a solid. In certain embodiments, it is the precipitate containing the oxymorphone base as described as product of the hydrogenation process described in Section II.

The oxymorphone or the (optionally pharmaceutically acceptable) salt or solvate thereof in certain embodiments comprises 8-hydroxyoxymorphone.

Preferably, the oxymorphone or the (optionally pharmaceutically acceptable) salt or solvate thereof contains less than about 5 ppm, more preferably less than about 3 ppm, even more preferably less than about 1 ppm 8-hydroxyoxymorphone (HPLC peak area ratio). Most preferably, it does not contain 8-hydroxyoxymorphone in detectable amounts, and even may not contain any 8-hydroxyoxymorphone at all.

In certain embodiments, the amount of the 8-hydroxyoxymorphone or salt or solvate thereof in the oxymorphone or the (optionally pharmaceutically acceptable) salt or solvate thereof is less than about 2500 ppm, less than about 2250 ppm, less than about 2000 ppm, less than about 1750 ppm, less than about 1500 ppm, or less than about 1250 ppm of the oxymorphone or salt or solvate thereof (HPLC peak area ratio).

In certain embodiments, the amount of the 8-hydroxyoxymorphone or salt or solvate thereof in the oxymorphone or the (optionally pharmaceutically acceptable) salt or solvate thereof is less than about 1000 ppm, less than about 750 ppm, less than about 500 ppm, or less than about 400 ppm of the oxymorphone or salt or solvate thereof (HPLC peak area ratio).

In certain embodiments, the amount of the 8-hydroxyoxymorphone or salt or solvate thereof in the oxymorphone or the (optionally pharmaceutically acceptable) salt or solvate thereof is less than about 300 ppm, less than about 275 ppm, less than about 250 ppm, less than about 225 ppm, less than about 200 ppm, less than about 175 ppm, less than about 150 ppm, or less than about 125 ppm of the oxymorphone or salt or solvate thereof (HPLC peak area ratio).

In certain embodiments, the amount of the 8-hydroxyoxymorphone or salt or solvate thereof in the oxymorphone or the (optionally pharmaceutically acceptable) salt or solvate thereof is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm of the oxymorphone or salt or solvate thereof (HPLC peak area ratio).

In certain embodiments, the amount of the 8-hydroxyoxymorphone or salt or solvate thereof in the oxymorphone or the (optionally pharmaceutically acceptable) salt or solvate thereof is less than about 10 ppm, less than about 8 ppm, less than about 6 ppm, less than about 4 ppm, or less than about 2 ppm of the oxymorphone or salt or solvate thereof (HPLC peak area ratio).

In certain embodiments, the amount of the 8-hydroxyoxymorphone or salt or solvate thereof in the oxymorphone or the (optionally pharmaceutically acceptable) salt or solvate thereof is less than about 1 ppm, less than about 0.8 ppm, less than about 0.6 ppm, less than about 0.4 ppm, less than about 0.3 ppm, less than about 0.2 ppm, or less than about 0.1 ppm of the oxymorphone or salt or solvate thereof (e.g., the amount of 8-hydroxyoxymorphone is from about 0.1 ppm to about 0.7 ppm of the 14-hydroxymorphinone sulfate) (HPLC peak area ratio).

In certain embodiments, the oxymorphone or the (optionally pharmaceutically acceptable) salt or solvate thereof does not contain 8-hydroxyoxymorphone in detectable amounts, or not contain any 8-hydroxyoxymorphone.

In certain embodiments, the amount of the 8-hydroxyoxymorphone or salt or solvate thereof in the oxymorphone or the (optionally pharmaceutically acceptable) salt or solvate thereof has a lower limit of about 0.05 ppm of the oxymorphone or salt or solvate thereof (HPLC peak area ratio). In certain embodiments, the lower limit is about 0.1 ppm, about 0.3 ppm, about 0.5 ppm, about 0.7 ppm, about 1 ppm, about 1.5 ppm, about 2 ppm, or about 3 ppm. For example, the amount of the 8-hydroxyoxymorphone or salt or solvate thereof in the composition may range from about 0.05 ppm to 1 ppm in a certain embodiment, and from about 1 ppm to about 10 ppm in a certain other embodiment.

In certain embodiments, the amount of 8-hydroxyoxymorphone or salt or solvate thereof in the oxymorphone or the salt or solvate thereof is less than about 300 ppm, less than about 275 ppm, less than about 250 ppm, less than about 225 ppm, less than about 200 ppm, less than about 175 ppm, less than about 150 ppm, less than about 125 ppm, less than about 100 ppm, less than about 80 ppm, less than about 60 ppm, less than about 40 ppm, less than about 30 ppm, or less than about 20 ppm of the oxymorphone (HPLC peak area ratio). In certain embodiments, it is less than about 10 ppm, less than about 8 ppm, less than about 6 ppm, less than about 4 ppm, less than about 2 ppm, less than about 1 ppm, less than about 0.8 ppm, less than about 0.6 ppm, less than about 0.4 ppm, less than about 0.3 ppm, less than about 0.2 ppm, or less than about 0.1 ppm of the oxymorphone (HPLC peak area ratio). In certain embodiments, the oxymorphone does not contain 8-hydroxyoxymorphone.

In certain embodiments, the oxymorphone or the (optionally pharmaceutically acceptable) salt or solvate thereof comprises from about 0.05 ppm to about 2500 ppm, from about 0.05 to about 2250 ppm, from about 0.1 ppm to about 2000 ppm, from about 0.3 to about 1750 ppm, from about 0.5 ppm to about 1500 ppm, or from about 1 ppm to about 1250 ppm 8-hydroxyoxymorphone or a salt or solvate thereof in relation to the oxymorphone or salt or solvate thereof (HPLC peak area ratio).

In certain embodiments, the oxymorphone or the (optionally pharmaceutically acceptable) salt or solvate thereof comprises from about 0.05 ppm to about 1000 ppm, from about 0.1 ppm to about 800 ppm, from about 0.1 ppm to about 700 ppm, from about 0.2 ppm to about 600 ppm, from about 0.3 ppm to about 500 ppm, or from about 0.5 ppm to about 400 ppm 8-hydroxyoxymorphone or salt or solvate thereof in relation to the oxymorphone or salt or solvate thereof.

In certain embodiments, the oxymorphone or the (optionally pharmaceutically acceptable) salt or solvate thereof comprises from about 0.05 ppm to about 350 ppm, from about 0.1 ppm to about 300 ppm, from about 0.2 ppm to about 275 ppm, from about 0.3 ppm to about 250 ppm, from about 0.4 ppm to about 225 ppm, or from about 0.5 ppm to about 200 ppm 8-hydroxyoxymorphone or salt or solvate thereof in relation to compound IV or salt or solvate thereof.

Additionally, the composition comprising the oxymorphone or the (optionally pharmaceutically acceptable) salt or solvate thereof in certain embodiments comprises 14-hydroxymorphinone.

Preferably, the oxymorphone or the (optionally pharmaceutically acceptable) salt or solvate thereof contains less than about 5 ppm, more preferably less than about 3 ppm, even more preferably less than about 1 ppm 14-hydroxymorphinone (HPLC peak area ratio). Most preferably, it does not contain 14-hydroxymorphinone in detectable amounts, and even may not contain any 14-hydroxymorphinone at all.

The amount of the 14-hydroxymorphinone or salt or solvate thereof in relation to the amount of the oxymorphone or salt or solvate thereof may in certain embodiments be less than about 500 ppm, less than about 250 ppm, less than about 200 ppm, less than about 100 ppm, less than about 50 ppm or less than about 40 ppm (HPLC peak area ratio). In certain embodiments, it may be less than about 30 ppm, less than about 25 ppm, less than about 20 ppm, less than about 15 ppm, less than about 10 ppm, less than about 5 ppm, or less than about 2.5 ppm (HPLC peak area ratio). In certain embodiments, it may be less than about 1 ppm, less than about 0.8 ppm, less than about 0.6 ppm, less than about 0.6 ppm, less than about 0.4 ppm, less than about 0.2 ppm, or less than about 0.1 ppm (HPLC peak area ratio). In certain embodiments, the oxymorphone or the (optionally pharmaceutically acceptable) salt or solvate thereof does not contain 14-hydroxymorphinone (in detectable amounts).

In certain embodiments, the amount of the 14-hydroxymorphinone or salt or solvate thereof in the oxymorphone or the (optionally pharmaceutically acceptable) salt or solvate thereof has a lower limit of about 0.05 ppm of the oxymorphone or salt or solvate thereof (HPLC peak area ratio). In certain embodiments, the lower limit is about 0.1 ppm, about 0.3 ppm, about 0.5 ppm, about 0.7 ppm, about 1 ppm, about 1.5 ppm, about 2 ppm, or about 3 ppm. For example, the amount of the 14-hydroxymorphinone or salt or solvate thereof in the oxymorphone or the (optionally pharmaceutically acceptable) salt or solvate thereof may range from about 0.05 ppm to 1 ppm in a certain embodiment, and from about 1 ppm to about 10 ppm in a certain other embodiment.

The oxymorphone or the (optionally pharmaceutically acceptable) salt or solvate thereof in certain embodiments comprises from about 0.05 ppm to about 500 ppm, from about 0.05 ppm to about 250 ppm, from about 0.05 ppm to about 200 ppm, from about 0.05 ppm to about 100 ppm, from about 0.05 ppm to about 50 ppm, from about 0.05 ppm to about 25 ppm, from about 0.05 ppm to about 10 ppm, from about 0.05 ppm to about 5 ppm, or from about 0.05 ppm to about 1 ppm 14-hydroxymorphinone or salt or solvate thereof in relation to oxymorphone or the salt or solvate thereof.

In certain embodiments, the amount of the 14-hydroxymorphinone in relation to the amount of the oxymorphone in the oxymorphone or the salt or solvate thereof is less than about 200 ppm, less than about 175 ppm, less than about 150 ppm, less than about 125 ppm, less than about 100 ppm, less than about 80 ppm, less than about 60 ppm, less than about 40 ppm, less than about 30 ppm, less than about 20 ppm, or less than about 10 ppm, or less than about 5 ppm of the oxymorphone (HPLC peak area ratio). In certain embodiments, the oxymorphone or the (optionally pharmaceutically acceptable) salt or solvate thereof does not contain 14-hydroxymorphinone or a salt or solvate thereof.

The oxymorphone or salt or solvate thereof may also additionally comprise a combination of 14-hydroxymorphinone with 8-hydroxyoxymorphone, preferably within the limits for the single compounds 8-hydroxyoxymorphone and 14-hydroxymorphinone as described in the preceding paragraphs.

In certain embodiments, the oxymorphone or the (optionally pharmaceutically acceptable) salt or solvate thereof additionally comprises both 14-hydroxymorphinone and 8-hydroxyoxymorphone. In certain embodiments, the oxymorphone or the (optionally pharmaceutically acceptable) salt or solvate thereof comprises a combined amount of 14-hydroxymorphinone and 8-hydroxyoxymorphone which is less than about 1000 ppm, less than about 750 ppm, less than about 500 ppm, less than about 400 ppm, less than about 300 ppm, or less than about 275 ppm in relation to the amount of the oxymorphone (HPLC peak area ratio).

In certain embodiments, the combined amount of the compound 14-hydroxymorphinone and 8-hydroxyoxymorphone in the oxymorphone or the (optionally pharmaceutically acceptable) salt or solvate thereof is less than about 250 ppm, less than about 225 ppm, less than about 200 ppm, less than about 175 ppm, less than about 150 ppm, or less than about 125 ppm in relation to the amount of the oxymorphone (HPLC peak area ratio).

In certain embodiments, the combined amount of the 14-hydroxymorphinone and 8-hydroxyoxymorphone in the oxymorphone or the (optionally pharmaceutically acceptable) salt or solvate thereof is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm in relation to the amount of the oxymorphone (HPLC peak area ratio).

In certain embodiments, the combined amount of the 14-hydroxymorphinone and 8-hydroxyoxymorphone in the oxymorphone or the (optionally pharmaceutically acceptable) salt or solvate thereof is less than about 10 ppm, less than about 8 ppm, less than about 6 ppm, less than about 4 ppm, or less than about 2 ppm in relation to the amount of the oxymorphone (HPLC peak area ratio).

In certain embodiments, the combined amount of the 14-hydroxymorphinone and 8-hydroxyoxymorphone in the oxymorphone or the (optionally pharmaceutically acceptable) salt or solvate thereof is less than about 1 ppm, less than about 0.8 ppm, less than about 0.6 ppm, less than about 0.4 ppm, less than about 0.3 ppm, less than about 0.2 ppm, or less than about 0.1 ppm in relation to the amount of the oxymorphone (HPLC peak area ratio).

In certain embodiments, the oxymorphone or the (optionally pharmaceutically acceptable) salt or solvate thereof does not contain 14-hydroxymorphinone and 8-hydroxyoxymorphone (in detectable amounts).

Preferably, the oxymorphone or the (optionally pharmaceutically acceptable) salt or solvate thereof contains less than about 10 ppm, more preferably less than about 6 ppm, even more preferably less than about 4 ppm combined 14-hydroxymorphinone and 8-hydroxyoxymorphone (HPLC peak area ratio). Most preferably, it does not contain 14-hydroxymorphinone and 8-hydroxyoxymorphone in detectable amounts, and even may not contain any 14-hydroxymorphinone and 8-hydroxyoxymorphone at all.

In certain embodiments, the combined amount of the 14-hydroxymorphinone and 8-hydroxyoxymorphone in the oxymorphone or the (optionally pharmaceutically acceptable) salt or solvate thereof has a lower limit of about 0.05 ppm of the oxymorphone (HPLC peak area ratio). In certain embodiments, the lower limit is about 0.1 ppm, about 0.3 ppm, about 0.5 ppm, about 0.7 ppm, about 1 ppm, about 1.5 ppm, about 2 ppm, or about 3 ppm in relation to the amount of the oxymorphone (HPLC peak area ratio).

In certain embodiments, the oxymorphone or the (optionally pharmaceutically acceptable) salt or solvate thereof comprises less than about 200 ppm, less than about 100 ppm, less than about 50 ppm, less than about 25 ppm, less than about 20 ppm, less than about 15 ppm, or less than about 10 ppm of 14-hydroxymorphinone or a salt or solvate thereof, and/or less than about 300 ppm, less than about 200 ppm, less than about 100 ppm, less than about 50 ppm, less than about 25 ppm, or less than about 10 ppm of 8-hydroxyoxymorphone or a salt or solvate thereof.

In certain embodiments, the oxymorphone or the (optionally pharmaceutically acceptable) salt or solvate thereof comprises less than about 25 ppm, less than about 20 ppm, less than about 15 ppm, less than about 10 ppm, less than about 5 ppm, or less than about 1 ppm of 14-hydroxymorphinone or a salt or solvate thereof, and/or less than about 100 ppm, less than about 50 ppm, less than about 25 ppm, less than about 10 ppm, or less than about 5 ppm of 8-hydroxyoxymorphone or a salt or solvate thereof.

In certain embodiments, the oxymorphone or the (optionally pharmaceutically acceptable) salt or solvate thereof comprises less than about 10 ppm, less than about 5 ppm, less than about 4 ppm, less than about 3 ppm, less than about 2 ppm, less than about 1 ppm, or less than about 0.5 ppm of 14-hydroxymorphinone or a salt or solvate thereof, and/or less than about 10 ppm, less than about 5 ppm, less than about 3 ppm, less than about 2 ppm, less than about 1 ppm, or less than about 0.5 ppm of 8-hydroxyoxymorphone or a salt or solvate thereof.

In certain embodiments, the oxymorphone or a salt or solvate thereof additionally comprises (i) 8-hydroxyoxymorphone or a salt or solvate thereof, and/or (ii) 14-hydroxymorphinone or a salt or solvate thereof, wherein the amount of the 8-hydroxyoxymorphone is less than about 300 ppm, less than about 275 ppm, less than about 250 ppm, less than about 225 ppm, less than about 200 ppm, less than about 175 ppm, less than about 150 ppm, less than about 125 ppm, less than about 100 ppm, less than about 80 ppm, less than about 60 ppm, less than about 40 ppm, less than about 30 ppm, less than about 20 ppm, less than about 10 ppm, less than about 8 ppm, less than about 6 ppm, less than about 4 ppm, less than about 2 ppm, less than about 1 ppm, less than about 0.8 ppm, less than about 0.6 ppm, less than about 0.4 ppm, less than about 0.3 ppm, less than about 0.2 ppm, or less than about 0.1 ppm of the oxymorphone (HPLC peak area ratio; e.g., from about 0.2 ppm to about 50 ppm of the oxymorphone), and the amount of the 14-hydroxymorphinone is less than about 200 ppm, less than about 175 ppm, less than about 150 ppm, less than about 125 ppm, less than about 100 ppm, less than about 80 ppm, less than about 60 ppm, less than about 40 ppm, less than about 30 ppm, less than about 20 ppm, or less than about 10 ppm, or less than about 5 ppm of the oxymorphone (HPLC peak area ratio; e.g., from about 0.1 ppm to about 15 ppm, or from about 0.2 ppm to about 2 ppm of the oxymorphone). In preferred embodiments, the oxymorphone is oxymorphone free base.

In certain embodiments, the oxymorphone is oxymorphone free base and additionally comprises (i) 8-hydroxyoxymorphone or a salt or solvate thereof, and/or (ii) 14-hydroxymorphinone or a salt or solvate thereof, wherein the amount of the 8-hydroxyoxymorphone is less than about 100 ppm, less than about 80 ppm, less than about 60 ppm, less than about 40 ppm, less than about 30 ppm, less than about 20 ppm, less than about 10 ppm, less than about 5 ppm, or less than about 2 ppm of the oxymorphone salt (HPLC peak area ratio; e.g., from about 0.1 ppm to about 9 ppm of the oxymorphone salt), and the amount of the 14-hydroxymorphinone is less than about 50 ppm, less than about 25 ppm, less than about 10 ppm, less than about 5 ppm, or less than about 2 ppm of the oxymorphone salt (HPLC peak area ratio).

VII. Use of the Oxymorphone

VII-A. Use in a Medicament

Oxymorphone or a pharmaceutically acceptable salt or solvate thereof can be used as API of a medicament. To date, the API form of oxymorphone is oxymorphone hydrochloride.

For this use, the oxymorphone or the pharmaceutically acceptable salt or solvate thereof may be the oxymorphone as described in Section VI.

For this use, the oxymorphone or the pharmaceutically acceptable salt or solvate thereof may be used in a dosage form as described in Section VIII.

In the context of the present invention, the oxymorphone is preferably prepared as its free base according to the process of the present invention, and then used either directly as API, or converted into a pharmaceutically acceptable salt or solvate which is then used as API, in particular, oxymorphone hydrochloride.

For this use, the medicament may be for treating a medical condition selected from the group consisting of pain, addiction, cough, constipation, diarrhea, insomnia associated with and/or caused by pain, cough or addiction, depression associated with and/or resulting from pain, cough or addiction, or a combination of two or more of the foregoing conditions. In particular, said condition may be pain.

The present invention also provides a method for treating an animal, preferably a mammal (e.g., a human), (in the following: "a patient") using the oxymorphone or a pharmaceutically acceptable salt or solvate thereof. Said treatment may be of any medical condition which is conventionally treated by administration of oxymorphone or a pharmaceutically acceptable salt or solvate thereof to a patient.

Said medical condition may be pain, addiction, cough, constipation, diarrhea, insomnia associated with and/or caused by pain, cough or addiction, depression associated with and/or resulting from pain, cough or addiction, or a combination of two or more of the foregoing conditions. In particular, said condition may be pain.

For this method of treatment, the oxymorphone or the pharmaceutically acceptable salt or solvate thereof may be the compound as described in Section VI.

For this method of treatment, the oxymorphone or the pharmaceutically acceptable salt or solvate thereof may be used in a dosage form as described in Section VIII.

VII-B. Other Uses

The oxymorphone (prepared) according to the present invention or an (optionally pharmaceutically acceptable) salt or solvate thereof may also be used as follows:

In certain embodiments, the oxymorphone or (optionally pharmaceutically acceptable) salt or solvate thereof is used as an intermediate or starting material for preparing the oxymorphone in its free base form or for preparing another salt or solvate of oxymorphone, e.g., for preparing a(nother) pharmaceutically acceptable salt or solvate of oxymorphone. For example, the oxymorphone may be used for preparing oxymorphone hydrochloride. Processes for preparing said other salt or solvate which involve a process or compound as described above in the detailed description are also embodiments of the present invention.

In certain embodiments, the oxymorphone or (optionally pharmaceutically acceptable) salt or solvate thereof is used as an intermediate or starting material for preparing another opioid or a pharmaceutically acceptable salt or solvate thereof or a prodrug thereof, and/or for preparing a medicament containing the oxymorphone or a pharmaceutically acceptable salt or solvate thereof, or containing another opioid or a pharmaceutically acceptable salt or solvate thereof. For example, oxymorphone may be used as starting material for preparing oxycodone, naloxone, noroxymorphone, naltrexone, methyl naltrexone, nalmafine, or nalfurafine. Processes for preparing said other opioids which involve a process or compound as described above in the detailed description are also embodiments of the present invention.

VIII. Dosage Forms

Dosage forms in accordance with the present invention comprise one or more of the compounds described above and one or more pharmaceutically acceptable excipients. The dosage forms may or may not be abuse-resistant.

Those compounds, salts or solvates according to the present invention which are or contain an active pharmaceutical ingredient, in particular the oxymorphone which is described in Section VI, the pharmaceutically acceptable salts and solvates thereof, can be comprised in a pharmaceutical dosage form or medicament. Other opioids made from compounds, salts or solvates according to the present invention can also be comprised in a pharmaceutical dosage form or medicament. Prodrugs of the opioids described herein can also be comprised in a pharmaceutical dosage form or medicament. Such dosage forms and medicaments are also an embodiment of the present invention.

In addition to said active pharmaceutical ingredient, said dosage forms comprise one or more pharmaceutically acceptable excipients.

A pharmaceutical dosage form of the present invention may comprise (i) an opioid prepared according to present invention or a pharmaceutically acceptable salt or solvate thereof, and (ii) one or more pharmaceutically acceptable excipients. In particular, a pharmaceutical dosage form of the present invention may comprise (i) oxymorphone or an oxymorphone salt or solvate as described above, and (ii) one or more pharmaceutically acceptable excipients.

In certain embodiments, the dosage form comprises oxymorphone or a pharmaceutically acceptable salt or solvate thereof, wherein said compounds have the properties as described in Section VI and/or have been prepared according to a process of the present invention. In one embodiment, the oxymorphone salt is oxymorphone hydrochloride.

In certain embodiments, the dosage form comprises a combination of oxymorphone or a salt or solvate thereof which has the properties as described in Section VI and/or has been prepared according to a process of the present invention, with another opioid. In certain embodiments, the dosage form comprises a combination of oxymorphone or a salt or solvate thereof which has the properties as described in Section VI and/or has been prepared according to a process of the present invention, with an opioid receptor antagonist. For example, a dosage form of the present invention may comprise a combination of oxymorphone or a pharmaceutically acceptable salt or solvate thereof (such as oxymorphone hydrochloride) and naloxone or a pharmaceutically acceptable salt or solvate (such as naloxone hydrochloride).

In certain embodiments, the dosage form is selected from the group consisting of oral dosage forms (e.g., tablets, capsules, suspensions, solutions, etc.), injectable dosage forms, rectal dosage forms (e.g., suppositories), and transdermal dosage forms (e.g., patches).

In certain embodiments, the pharmaceutical composition or dosage form does not contain 14-hydroxymorphinone and/or 8-hydroxyoxymorphone. Preferably, neither 14-hydroxymorphinone nor 8-hydroxyoxymorphone are contained.

In said embodiments, the dosage form may be selected from the group consisting of oral dosage forms (e.g., tablets, capsules, suspensions, solutions, etc.), injectable dosage forms, rectal dosage forms (e.g., suppositories), and transdermal dosage forms (e.g., patches). Dosage forms for oral administration may be presented as tablets, capsules, liquid formulations, troches, lozenges, powders, granules, microparticles (e.g., microcapsules, microspheres and the like), or buccal tablets.

In certain embodiments, oral dosage forms of the present invention may be in the form of tablets (sustained release and/or immediate release), solutions, suspensions, etc.

Oral dosage forms can provide a controlled release (sustained release or delayed release) or an immediate release of the active pharmaceutical ingredient. One of the conventional excipients may be a pharmaceutically acceptable carrier. Suitable pharmaceutically acceptable carriers include hut are not limited to, e.g., alcohols, gum arabic, vegetable oils, benzyl alcohols, polyethylene glycols, gelate, carbohydrates such as lactose, amylose or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, etc. The dosage form may further comprise an inert diluent such as lactose; granulating and disintegrating agents such as cornstarch; binding agents such as starch; and lubricating agents such as magnesium stearate. The tablets may be uncoated or they may be coated by known techniques for elegance or to provide a controlled release of the drug (a sustained release, a delayed release or a pulsatile release) of the pharmaceutical composition.

The pharmaceutical preparations can be sterilized and if desired mixed with auxiliary agents, e.g., lubricants, disintegrants, preservatives, stabilizers, wetting agents, emulsifiers, salts for influencing osmotic pressure buffers, coloring, flavoring and/or aromatic substances and the like.

The compositions intended for oral use may be prepared according to any method known in the art and such compositions may contain one or more agents selected from the group consisting of inert, non-toxic pharmaceutically acceptable excipients which are suitable for the manufacture of the pharmaceutically acceptable dosage forms.

In certain embodiments, the sustained release dosage form may optionally comprise particles containing an opioid pharmaceutical composition described above. In certain embodiments, the particles have a diameter from about 0.1 mm to about 2.5 mm, preferably from about 0.5 mm to about 2 mm. The particles may be film coated with a material that permits release of the active at a sustained rate in an aqueous medium. The film coat may be chosen so as to achieve, in combination with the other ingredients of the dosage form, desired release properties. The sustained release coating formulations of the present invention should be capable of producing a strong, continuous film that is smooth and elegant, capable of supporting pigments and other coating additives, non-toxic, inert, and tack-free.

Coated Beads

In certain embodiments of the present invention a hydrophobic material is used to coat inert pharmaceutical beads such as nu pariel 18/20 beads, and a plurality of the resultant solid sustained release beads may thereafter be placed in a gelatin capsule in an amount sufficient to provide an effective sustained release dose of the opioid pharmaceutical composition when ingested and contacted by an environmental fluid, e.g., gastric fluid or dissolution media.

The sustained release bead formulations of the present invention slowly release the active of the present invention, e.g., when ingested and exposed to gastric fluids, and then to intestinal fluids.

The sustained release profile of the formulations of the invention can be altered, for example, by varying the amount of overcoating with the hydrophobic material, altering the manner in which a plasticizer is added to the hydrophobic material, by varying the amount of plasticizer relative to hydrophobic material, by the inclusion of additional ingredients or excipients, by altering the method of manufacture, etc.

The dissolution profile of the ultimate product may also be modified, for example, by increasing or decreasing the thickness of the retardant coating.

Spheroids or beads coated with the agent(s) of the present invention are prepared, e.g., by dissolving the pharmaceutical compositions in water and then spraying the solution onto a substrate, for example, nu pariel 18/20 beads, using a Wurster insert. Optionally, additional ingredients may be added prior to coating the beads in order to assist the binding of the pharmaceutical compositions to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the active(s) from the hydrophobic sustained release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g., triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the agent(s) by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined sustained release of the pharmaceutical composition when the coated substrate is exposed to aqueous solutions, e.g., gastric fluid, may be applied. After coating with the hydrophobic material, a further overcoat of a film-former, such as, e.g., Opadry®, may be optionally applied to the beads. This overcoat is provided, if at all, e.g., in order to substantially reduce agglomeration of the beads.

The release of the pharmaceutical composition(s) from the sustained release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in an environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semi-permeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,899; 4,063,064; and 4,088,864.

Matrix Formulations

In other embodiments of the present invention, the sustained release formulation is achieved via a sustained release matrix optionally having a sustained release coating as set forth herein. The materials suitable for inclusion in the sustained release matrix may depend on the method used to form the matrix.

For example, a matrix in addition to the pharmaceutical compositions described above may include hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting sustained release of the pharmaceutical composition(s) and which melts (or softens to the extent necessary to be extruded) may be used in accordance with the present invention.

The oral dosage form may contain between 1% and 80% (by weight) of one or more hydrophilic or hydrophobic material(s).

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing. Of these materials, acrylic polymers, e.g., Eudragit® RSPO, the cellulose ethers, e.g., hydroxyalkylcelluloses and carboxyalkylcelluloses are preferred.

Preferred hydrophobic materials are water-insoluble with more or less pronounced hydrophilic and/or hydrophobic trends. Preferably, the hydrophobic materials useful in the invention have a melting point from about 40° C. to about 200° C., preferably from about 45° C. to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes are waxes as defined in Fette, Seifen, Anstrichmittel 76, 135 (1974) and include, for example, beeswax, glycowax, castor wax and carnauba wax.

Suitable hydrophobic materials which may be used in accordance with the present invention include long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° C. and 90° C. are preferred. Of the long chain hydrocarbon materials, fatty (aliphatic) alcohols are preferred in certain embodiments. The oral dosage form may contain up to 60% of at least one long chain hydrocarbon.

In certain embodiments, a combination of two or more hydrophobic materials is included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of API release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by weight) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by weight) of the total dosage.

In one embodiment, the ratio of, e.g., the at least one hydroxyalkyl cellulose or acrylic resin to the at least one aliphatic alcohol/polyalkylene glycol determines, to a (w/w) of the at least one hydroxyalkyl cellulose to the at least one aliphatic alcohol/polyalkylene glycol of between 1:2 and 1:4 is preferred, with a ratio of between 1:3 and 1:4 being particularly preferred.

In certain embodiments, the oral dosage form contains at least one polyalkylene glycol. The amount of the at least one polyalkylene glycol in the oral dosage form may be up to 60%. The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

In certain embodiments, the sustained release matrix may comprise polyethylene oxide. In certain embodiments polyethylene oxide comprises from about 40% to about 95% of the dosage form. In certain embodiments polyethylene oxide comprises from about 50% to about 95% of the dosage form. In certain embodiments polyethylene oxide comprises from about 55% to about 90% of the dosage form. In certain embodiments polyethylene oxide comprises from about 60% to about 90% of the dosage form.

Another suitable sustained release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a sustained release matrix may also contain suitable quantities of other materials, e.g., diluents, lubricants, binders, granulating aids, colorants, flavorants and glidants that are conventional in the pharmaceutical art.

Matrix-Particulates

In order to facilitate the preparation of a solid, sustained release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose, and an opioid according to present invention; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose granules with water.

In yet other alternative embodiments, a spheronizing agent, together with the active can be spheronized to form spheroids. Microcrystalline cellulose is a preferred spheronizing agent. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, is preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g., a wax, and incorporating a powdered drug therein. To obtain a sustained release dosage form, it may be necessary to incorporate an additional hydrophobic substance, e.g., ethylcellulose or a water-insoluble acrylic polymer, into the molten wax hydrophobic material. Examples of sustained release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w). For purposes of the present invention, a wax-like substance is defined as any material which is normally solid at room temperature and has a melting point of from about 25° to about 100° C.

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g., diluents, lubricants, binders, granulating aids, colorants, flavorants and glidants that are conventional in the pharmaceutical art in amounts up to about 50% of the particulate if desired.

Specific examples of pharmaceutically acceptable carriers and excipients that may be used to formulate oral dosage forms are described in the Handbook of Pharmaceutical Excipients, American Pharmaceutical Association (1986).

Melt Extrusion Multiparticulates

The preparation of a suitable melt-extruded matrix according to the present invention may, for example, include the steps of blending the API together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the API for a time period of from about 8 to about 24 hours.

An optional process for preparing the melt extrusions of the present invention includes directly metering into an extruder a hydrophobic material, the opioid API, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the teams "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553-1593 (1980).

In yet another preferred embodiment, the extrudate can be shaped into tablets as set forth in U.S. Pat. No. 4,957,681 (Klimesch, et. al.), described in additional detail above.

Optionally, the sustained release melt-extruded multiparticulate systems or tablets can be coated, or the gelatin capsule containing the multiparticulates can be further coated, with a sustained release coating such as the sustained release coatings described above. Such coatings preferably include a sufficient amount of hydrophobic material to obtain a weight gain level from about 2 to about 30 percent, although the overcoat may be greater depending upon the desired release rate, among other things.

The melt-extruded unit dosage forms of the present invention may further include combinations of melt-extruded particles before being encapsulated. Furthermore, the unit dosage forms can also include an amount of an immediate release agent for prompt release. The immediate release agent may be incorporated, e.g., as separate pellets within a gelatin capsule, or may be coated on the surface of the multiparticulates after preparation of the dosage forms (e.g., sustained release coating or matrix-based). The unit dosage forms of the present invention may also contain a combination of sustained release beads and matrix multiparticulates to achieve a desired effect.

The sustained release formulations of the present invention preferably slowly release the agent(s), e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the API, which can be added thereafter to the extrudate. Such formulations typically will have the agents blended together with the extruded matrix material, and then the mixture would be tabletted in order to provide a slow release formulation.

Coatings

The dosage forms of the present invention may optionally be coated with one or more materials suitable for the regulation of release or for the protection of the formulation. In one embodiment, coatings are provided to permit either pH-dependent or pH-independent release. A pH-dependent coating serves to release the active in desired areas of the gastro-intestinal (GI) tract, e.g., the stomach or small intestine, such that an absorption profile is provided which is capable of providing at least about eight hours and preferably about twelve hours to up to about twenty-four hours of the therapeutic effect (such as analgesia) to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the API is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493.

Other examples of sustained release formulations and coatings which may be used in accordance with the present invention include those described in U.S. Pat. Nos. 5,324,351; 5,356,467, and 5,472,712.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

Acrylic Polymers

In other preferred embodiments of the present invention, the hydrophobic material comprising the sustained release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly (methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Evonik. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Evonik under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL and 90% Eudragit® RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethyl-cellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Sustained Release Osmotic Dosage Form

Sustained release dosage forms according to the present invention may also be prepared as osmotic dosage formulations. The osmotic dosage forms preferably include a bilayer core comprising a drug layer (e.g., containing oxymorphone or a salt or solvate thereof as described above) and a delivery or push layer, wherein the bilayer core is surrounded by a semipermeable wall and optionally having at least one passageway disposed therein.

The expression "passageway" as used for the purpose of the present description, includes aperture, orifice, bore, pore, porous element through which an API (e.g., oxymorphone hydrochloride) may be pumped, diffuse or migrate through a fiber, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The dosage form can be manufactured with one or more passageways in spaced-apart relation on one or more surfaces of the dosage form. A passageway and equipment for forming a passageway are disclosed in U.S. Pat. Nos. 3,845,770; 3,916,899; 4,063,064 and 4,088,864. Passageways comprising sustained-release dimensions sized, shaped and adapted as a releasing-pore formed by aqueous leaching to provide a releasing-pore of a sustained-release rate are disclosed in U.S. Pat. Nos. 4,200,098 and 4,285,987.

In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly (ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of the osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the active pharmaceutical ingredient (e.g., oxymorphone hydrochloride) from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropyl isopropyl cellulose, hydroxypropylbutylcellulose, and hydroxypropylpentylcellulose.

The push layer optionally may comprise a nontoxic colorant or dye. Examples of colorants or dyes include but are not limited to Food and Drug Administration Colorant (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tert-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-di-tert butylphenol, α-tocopherol, and propylgallate.

In certain alternative embodiments, the dosage form comprises a homogenous core comprising an active pharmaceutical ingredient (e.g., oxymorphone hydrochloride), a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The homogenous core is surrounded by a semipermeable wall having a passageway (as defined above) for the release of the opioid API.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ ($cm^2$/hr atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. Other hinders include for example, acacia, starch, gelatin, and hydroxypropylalkylcellulose of from 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

Suppositories

The sustained release formulations of the present invention may be formulated as a pharmaceutical suppository for rectal administration comprising a suitable suppository base, and a pharmaceutical opioid composition. Preparation of sustained release suppository formulations is described in, e.g., U.S. Pat. No. 5,215,758.

Prior to absorption, the drug must be in solution. In the case of suppositories, solution must be preceded by dissolution of the suppository base, or the melting of the base and subsequent partition of the drug from the suppository base into the rectal fluid. The absorption of the drug into the body may be altered by the suppository base. Thus, the particular suppository base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

Among the different factors affecting the dissolution time (or release rate) of the drugs are the surface area of the drug substance presented to the dissolution solvent medium, the pH of the solution, the solubility of the substance in the specific solvent medium, and the driving forces of the saturation concentration of dissolved materials in the solvent medium. Generally, factors affecting the absorption of drugs from suppositories administered rectally include suppository vehicle, absorption site pH, drug pKa, degree of ionization, and lipid solubility.

The suppository base chosen should be compatible with the active of the present invention. Further, the suppository base is preferably non-toxic and nonirritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20 percent to about 90 percent of the total weight of the suppository. Preferably, the amount of suppository base in the suppository is from about 65 percent to about 80 percent, of the total weight of the suppository.

The following examples are meant to illustrate, but in no way to limit, the present invention.

EXAMPLES

Comparative Example 1: Preparation of Oxymorphone According to Example 2 of WO 2008/130553

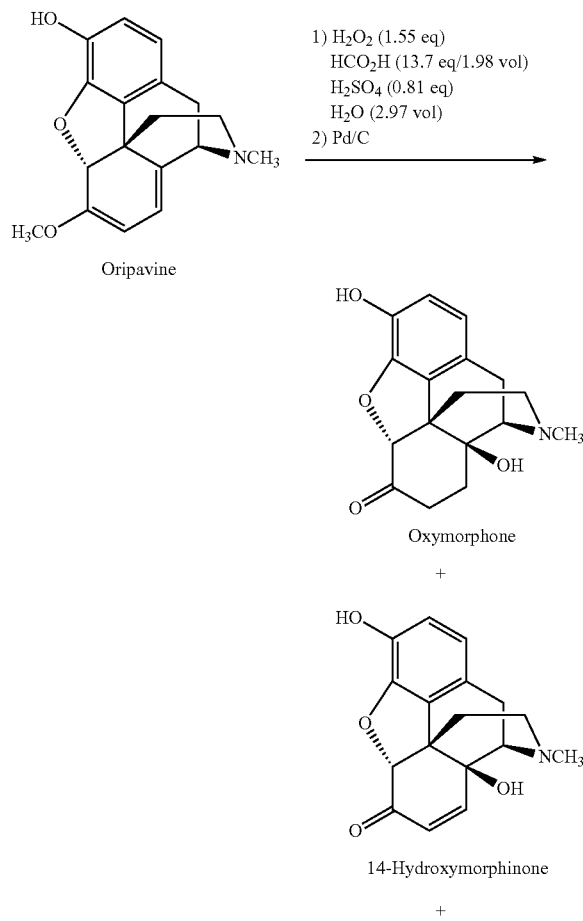

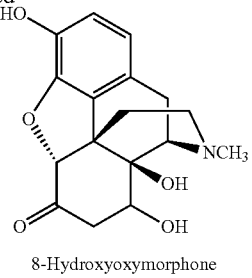

8-Hydroxyoxymorphone

Example 2 from WO 2008/130553 was repeated as follows.

1. Into a 100 mL reaction vessel equipped with a temperature probe, an overhead stirrer and a reflux condenser, oripavine (3.03 g, 10.2 mmol) was charged as a slurry in deionized water (9 mL).

2. The reaction mixture was stirred at 300 rpm, while maintaining an internal temperature of 20° C.

3. Formic acid (88%, 6 mL, 139.9 mmol) was added into the reaction mixture. Upon the addition, the solids readily dissolved into solution. During the formic acid addition, the temperature of the reaction mixture increased to 30° C.

4. After the solution temperature had cooled to 20° C., 35% hydrogen peroxide (1.06 mL, 15.8 mmol) and sulfuric acid (0.45 mL, 8.15 mmol) were added to the reaction.

5. The reaction was stirred (300 rpm) at 20° C. for 16 hours, until about 95% of the oripavine had been consumed according to the HPLC analysis described in Example 11A.

6. 0.30 g of 5% palladium on carbon was charged into the reaction mixture, and the mixture was stirred at 20° C. for 30 minutes.

7. Sodium formate (0.60 g, 8.82 mmol) and triethylamine (7.5 mL, 53.8 mmol) were added to the reaction mixture, and the mixture was heated to 45° C. and stirred at 45° C. for 2 hours.

8. The mixture was heated to 80° C. and stirred at 80° C. for an additional 8 hours.

9. The reaction was then cooled to 20° C. and stirred at 20° C. for 8 hours. No precipitation was observed at this temperature.

10. The reaction mixture was filtered through a plug of celite.

11. The filtrate was basified to a pH of about 9.3 with concentrated ammonium hydroxide, to precipitate oxymorphone free base.

12. The resulting mixture was stirred at room temperature for 1 hour.

13. The resulting mixture was then filtered, washed with water (3×15 mL), and dried in a vacuum oven at 80° C. for 16 hours to yield 2.04 g of solid.

14. Analysis of the solid by the HPLC method of Example 11A showed an HPLC peak area ratio of oxymorphone:14-hydroxymorphinone:8-hydroxyoxymorphone of 15,803,069:1,845:25,714. The oxymorphone base comprised 96.03% of the composition (based on HPLC area percent), 14-hydroxymorphinone comprised 117 ppm of the composition (based on HPLC area percent), and 8-hydroxyoxymorphone comprised 1627 ppm of the composition (based on HPLC area percent). The auto-scaled chromatogram and peak results from this analysis are depicted in FIG. 1.

About 14.5 molar equivalents of total acid per molar equivalent of oripavine were used in this example (13.7 molar equivalents of $HCO_2H$, 0.81 molar equivalents of $H_2SO_4$). The molar ratio of sulfuric acid to formic acid was about 1:17.2. No precipitation was observed up to step 11. A molar excess of formic acid was present during the hydrogenation.

Comparative Example 2: Preparation of Oxymorphone Free Base According to Example 3 of WO 2008/130553

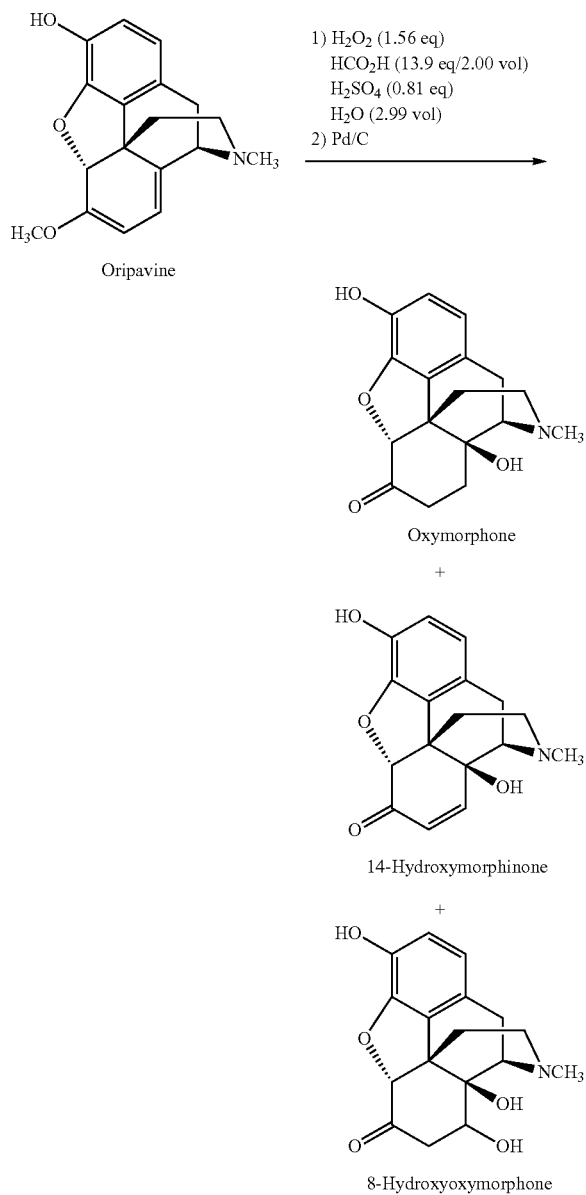

Example 3 from WO 2008/130553 was repeated as follows.

1. Into a 100 mL reaction vessel equipped with a temperature probe, overhead stirrer and reflux condenser, oripavine (3.01 g, 10.1 mmol) was charged as a slurry in deionized water (9 mL).

2. The reaction mixture was stirred at 300 rpm, while maintaining an internal temperature of 20° C.

3. Formic acid (88%, 6 mL, 139.9 mmol) was added into the reaction. Upon the addition, the solids readily dissolved into solution. During the formic acid addition, the temperature of the reaction mixture increased to 30° C.

4. After the solution temperature had cooled to 20° C., 35% hydrogen peroxide (1.06 mL, 15.8 mmol) and sulfuric acid (0.45 mL, 8.15 mmol) were added to the reaction.

5. The reaction was stirred (300 rpm) at 20° C. for 16 hours, until the oripavine had been consumed according to the HPLC analysis of Example 11A.

6. 0.30 g of 5% palladium on carbon was charged into the reaction mixture, and the mixture was stirred at 20° C. for 30 minutes.

7. Triethylamine (8.8 mL, 63.1 mmol) was added to the reaction mixture, and the reaction mixture was heated to 45° C. and stirred at 45° C. for 2 hours.

8. The mixture was heated to 80° C. and stirred at 80° C. for an additional 8 hours.

9. The reaction was then cooled to 20° C. and stirred at 20° C. for 8 hours. No solid precipitation was observed at this temperature.

10. The reaction mixture was filtered through a plug of celite.

11. The filtrate was basified to pH=9.25 with concentrated ammonium hydroxide, and the precipitated composition was allowed to stir at room temperature for 1 hour.

12. The precipitated composition was then filtered, washed with water (3×15 mL) and dried in a vacuum oven at 80° C. for 16 hours to yield 1.33 g of precipitate.

Figure 2:
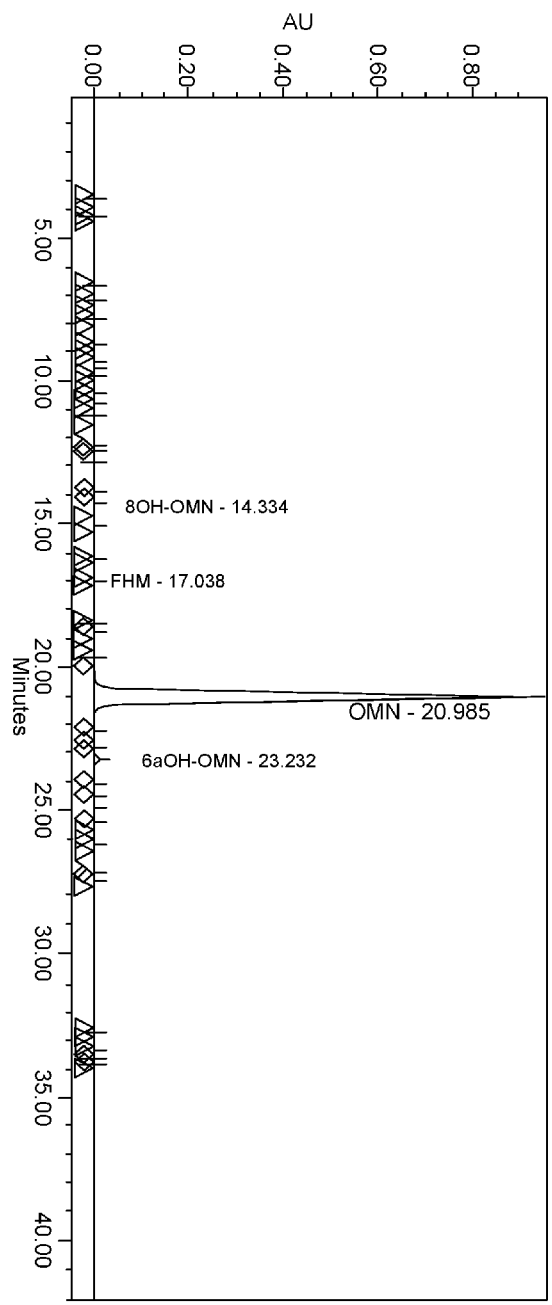
FIG. 2 shows the auto-scaled chromatograph and peak results of the analysis of the precipitated oxymorphone of Comparative Example 2.

13. Analysis of the precipitate by the HPLC method of Example 11A showed an HPLC peak area ratio of oxymorphone:14-hydroxymorphinone:8-hydroxyoxymorphone of 13,906,304:2,146:46,937. In other words, the oxymorphone base comprised 94.94% of the composition (based on HPLC area percent), 14-hydroxymorphinone comprised 154 ppm of the composition (based on HPLC area percent), and 8-hydroxyoxymorphone comprised 3377 ppm of the composition (based on HPLC area percent). The auto-scaled chromatogram and peak results from this analysis are depicted in FIG. 2.

About 14.7 molar equivalents of total acid per molar equivalent of oripavine were used in this example. The molar ratio of sulfuric acid to formic acid was about 1:17.2. No precipitation was observed up to step 11. A molar excess of formic acid was present during the hydrogenation.

Comparative Example 3: Preparation of 14-Hydroxymorphinone from Oripavine without Sulfuric Acid

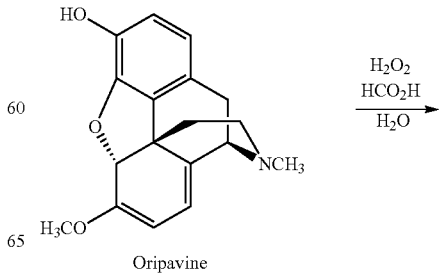

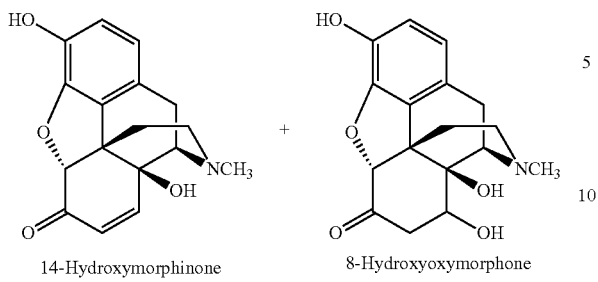

14-Hydroxymorphinone     8-Hydroxyoxymorphone

1. Oripavine (99.99 g, 336 mmol) was charged as a slurry in deionized water (150 mL) into a 500 mL jacketed vessel.

2. The slurry was stirred (250 rpm) at ambient reaction temperature (approximately 25° C.).

3. Formic acid (100 mL, 2332 mmol, 88%) was added to the mixture in one portion. The solids completely dissolved upon the addition, and a slight exothermic reaction was observed (temperature increase to approximately 34° C.). The solution was then allowed to cool hack to ambient temperature (approximately 25° C.).

4. While holding the temperature at approximately 25° C., hydrogen peroxide (31.2 mL, 363 mmol, 35%, M=11.86) was added to the solution at a controlled rate of 1.56 mL/minute (0.05 equivalents/minute).

5. After addition was complete, the solution was allowed to stir an additional 30 minutes at ambient temperature.

6. The solution was then heated to 48° C. and held at this temperature for about 3.5 hours, and sampled by HPLC for reaction completion.

7. After approximately 3.5 hours of stirring at 48° C., the solution was cooled to 10° C. over 35 minutes.

8. The solution was held at 10° C. for approximately 16 hours, and analyzed by HPLC. A sample was shown to contain 97.04% (based on HPLC area percent) 14-hydroxymorphinone, 5200 ppm (based on HPLC area percent) oripavine, and 10900 ppm (based on HPLC area percent) 8-hydroxyoxymorphone.

9. The solution was then utilized for subsequent hydrogenation in Example 4.

Comparative Example 4: Preparation of Oxymorphone from 14-Hydroxymorphinone

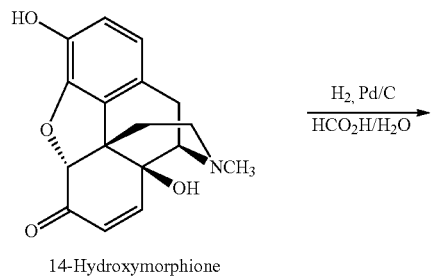

14-Hydroxymorphione

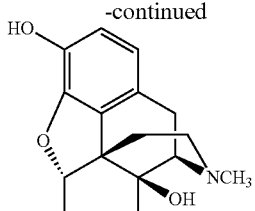

Oxymorphone

14-Hydroxymorphinone

8- Hydroxyoxymorphone 1. 5% Palladium on carbon (0.60 g) was charged into a 1 L ZipperClave® autoclave high pressure reaction vessel, followed by the solution prepared in Example 3.

2. Deionized water (100 mL) and formic acid (100 mL, 88%, 2332 mmol) were added into the reaction solution in one portion.

3. The vessel was sealed and hydrogenated at 60 psia (413.69 kPa), 55° C., for 3 hours and 10 minutes.

4. The solution was vented and purged with nitrogen 3 times.

5. A sample of the solution was analyzed by HPLC for reaction completion.

6. The palladium on carbon was removed from the solution by filtration through 2 layers of filter paper and the filtrate was stored in a refrigerator at approximately 5° C. overnight.

7. The filtrate was transferred to a cooled 1 L jacketed vessel (0-5° C.).

8. 50% sodium hydroxide was added into the cooled solution at a rate such that the temperature of the solution did not exceed 20° C., until a final pH in a range from 9.0 to 9.25 was achieved.

9. The resulting solids were stirred at 5° C. for an additional 30 minutes before being filtered by vacuum filtration through a paper filter (Whatman#2).

10. The resulting solid material was slurry washed with deionized water (3×200 mL) and further dried by vacuum on the filter for 1 hour, before being transferred to a vacuum oven and dried at 40° C. under house vacuum (~28 mmHg (3.73 kPa)). The solid material was analyzed by HPLC. The analysis showed that the solid material contained 95.96% oxymorphone, based on HPLC area percent, 3100 ppm 14-hydroxymorphinone, based on HPLC area percent, and 19600 ppm 8-hydroxyoxymorphone, based on HPLC area percent.

About 6.94 molar equivalents of formic acid per molar equivalent of oripavine were used in Example 3, i.e. during the oxidation. No sulfuric acid was used. No precipitation was observed up to step 8 of Example 4. A molar excess of formic acid was present during the hydrogenation.

Comparative Example 5: Preparation of 14-Hydroxymorphinone Sulfate

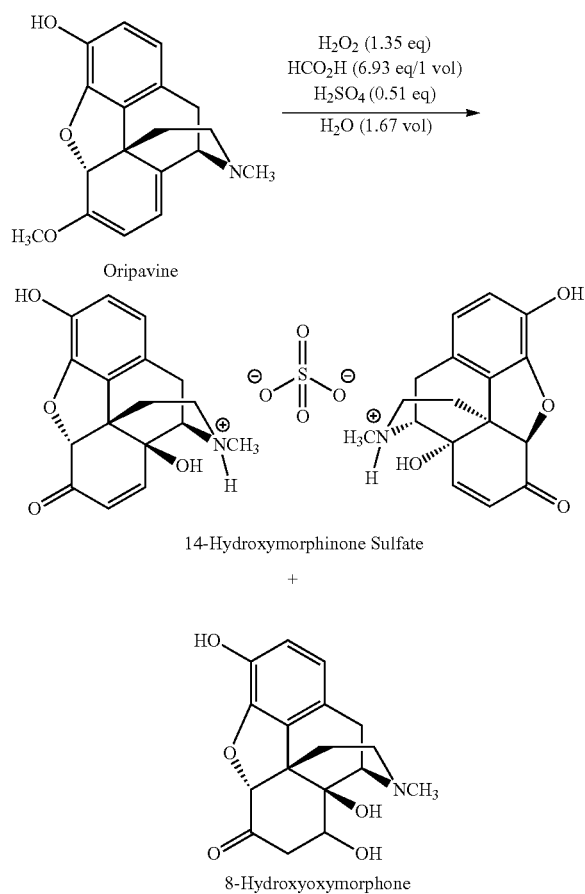

1. Oripavine (30.0 g, 101 mmol) was charged as a slurry in deionized water (45 mL) into a 300 mL jacketed vessel, overhead stirred and equipped with a temperature probe and an addition funnel.
2. The jacket temperature for the vessel was set to 22° C., and the slurry was stirred at 500 rpm.
3. Formic acid (30 mL, 700 mmol) was added into the vessel. The solids readily dissolved into solution upon addition of formic acid. During the formic acid addition, the temperature of the reaction mixture increased to 30° C.
4. Sulfuric acid (2.5 mL, 45 mmol) was added to the solution, and the solution was stirred at 500 rpm.
5. After the solution temperature had cooled below 25° C., hydrogen peroxide (10.25 mL, 119 mmol) was added to the reaction through the addition funnel at a rate of 0.17 mL/minute.
6. After the hydrogen peroxide addition was complete, an additional 5 mL of deionized water was added to the reaction through the addition funnel, and the reaction solution was allowed to stir (500 rpm) at 22° C., and the reaction progress was monitored by HPLC. After stirring for 20 hours, approximately 15-20% of the oripavine was still present in the reaction mixture, based on HPLC area %.
7. The reaction mixture was heated to 30° C. and an additional 1.5 mL (17 mmol) of hydrogen peroxide was added to the reaction in one portion, to increase conversion of oripavine (greater than 99% conversion, as determined by HPLC).
8. The reaction mixture was stirred (500 rpm) at 30° C. for an additional 16 hours.
9. Sulfuric acid (0.35 mL, 6.3 mmol) was added into the reaction, and the solution was stirred (500 rpm) for 10 minutes.
10. Methanol (60 mL) was added into the reaction mixture, and the rate of stirring was reduced to 200 rpm.
11. The reaction mixture was cooled to 15° C. over 2.5 hours. Upon cooling, solids precipitated out of the solution forming a suspension.
12. The resulting suspension was stirred (200 rpm) at 15° C. for an additional 1 hour.
13. The solids were filtered under vacuum using a Buchner funnel, with Whatman#1 filter paper, and the solids were collected and washed with methanol (2×60 mL). A sample of the solids was analyzed by the HPLC method of Example 11A, and was shown to contain 14-hydroxymorphinone with 349 ppm of 8-hydroxyoxymorphone (based on HPLC area percent).
14. The solids were dried under vacuum on the Buchner funnel for 30 minutes, before being transferred to a drying oven and dried under vacuum to a constant weight. The solids contained 18.09 g (26 mmol (calculated without water of crystallization), 51.5% yield) of 14-hydroxymorphinone sulfate as fine yellow crystals, containing 349 ppm of 8-hydroxyoxymorphone (based on HPLC area percent in relation to 14-hydroxymorphinone).
15. To see whether the yield can be increased, the filtrate and methanol washes were returned to the jacketed vessel and tert-butyl methyl ether (60 mL) was added to the mixture. Upon addition of the tert-butyl methyl ether, solids precipitated out of the reaction mixture. The mixture was stirred at 200 rpm and heated to 55° C.
16. After the solids had completely dissolved, the solution was gradually cooled to 20° C. over 3 hours. The mixture was stirred (200 rpm) at 20° C. for an additional 48 hours. Upon cooling and stirring, solids precipitated.
17. The solids were filtered under vacuum using a Buchner funnel, with Whatman#2 filter paper, washed with tert-butyl methyl ether (60 mL) and dried under vacuum on the Buchner funnel for 30 minutes, before being transferred to a drying oven and dried under vacuum to a constant weight. The solids contained 5.60 g (8 mmol (calculated without water of crystallization), 15.8% yield) of 14-hydroxymorphinone sulfate as tan crystals. The composition of the tan crystals was substantially the same as the composition of the yellow crystals isolated initially, except that it contained 2051 ppm, based on HPLC area percent, of 8-hydroxyoxymorphone.

About 7.4 molar equivalents of total acid per molar equivalent of oripavine were used in this example. The molar ratio of sulfuric acid to formic acid was about 1:13.6. Precipitation was observed in step 11.

Comparative Example 6: Preparation of Oxymorphone Free Base

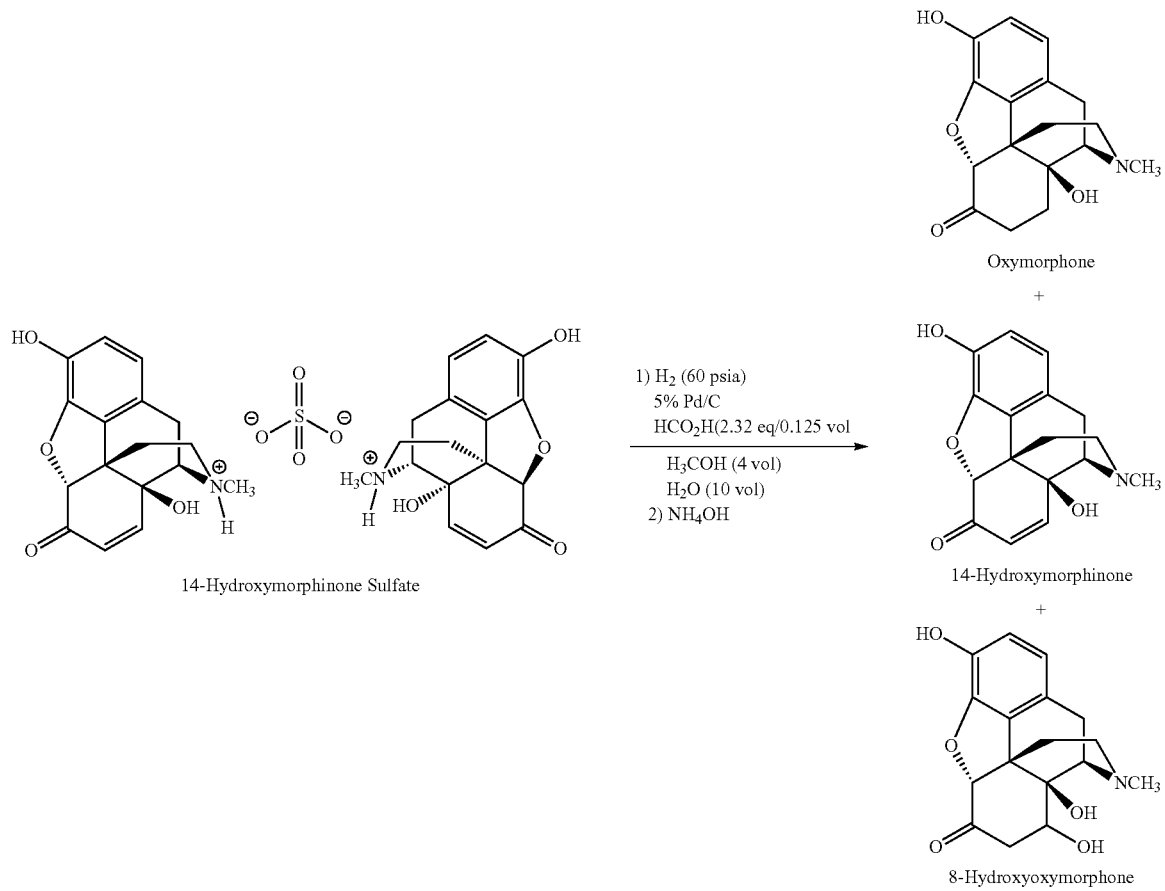

1. 14-Hydroxymorphinone sulfate (11.95 g, 17.2 mmol (calculated without water of crystallization)) (i.e., solids from the first isolation of Example 5 (yellow crystals)), deionized water (120 mL) and methanol (48 mL) were charged into a 250 mL flask equipped with a magnetic stir bar. The majority of solids did not dissolve into solution at room temperature.

2. Formic acid (1.50 mL, 40 mmol) was added to the mixture, and the mixture was stirred vigorously at 22° C. After 30 minutes of stirring at 22° C., a large portion of the solid material remained insoluble.

3. The mixture was transferred from the flask to a high pressure reaction vessel equipped with a magnetic stir bar. Into the vessel was charged 5% palladium on carbon (0.091 g) and the vessel was sealed.

4. The mixture was stirred at 750 rpm and heated to 40° C. The mixture was hydrogenated at 60 psia (413.69 kPa) for 6 hours.

5. The reaction was vented, purged with nitrogen, vented and hydrogenated at 60 psia (413.69 kPa) for an additional 3 hours.

6. The reaction was vented, purged with nitrogen and cooled to 22° C. over 8 hours.

7. The reaction mixture was filtered through filter paper to remove the palladium on carbon and the filtrate was sampled for HPLC analysis. The solution pH was 2.75. Analysis by the HPLC method of Example 11A showed that the sample contained oxymorphone free base with 72 ppm of 8-hydroxyoxymorphone (based on HPLC area percent in relation to oxymorphone free base) and 62 ppm of 14-hydroxymorphinone (based on HPLC area percent).

8. While stirring at 200 rpm, the solution was basified by adding 7 mL of 28% ammonium hydroxide to the filtrate solution; solids precipitated out of solution during the ammonium hydroxide addition and the final pH of the mixture was 9.06. Solids were isolated, dried at room temperature under vacuum and sampled by the HPLC method of Example 11A. Analysis by HPLC showed that the solid sample contained oxymorphone free base with 33 ppm of 8-hydroxyoxymorphone (based on HPLC area percent) and 17 ppm of 14-hydroxymorphinone (based on HPLC area percent).

9. The mixture was allowed to stir (200 rpm) at 22° C. for an additional 30 minutes.

10. The solids were filtered under vacuum using a Buchner funnel, with Whatman#2 filter paper, washed with water (2×12 mL) and dried under vacuum on the Buchner funnel for 30 minutes, before being transferred to a drying oven and dried under vacuum to a constant weight at 80° C. for 16 hours. The solids contained 7.89 g (26.2 mmol, 76% yield) of oxymorphone (base) as a white crystalline powder, 52 ppm of 8-hydroxyoxymorphone and 41 ppm of 14-hydroxymorphinone, based on the HPLC method of Example 11A.

About 7.4 molar equivalents of total acid per molar equivalent of oripavine were used in Example 5, i.e. during the oxidation. The molar ratio of sulfuric acid to formic acid was about 1:13.6 during oxidation. A molar excess of formic acid was present during the hydrogenation.

Synthetic Example 7: Preparation of 14-Hydroxymorphinone Sulfate

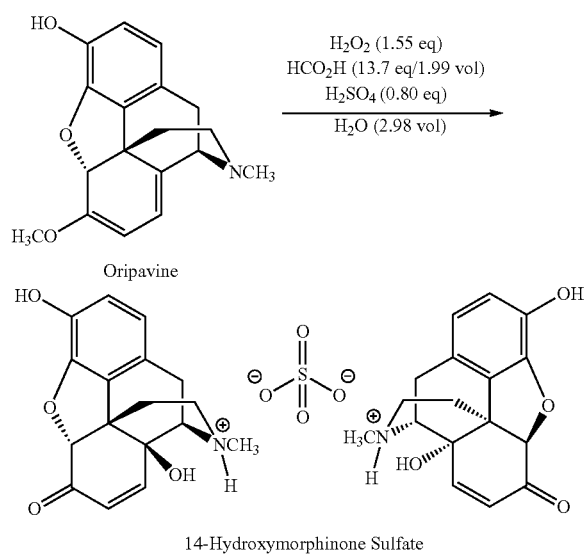

Figure 3:
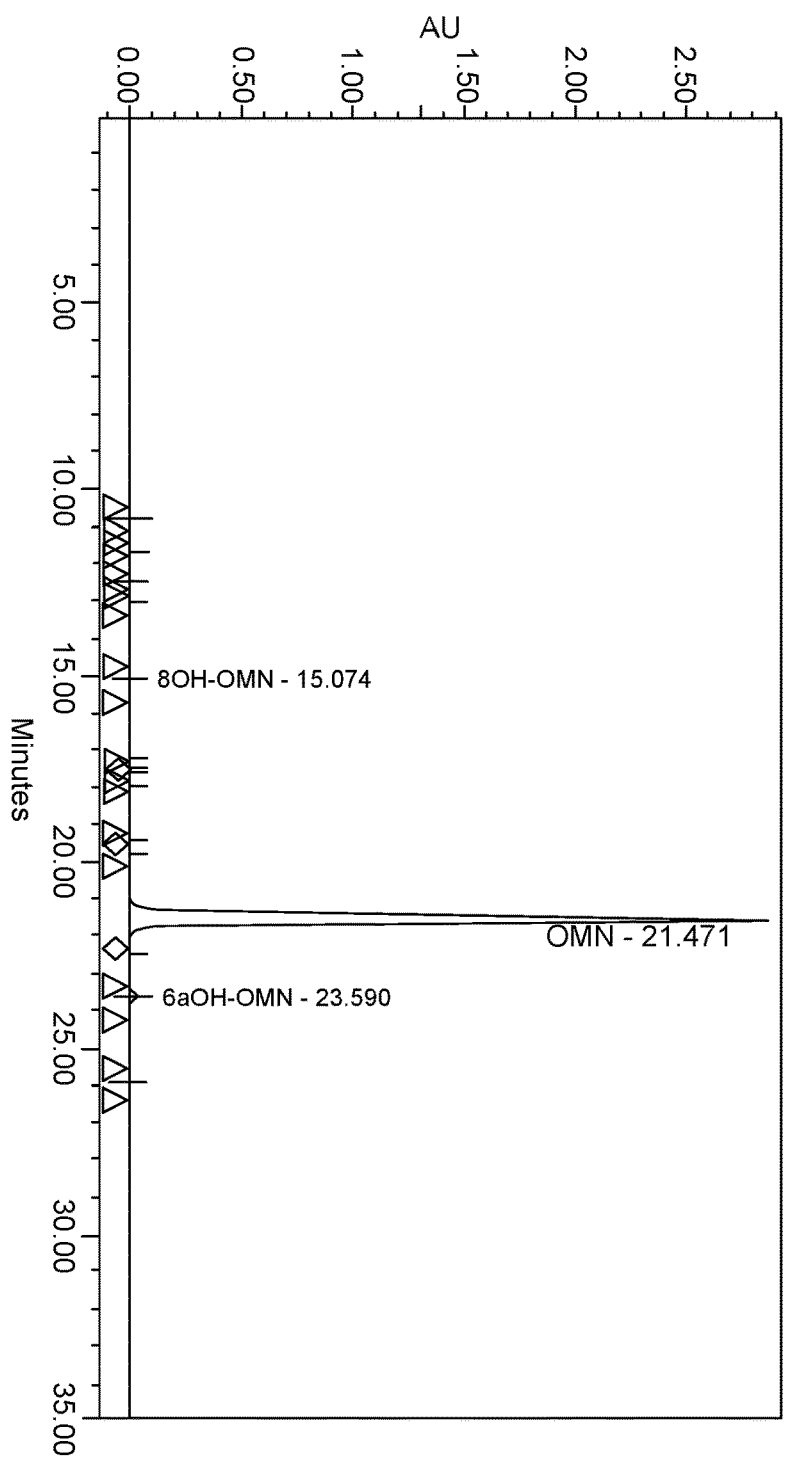
FIG. 3 shows the auto-scaled chromatograph and peak results of the analysis of the isolated solid oxymorphone of Comparative Example 10.
Figure 4:
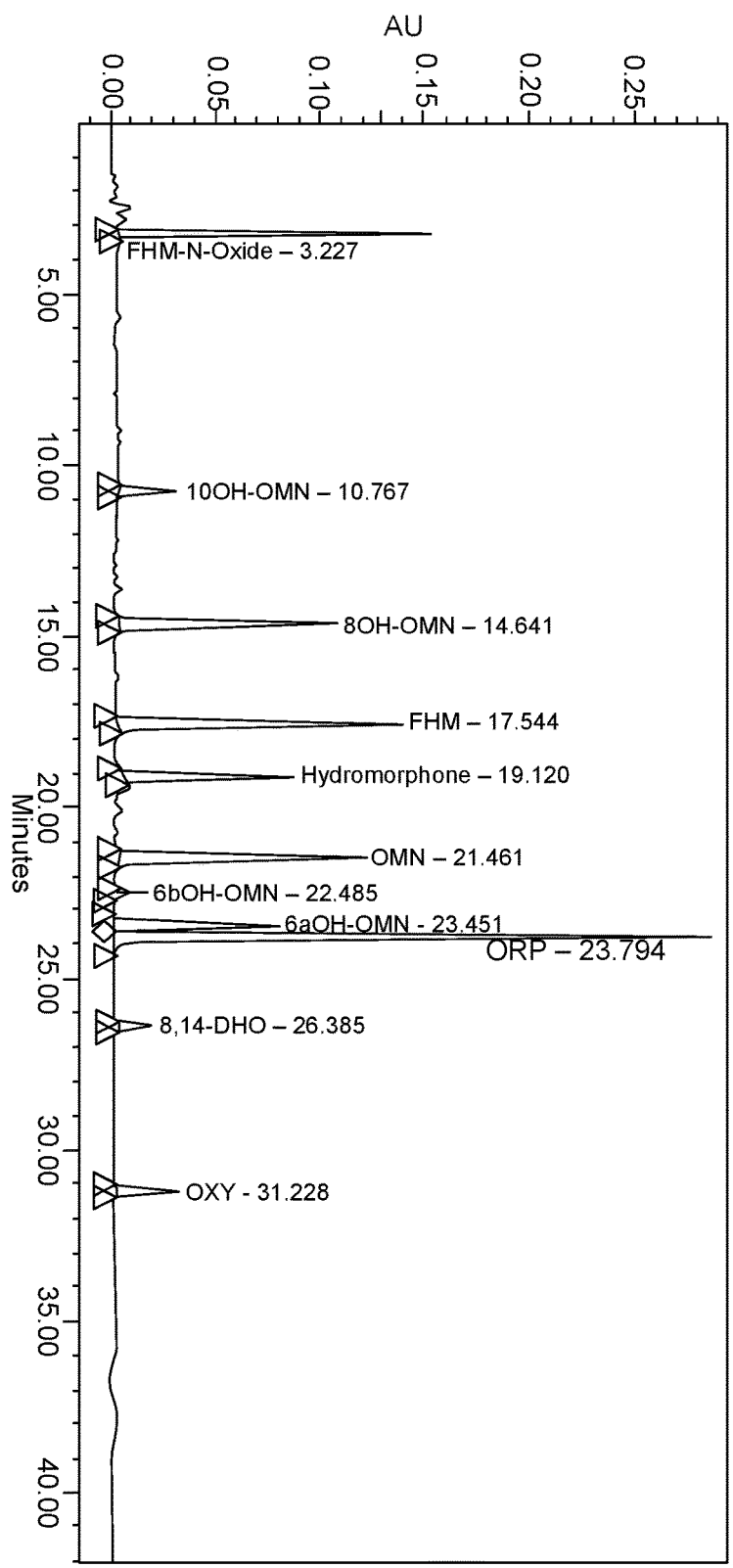
FIG. 4 shows a representative HPLC chromatogram for a standard mixture of opioids resulting from the HPLC method of Example 11A. Legend: see Example 11A.

14-Hydroxymorphinone sulfate was prepared as follows:

1. Into a 100 mL reaction vessel equipped with a temperature probe, overhead stirrer and reflux condenser, oripavine (3.02 g, 10.2 mmol) was charged as a slurry in deionized water (9 mL).
2. The reaction mixture was stirred at 300 rpm, while maintaining an internal temperature of 20° C.
3. Into the reaction was added 88% formic acid (6 mL, 139.9 mmol), and the solids readily dissolved into solution. During the formic acid addition, the temperature of the reaction mixture increased to 30° C.
4. After the solution temperature had cooled to 20° C., 35% hydrogen peroxide (1.06 mL, 15.8 mmol) and sulfuric acid (0.45 mL, 8.15 mmol) were added to the reaction.
5. The reaction was stirred (300 rpm) at 20° C. for 16 hours.
6. Stirring of the mixture was reduced to 75 rpm and the mixture was cooled to 0° C. over 1 hour. Solids began precipitating out of solution after the temperature of the mixture reached 15° C.
7. The mixture was stirred for an additional 1 hour at 0° C. The solids were filtered under vacuum using a Buchner funnel with Whatman #1 filter paper, and the filtered solids were washed with tert-butyl methyl ether (3×15 mL).
8. Additional solids precipitated out of the filtrate after the tert-butyl methyl ether washes were combined with the filtrate. These solids were also filtered under vacuum using a Buchner funnel with Whatman #1 filter paper.
9. The two batches of solids were dried separately under vacuum on the Buchner funnel for 1 hour.
10. The solids were further dried in a vacuum oven at 80° C. for 16 hours.
11. Isolated: 0.09 g of solid (14-hydroxymorphinone sulfate) from the first filtration with an HPLC peak area ratio of 14-hydroxymorphinone:8-hydroxyoxymorphone equal to 6,340,697:312 (49.2 ppm of 8-hydroxyoxymorphone), based on the HPLC method of Example 11A. The auto-scaled chromatograph of the sample is depicted in FIG. 3 of PCT/IB2013/001541.
12. Isolated: 2.33 g of solid from the second filtration with an HPLC peak area ratio of 14-hydroxymorphinone: 8-hydroxyoxymorphone equal to 5,672,733:1,561 (275 ppm 8-hydroxyoxymorphone, based on HPLC area percent), based on the HPLC method of Example 11A. The auto-scaled chromatograph of the sample is depicted in FIG. 4 of PCT/IB2013/001541.

About 14.5 molar equivalents of total acid per molar equivalent of oripavine were used in this example. The molar ratio of sulfuric acid to formic acid was about 1:17.1. Precipitation was observed in step 6.

Synthetic Example 8: Preparation of 14-Hydroxymorphinone Sulfate

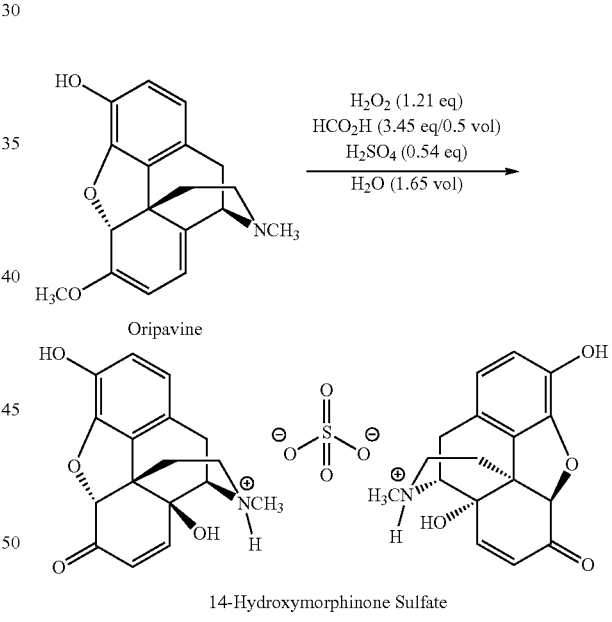

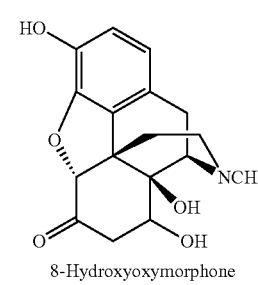

14-Hydroxymorphinone sulfate was prepared as follows:

1. Into a 100 mL jacketed vessel equipped with a temperature probe, overhead stirrer and an addition funnel, oripavine (20.0 g, 67.4 mmol) was charged as a slurry in deionized water (30 mL).

2. The jacket temperature for the vessel was set to 20° C. and the slurry was stirred at 300 rpm.

3. 88% formic acid (10 mL, 232 mmol) was added into the reaction mixture. The solids readily dissolved into solution upon this addition. During the formic acid addition, the temperature of the reaction mixture increased to 30° C.

4. Sulfuric acid (2.0 mL, 36 mmol) was added to the solution, and the solution was stirred at 300 rpm.

5. After the solution temperature had cooled below 25° C., 35% hydrogen peroxide (7.00 mL, 81.4 mmol) was added to the reaction over 15 minutes, using the addition funnel.

6. After the peroxide addition was complete, an additional 3 mL of deionized water was added to the reaction through the addition funnel.

7. The reaction solution was allowed to stir (300 rpm) at 20° C. for 20 minutes.

8. The reaction was then heated to 30° C. and held at 30° C., while stirring at 300 rpm for 8 hours.

9. The reaction mixture was then cooled to 20° C. over 2 hours and stirred (300 rpm) for an additional 8 hours at this temperature. Solids precipitated out of solution during the cooling from 30° C. to 20° C.

10. The resulting suspension was treated with 20 mL of methanol and the suspension was stirred at 20° C. for 30 minutes.

11. The solids were filtered under vacuum using a Buchner funnel with Whatman #1 filter paper, and the solids were washed with methanol (2×20 mL).

12. The solids were dried under vacuum on the Buchner funnel for 1 hour, before being transferred to a drying oven and dried under vacuum at 80° C. for 16 hours.

Figure 5:
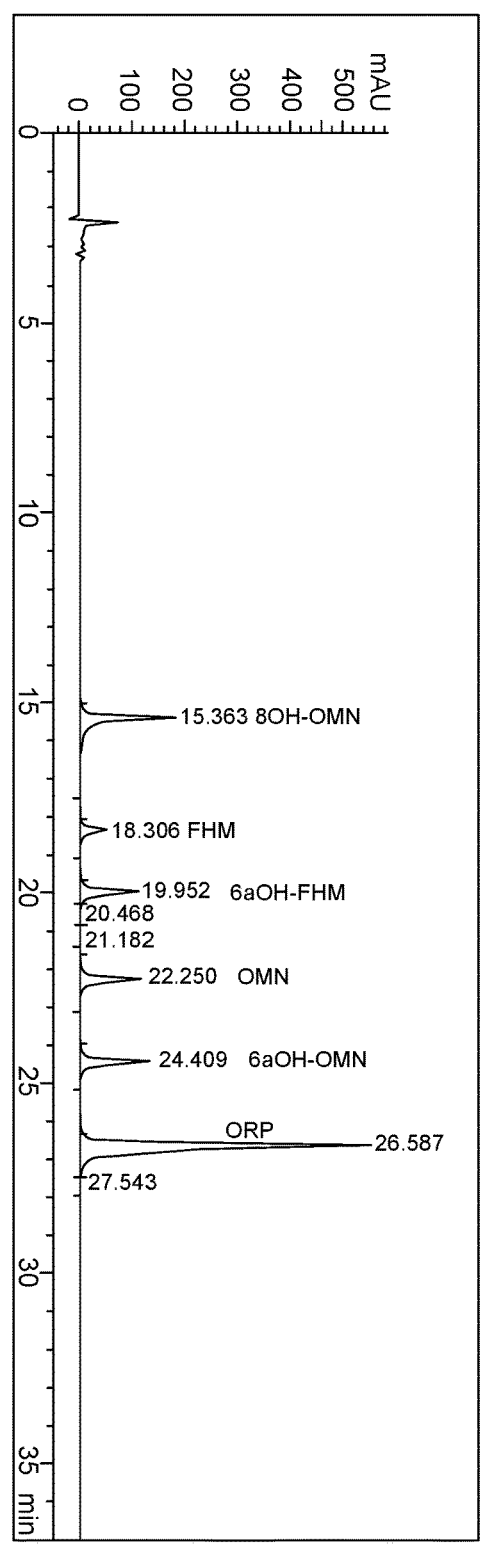
FIG. 5 shows a representative HPLC chromatogram for a standard mixture of opioids resulting from the HPLC method of Example 11B. Legend: see Example 11B.

13. 7.19 g of solid (26 mmol (calculated without water of crystallization) 14-hydroxymorphinone sulfate (73.2% yield)) was isolated as fine yellow-white crystals and analyzed by the HPLC method of Example 11A. Analysis showed an HPLC area ratio of 14-hydroxymorphinone:8-hydroxyoxymorphonc of 8,873,042:623. In other words, the composition comprised 97.88% 14-hydroxymorphinone (based on HPLC area percent) and 70 ppm 8-hydroxyoxymorphone (based on HPLC area percent). The auto-scaled chromatograph and peak results from this analysis are depicted in FIG. 5 of PCT/IB2013/001541.

About 4.66 molar equivalents of total acid per molar equivalent of oripavine were used in this example. The molar ratio of sulfuric acid to formic acid was about 1:6.4. Precipitation was observed in step 9.

As compared to the previous example (Example 7), less total acid (formic acid plus sulfuric acid) was used (4.66 equivalents vs. 14.5 equivalents), more sulfuric acid per formic acid was used (1:6.4 vs. 1:17.1) and the conditions of the present reaction resulted in better yield (73.2% vs. 67% 14-hydroxymorphinone sulfate).

Comparative Example 9: Preparation of 14-Hydroxymorphinone Sulfate

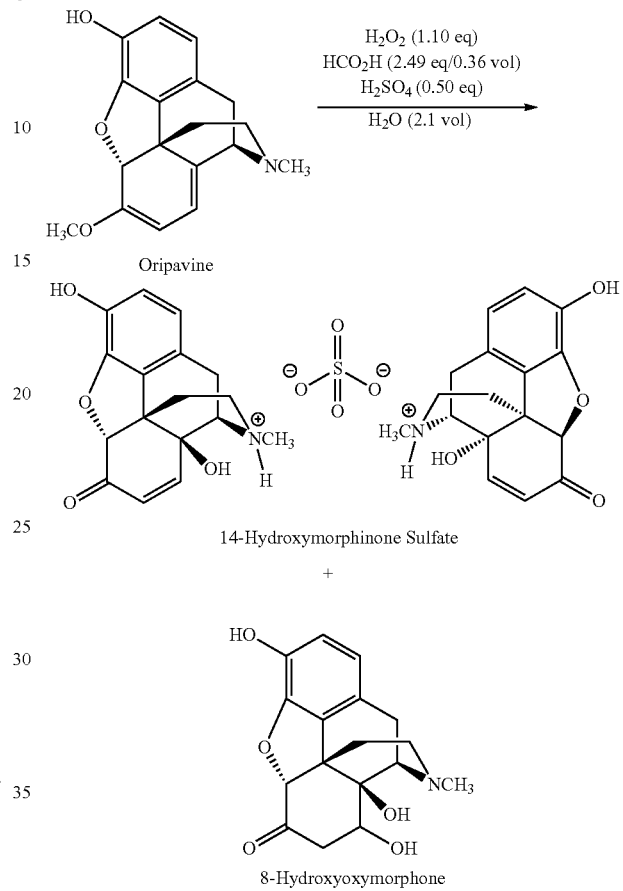

14-Hydroxymorphinone sulfate was prepared as follows.

1. Into an 80 mL reaction vessel equipped with a temperature probe and magnetic stirrer, oripavine (10.0 g, 33.7 mmol) was dissolved in deionized water (20 mL) and 88% formic acid (3.60 mL, 84.0 mmol).

2. The solution was stirred (600 rpm) at 22° C. for 15 minutes.

3. Sulfuric acid (0.94 mL, 17 mmol) was added into the reaction mixture, and the solution was stirred at 600 rpm. After the solution temperature had cooled below 25° C., 35% hydrogen peroxide (3.20 mL, 37.2 mmol) was added to the reaction in one portion.

4. After the peroxide addition was complete, an additional 1 mL of deionized water was added to the reaction. The reaction solution was allowed to stir (600 rpm) at 22° C. for 60 minutes.

5. The reaction was then heated to 30° C. over 20 minutes and held at 30° C., while stirring at 600 rpm for 16 hours.

6. Solids started to precipitate out of solution while stirring at 30° C.

7. The reaction mixture was then cooled to 22° C.

8. The resulting suspension was treated with 20 mL of methanol and the suspension was stirred at 22° C. for 5 minutes.

9. The solids were filtered under vacuum using a Buchner funnel with Whatman #1 filter paper, and the solids were washed with methanol (2×10 mL).

10. The solids were dried under vacuum on the Buchner funnel for 30 minutes, before being transferred to a drying oven and dried under vacuum at 80° C. for 16 hours.

Figure 6:
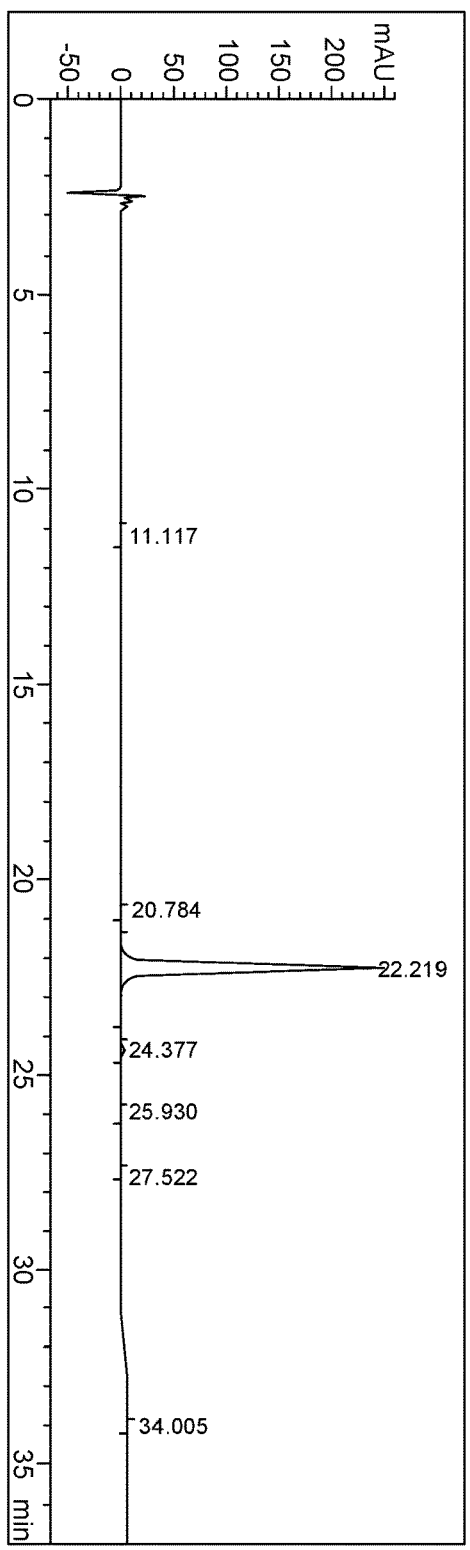
FIG. 6 shows the chromatogram of the analysis of the isolated solid oxymorphone of Example 16 for a sample concentration of 1 mg/mL.
Figure 7:
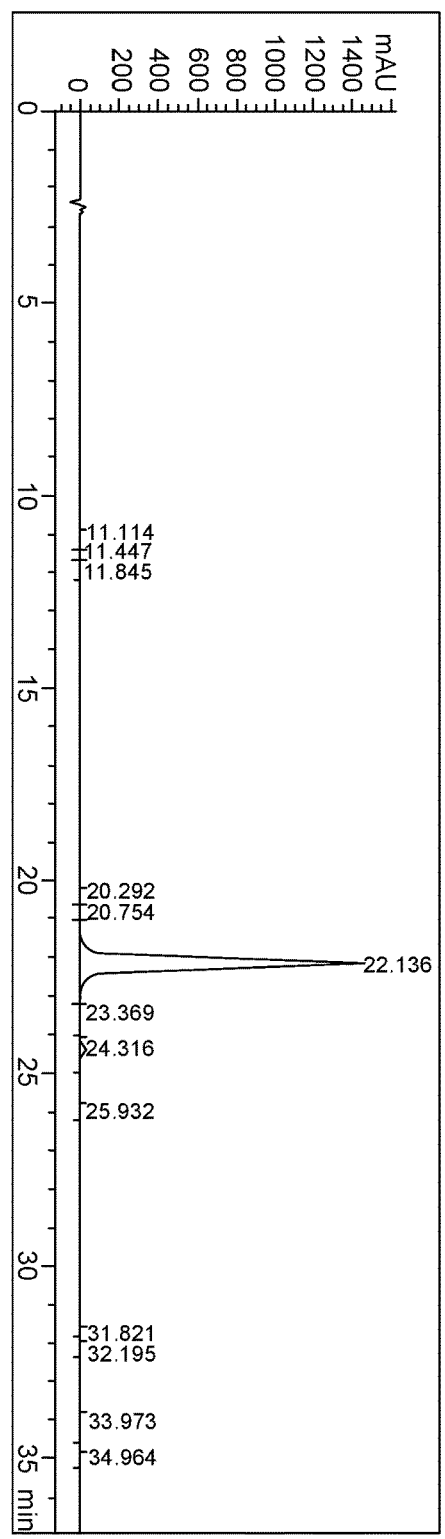
FIG. 7 shows the chromatogram of the analysis of the isolated solid oxymorphone of Example 16 for a sample concentration of 10 mg/mL.
Figure 8:
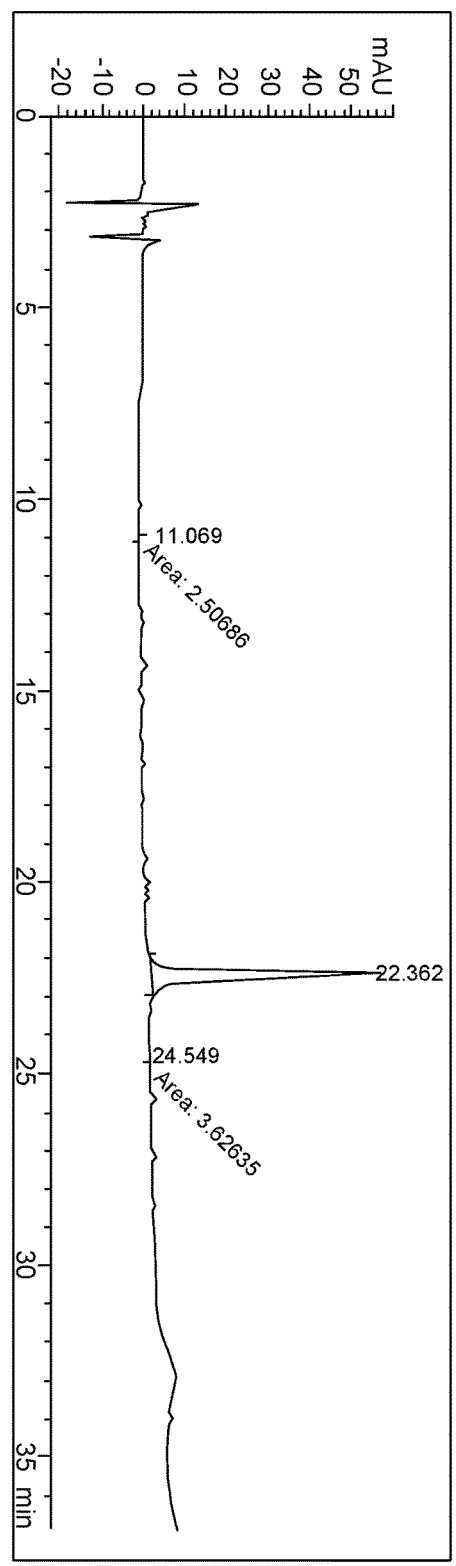
FIG. 8 shows the chromatogram of the analysis of the isolated solid oxymorphone of Example 17 for a sample concentration of 1 mg/mL.
Figure 9:
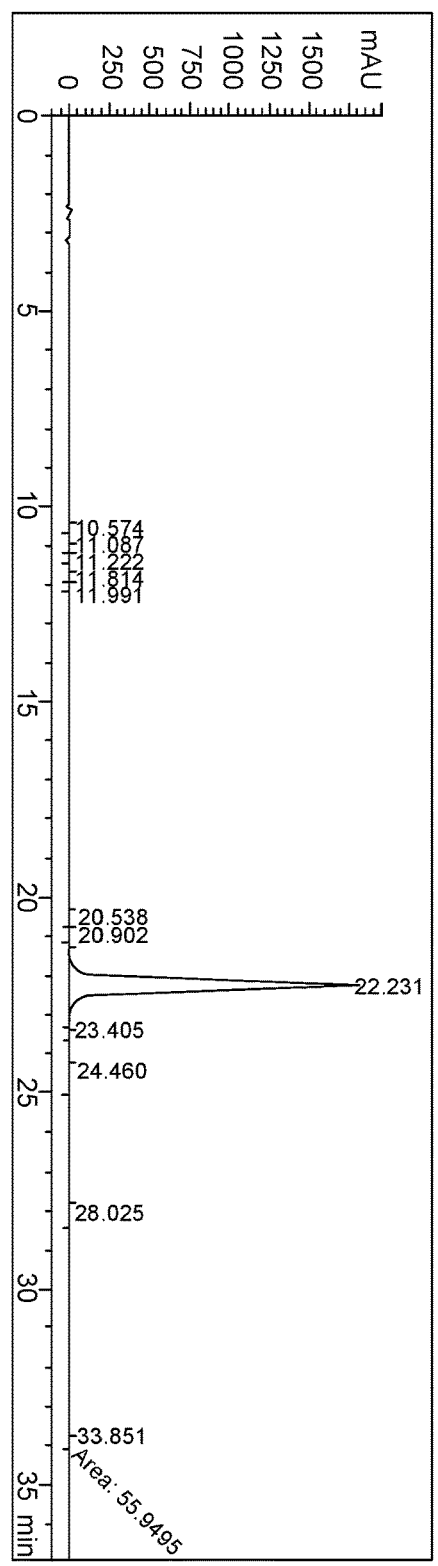
FIG. 9 shows the chromatogram of the analysis of the isolated solid oxymorphone of Example 17 for a sample concentration of 10 mg/mL.

11. 8.08 g (11.6 mmol (calculated without water of crystallization), 68.8% yield) of 14-hydroxymorphinone sulfate was isolated as fine yellow-white crystals. Analysis by the HPLC method of Example 11A showed an HPLC area ratio of 14-hydroxymorphinone: 8-hydroxyoxymorphone of 8,743,438:885. In other words, the mixture contained 101 ppm 8-hydroxyoxymorphone. The auto-scaled chromatograph and peak results from this analysis are depicted in FIG. 6 of PCT/IB2013/001541.

About 3 molar equivalents of total acid per molar equivalent of oripavine were used in this example. The molar ratio of sulfuric acid to formic acid was about 1:5. Precipitation was observed in step 6.

The resulting 14-hydroxymorphinone sulfate was used as starting material in the subsequent Example 10.

Comparative Example 10: Preparation of Oxymorphone from 14-Hydroxymorphinone Sulfate 3. The vessel was sealed, stirred at 750 rpm and heated to 40° C.

4. The mixture was then hydrogenated at 60 psia (413.69 kPa) for 5 hours.

5. The reaction was vented, purged with nitrogen, vented and hydrogenated at 60 psia (413.69 kPa) for an additional 1 hour.

6. The reaction was vented, purged with nitrogen and cooled to 22° C. over 8 hours.

7. The reaction mixture was filtered through filter paper to remove the palladium on carbon and the filtrate was sampled for the HPLC analysis of Example 11A. The results showed that less than 1% 14-hydroxymorphinone (free base) remained (by HPLC area %).

8. The filtrate was transferred to a 250 mL Erlenmeyer flask equipped with a magnetic stir bar and pH probe. The solution pH was 2.66.

9. While stirring at 200 rpm, the solution was basified by adding 5 mL of 28% ammonium hydroxide; solids precipitated out of solution during the ammonium hydroxide addition and the final pH of the mixture was 9.13.

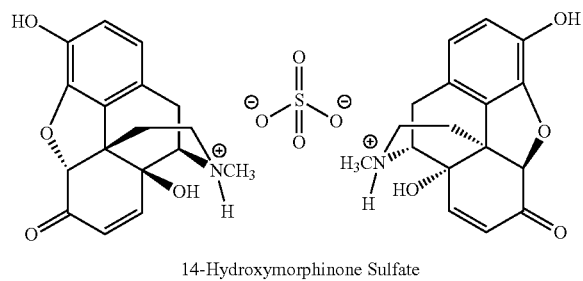

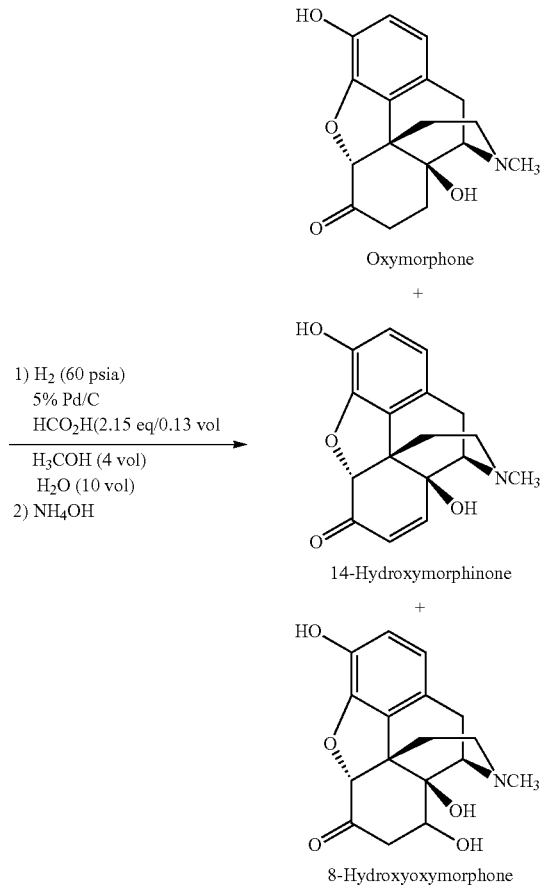

1. Into a 300 mL hydrogenation vessel equipped with a magnetic stir bar, 14-hydroxymorphinone sulfate obtained in Example 9 above (7.03 g, 10.1 mmol (calculated without water of crystallization)), deionized water (70 mL) and methanol (28 mL) were charged. The majority of solids dissolved into solution.

2. Formic acid (0.935 mL, 21.8 mmol) and 5% palladium on carbon (0.053 g) were added into the reaction mixture.

10. The mixture was allowed to stir (200 rpm) at 22° C. for an additional 45 minutes.

11. The solids were filtered under vacuum using a Buchner funnel with Whatman#2 filter paper, and the solids were washed with water (2×10 mL).

12. The solids were dried under vacuum on the Buchner funnel for 2 hours, before being transferred to a drying oven and dried under vacuum to a constant weight.

13. Isolated: 4.58 g (15.2 mmol, 75% yield) of oxymorphone (base) as a white crystalline powder as analyzed by the HPLC method of Example 11A. The HPLC area ratio of oxymorphone:14-hydroxymorphinone:8-hydroxyoxymorphone was 39,612,808:231 (6 ppm):9,518 (240 ppm). In other words, the composition contained 98.54% oxymorphone base, 6 ppm 14-hydroxymorphinone, and 240 ppm 8-hydroxyoxymorphone, based on HPLC area percent. The auto-scaled chromatograph and peak results from this analysis are depicted in FIG. 3.

Over all, about 3.64 molar equivalents of total acid per molar equivalent of oripavine were used in Examples 9 and 10. A molar excess of formic acid was present during the hydrogenation.

Example 11: HPLC Method

Example 11A

HPLC conditions for Examples 1 to 10 and 12 to 15 were as follows:
Instrument: Waters 2695 HPLC system with Waters 966 Photodiode Array Detector
Column: Waters XBridge C18 (150×3.0 mm; 3.5 µm)
Mobile phase:
    Solution A: 10 mMol (pH=10.2) ammonium bicarbonate in water
    Solution B: methanol
Flow rate: 0.30 mL/min
UV detection: 292 nm
Injection volume: 10 µl of a 1 mg/mL sample solution. Samples were
prepared by weighing 10±0.5 mg of sample and quantitatively transferring it to a 10 mL volumetric flask. The solids were dissolved in a 80:20 mixture of 0.085% phosphoric acid in water:methanol.
Column temperature: 30° C.
Run Time: 42 minutes
Gradient Conditions (Linear Concentration Changes):

TABLE 1

| Time | Flow | % A | % B |
|---|---|---|---|
| initial | 0.30 | 90.0 | 10.0 |
| 1.00 | 0.30 | 90.0 | 10.0 |
| 5.00 | 0.30 | 78.0 | 22.0 |
| 16.00 | 0.30 | 60.0 | 40.0 |
| 22.00 | 0.30 | 53.0 | 47.0 |
| 26.00 | 0.30 | 48.0 | 52.0 |
| 31.90 | 0.30 | 25.0 | 75.0 |
| 32.20 | 0.30 | 90.0 | 10.0 |
| 42.00 | 0.30 | 90.0 | 10.0 |

A representative HLPC chromatogram showing all relevant peaks is provided in FIG. 4. The components corresponding to the peaks are given in Table 2.

TABLE 2

| Components | Peak Abbreviations | Retention Time | RRT |
|---|---|---|---|
| 14-Hydroxymorphinone N-Oxide | FHM-N-Oxide | 3.227 | 0.15 |
| 10-Hydroxyoxymorphone | 10OH-OMN | 10.767 | 0.50 |
| 8-Hydroxyoxymorphone | 8OH-OMN | 14.641 | 0.68 |
| 14-Hydroxymorphinone | FHM | 17.544 | 0.82 |
| Hydromorphone | Hydromorphone | 19.120 | 0.89 |
| Oxymorphone | OMN | 21.461 | 1.00 |

TABLE 2-continued

| Components | Peak Abbreviations | Retention Time | RRT |
|---|---|---|---|
| 6β-Oxymorphol | 6bOH-OMN | 22.485 | 1.04 |
| 6α-Oxymorphol | 6aOH-OMN | 23.451 | 1.09 |
| Oripavine | ORP | 23.794 | 1.11 |
| 8,14-Dihydrooripavine | 8,14-DHO | 26.385 | 1.23 |
| Oxycodone | OXY | 31.228 | 1.46 |

The relative retention time (RRT) was calculated in relation to oxymorphone.

Estimated LOD was 1 ppm, estimated LOQ was 3 to 5 ppm.

Example 11B

HPLC conditions for Examples 16 to 17 were as follows:
HPLC unit: Agilent 1100 series HPLC
Detectors: Agilent 1100 Series DAD UV detector
    HP 1100 MSD mass detector
Column: Waters XSelect C18, 150×3.0 mm, 3.5 µm
Mobile phase:
    Solution A: 10 mMol (pH=10.2) ammonium bicarbonate in water
    Solution B: methanol
Flow rate: 0.30 mL/min
UV detection: 292 nm
Injection volume: 5 µl of a 1 mg/mL or 10 mg/mL sample solution. Samples were prepared by weighing 100±5 mg or 10±0.5 mg of sample and quantitatively transferring it to a 10 mL volumetric flask. The solids were dissolved in a 80:20 mixture of 0.085% phosphoric acid in water:methanol.
Column temperature: 30° C.
Run Time: 37 minutes
Gradient Conditions (Linear Concentration Changes):

TABLE 3

| Time | Flow | % A | % B |
|---|---|---|---|
| initial | 0.30 | 90.0 | 10.0 |
| 1.00 | 0.30 | 90.0 | 10.0 |
| 5.00 | 0.30 | 78.0 | 22.0 |
| 16.00 | 0.30 | 60.0 | 40.0 |
| 22.00 | 0.30 | 53.0 | 47.0 |
| 26.00 | 0.30 | 48.0 | 52.0 |
| 31.90 | 0.30 | 25.0 | 75.0 |
| 37.00 | 0.30 | 25.0 | 75.0 |

A representative HLPC chromatogram showing all relevant peaks is provided in FIG. 5. The components corresponding to the peaks are given in Table 4.

TABLE 4

| Components | Peak Abbreviations | mass | Retention Time | RRT |
|---|---|---|---|---|
| 8-Hydroxyoxymorphone | 8OH-OMN | 317 + 1 | 15.36 | 0.69 |
| 14-Hydroxymorphinone | FHM | 299 + 1 | 18.31 | 0.82 |
| 14-Hydroxymorphine | 6aOH-FHM | 301 + 1 | 19.95 | 0.90 |
| Oxymorphone | OMN | 301 + 1 | 22.25 | 1.00 |
| 6α-Oxymorphol | 6aOH-OMN | 303 + 1 | 24.41 | 1.10 |
| Oripavine | ORP | 297 + 1 | 26.59 | 1.20 |

The relative retention time (RRT) was calculated in relation to oxymorphone.
Estimated LOD was 1 ppm, estimated LOQ was 3 to 5 ppm.

Synthetic Example 12: Preparation of
14-Hydroxymorphinone Sulfate

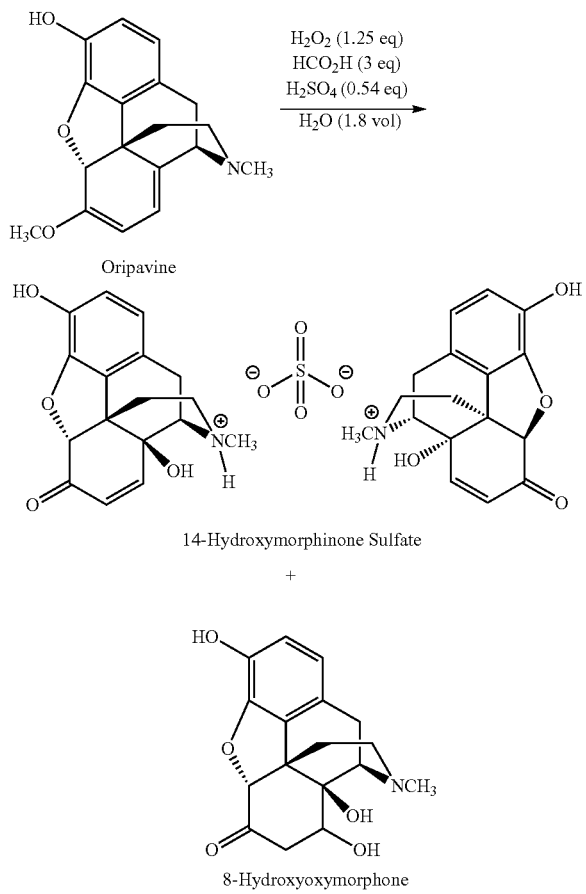

14-Hydroxymorphinone sulfate was prepared as follows:

1. In a 250 mL 3-necked flask equipped with a temperature probe and magnetic stirring bar, oripavine (10.0 g; 33.6 mmol) was dissolved in de-ionized water (18 mL) and 98% formic acid (3.88 mL, 101 mmol). The solution warmed up to 25° C. The solution was stirred (500 rpm) at 21° C. for 5 minutes.

2. Concentrated sulfuric acid (96%, 1.01 mL, 18.2 mmol) was added. The temperature rose to 35° C. The mixture was stirred (500 rpm) at 21° C. for 20 min.

3. Hydrogen peroxide (35 wt % in $H_2O$, 3.61 mL, 42.16 mmol) was added and the solution stirred (500 rpm) for 30 minutes at room temperature.

4. The mixture was then heated to 35° C. over 5 minutes and held at 35° C. and stirred (500 rpm) for 48 hours. Solids started to precipitate during the stirring after 10 hours.

5. To the resulting suspension was added 2-butanol (36 mL) and the stirring continued for 30 min. The temperature decreased from 35° C. to 26° C. during this time. The resulting slurry was cooled to 4° C. and rested at this temperature for 2 hours.

6. Filtration, washing with water:2-butanol (1:2, 12 mL) and thorough drying in vacuo afforded 14-hydroxymorphinone sulfate (10.5 g, 15.1 mmol (calculated without water of crystallization) 90% yield). No oripavine or 8-hydroxyoxymorphone was detectable by HPLC.

About 3.54 molar equivalents of total acid per molar equivalent of oripavine were used in this example. The molar ratio of sulfuric acid to formic acid was about 1:5.5. Precipitation was observed in step 4.

As compared to the previous examples (Examples 7 and 8), less total acid (formic acid plus sulfuric acid) was used (3.54 equivalents vs. 14.5 equivalents and 4.66 equivalents), more sulfuric acid per formic acid was used (1:5.5 vs. 1:17.1 and 1:6.4), and the conditions of the present reaction resulted in better yield (90% vs. 67% and 73.2% 14-hydroxymorphinone sulfate).

Synthetic Example 13: Preparation of
14-Hydroxymorphinone Sulfate

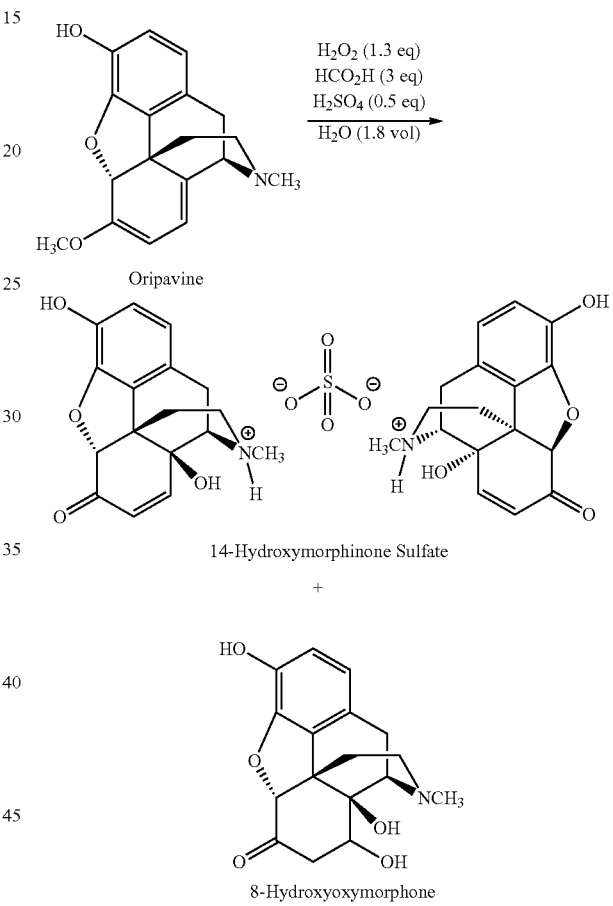

14-Hydroxymorphinone sulfate was prepared as follows:

1. In a multi-neck flask equipped with a magnetic stir bar and temperature probe, oripavine (9.96 g, 33.5 mmol) was dissolved in de-ionized water (18 mL) and 98% formic acid (3.88 mL, 101 mmol). The resulting solution was stirred at ambient temperature.

2. Concentrated sulfuric acid (96%, 0.92 mL, 16.8 mmol) was added and the mixture stirred at 450 rpm for 10 minutes. After addition of the sulfuric acid, the mixture heated to more than 30° C., then cooled again.

3. When the temperature of the solution had dropped below 25° C., hydrogen peroxide (35 wt % in $H_2O$, 3.8 mL, 44 mmol) was added and the solution stirred at 450 rpm for 20 minutes at room temperature.

4. The mixture was then stirred at 35° C. internal temperature for 48 hours.

5. To the warm mixture was added 2-butanol (36 mL) and the stirring continued for 30 min. The resulting slurry was cooled to 4° C. and rested at this temperature for 2 hours.

6. Filtration, washing with water:2-butanol (1:2, 12 mL) and thorough drying in vacuo afforded 14-hydroxymorphinone sulfate (9.94 g, 14.3 mmol (calculated without water of crystallization) 85.4% yield). No oripavine or 8-hydroxyoxymorphone was detectable by HPLC.

About 3.5 molar equivalents of total acid per molar equivalent of oripavine were used in this example. The molar ratio of sulfuric acid to formic acid was about 1:6.

In this example, 0.5 equivalents $H_2SO_4$ were used. As in Example 12 (where 0.55 equivalents $H_2SO_4$ were used), compared to the previous examples (Examples 7 and 8), less total acid (formic acid plus sulfuric acid) was used (3.5 equivalents vs. 14.5 equivalents and 4.66 equivalents), more sulfuric acid per formic acid was used (1:6 vs. 1:17.1 and 1:6.4), and the conditions of the present reaction resulted in better yield (85.4% vs. 67% and 73.2% 14-hydroxymorphinone sulfate).

Synthetic Example 14: Preparation of 14-Hydroxymorphinone Sulfate

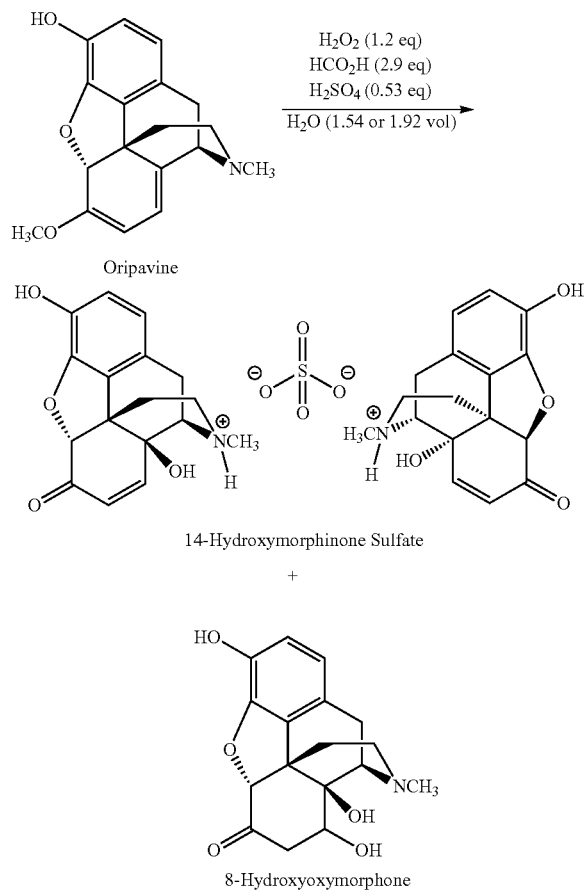

14-Hydroxymorphinone sulfate was prepared using two different amounts of water as follows:

1. In a multi-neck flask equipped with a magnetic stir bar and temperature probe, oripavine (10.4 g, 35.0 mmol) was dissolved in de-ionized water (16 or 20 mL, respectively) and 98% formic acid (3.88 mL, 101 mmol). The resulting solution was stirred at ambient temperature (500 rpm).

2. Concentrated sulfuric acid (96%, 1.02 mL, 18.5 mmol) was added and the mixture stirred at 500 rpm for 20 minutes. After addition of the sulfuric acid, the mixture heated to more than 30° C., then cooled again.

3. When the temperature of the solution had dropped below 25° C., hydrogen peroxide (35 wt % in $H_2O$, 3.62 mL, 42 mmol) was added and the solution stirred at 500 rpm for 30 minutes at room temperature.

4. The mixture was then stirred (750 rpm) at 35° C. internal temperature for 48 hours.

5. To the warm mixture was added 2-butanol (36 mL) and the stirring continued for 30 min. The resulting slurry was cooled to 4° C. and rested at this temperature for 2 hours.

6. Filtration, washing with water:2-butanol (1:2, 12 mL) and thorough drying in vacuo afforded 14-hydroxymorphinone sulfate (9.90 g, 14.21 mmol (calculated without water of crystallization) 81.2% yield for 16 mL water; 10.14 g, 14.56 mmol (calculated without water of crystallization) 83.2% yield for 20 mL water). No oripavine or 8-hydroxyoxymorphone was detectable by HPLC.

This Example shows the same advantages as pointed out in Example 12. Moreover, it shows that in addition to the 1.8 mL water per g oripavine as used in Example 12, 1.5 and 1.9 mL water per g oripavine can also advantageously be used.

Synthetic Example 15: Preparation of 14-Hydroxymorphinone Sulfate

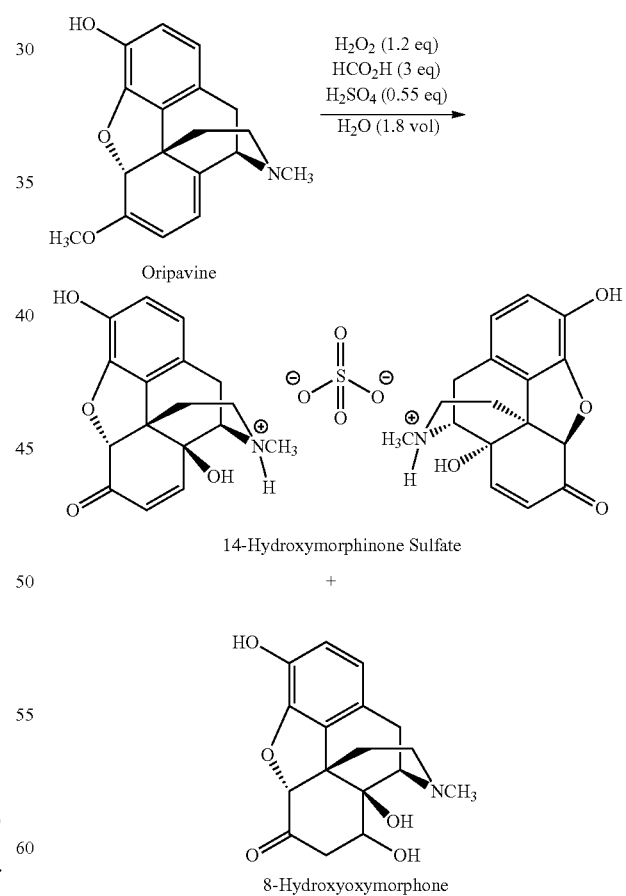

14-Hydroxymorphinone sulfate was prepared as follows:

1. In a multi-neck flask equipped with a magnetic stir bar and temperature probe, oripavine (10.04 g, 33.8 mmol) was dissolved in de-ionized water (18 mL) and 98% formic acid (3.88 mL, 101 mmol). The resulting solution was stirred (500 rpm) at ambient temperature.

2. Concentrated sulfuric acid (96%, 1.02 mL, 18.5 mmol) was added and the mixture stirred for about 20 minutes. After addition of the sulfuric acid, the mixture heated to more than 30° C., then cooled again.

3. When the temperature of the solution had dropped below 25° C., hydrogen peroxide (35 wt % in $H_2O$, 3.46 mL, 40.1 mmol, corresponding to 1.2 eq.) was added and the solution stirred for 30 minutes at room temperature.

4. The mixture was then stirred at 35° C. internal temperature for 48 hours.

5. To the warm mixture was added 2-butanol (36 mL) and the stirring continued for 30 min. The resulting slurry was cooled to 4° C. and rested at this temperature for 2 hours.

6. Filtration, washing with water:2-butanol (1:2, 12 mL) and thorough drying in vacuo afforded 14-hydroxymorphinone sulfate (10.07 g, 14.5 mmol (calculated without water of crystallization) 85.8% yield). No oripavine or 8-hydroxyoxymorphone was detectable by HPLC.

As in Example 12 (where 1.25 equivalents of hydrogen peroxide were used), compared to the previous examples (Examples 7 and 8), less total acid (formic acid plus sulfuric acid) was used (3.55 equivalents vs. 14.5 equivalents and 4.66 equivalents), more sulfuric acid per formic acid was used (1:5.5 vs. 1:17.1 and 1:6.4), and the conditions of the present reaction resulted in better yield (85.8% vs. 67% and 73.2% 14-hydroxymorphinone sulfate).

Example 16: Hydrogenation of 14-Hydroxymorphinone Sulfate in the Presence of Trifluoroacetic Acid and Propylene Glycol

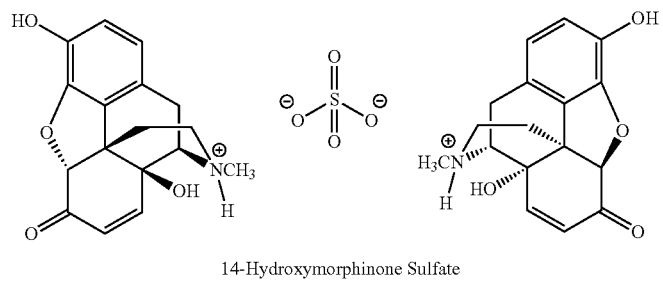

14-Hydroxymorphinone Sulfate

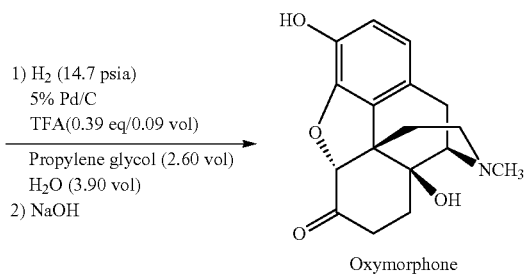

Oxymorphone 14-hydroxymorphinone sulfate (23.05 g, 66.19 mmol free 14-hydroxymorphinone, containing 0.17% 8-hydroxyoxymorphone) and Pd/C (70 mg, 5% Pd, 50% wet, Escat test kit 1471, Strem) were suspended in a mixture of water (90 mL) and propylene glycol (60 mL) in a 3 L flask. To this was added trifluoroacetic acid (2.0 mL, 26.12 mmol) and the mixture was hydrogenated with an overhead mounted balloon of hydrogen (ambient pressure, 14.7 psia) for 20h at 34° C. and 1100 rpm stirring with a stirring bar. HPLC analysis according to Example 11B showed complete conversion. To the mixture was added more Pd/C (70 mg, same batch as above) and the hydrogenation was continued for 6h at 34° C. until the result of the above mentioned HPLC analysis was known.

The mixture was filtered over Celite, washed with water (30 mL) and the filtrate basified with conc. aq. sodium hydroxide (30% w/w, ca. 8.5 mL) to pH 9. After cooling to 5° C. for 16h the mixture was filtered and the solids washed with 65% 2-butanol/water (2×30 mL), then 2-butanol (30 mL).

Drying in vacuo afforded oxymorphone (13.3 g, 67%) in 96.6% purity (average of 3 analyses, 0.26% standard deviation). No propylene glycol acetal, 14-hydroxymorphinone or 8-hydroxyoxymorphone were detectable in 1 mg/mL samples. Further analysis of highly concentrated (10 mg/mL, out of linearity range) samples detected no 8-hydroxyoxymorphone and no 14-hydroxymorphinone as well.

Example 17: Hydrogenation of 14-Hydroxymorphinone Sulfate in the Presence of Trifluoroacetic Acid and Ethylene Glycol

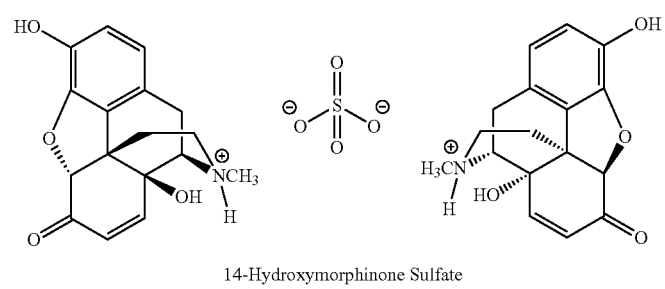

14-Hydroxymorphinone Sulfate

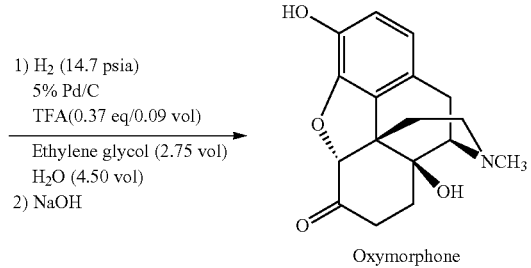

Oxymorphone 14-hydroxymorphinone sulfate (4.72 g, containing 15% water, 11.51 mmol free 14-hydroxymorphinone) and Pd/C (17 mg, 5% Pd, 50% wet, Escat test kit 1471, Strem) were suspended in a mixture of water (17.3 mL) and ethylene glycol (11 mL) in a 250 mL flask. To this was added trifluoroacetic acid (0.37 mL, 4.74 mmol) and the mixture hydrogenated with an overhead mounted balloon of hydrogen (ambient pressure, 14.7 psia) for 20h at 30° C. and 750 rpm stirring with a stirring bar. HPLC analysis according to Example 11B showed complete conversion with 0.23% of formed ethylene glycol acetal. The mixture was filtered over Celite, washed with water (5 mL) and the filtrate basified with conc. aq. sodium hydroxide (30% w/w, ca. 1.5 mL) to pH 9-9.5. After cooling to 5° C. for 2h the mixture was filtered and the solids washed with 20% 2-butanol/water (10 mL).

Drying in vacuo afforded oxymorphone (2.70 g, 8.97 mmol, 78%) in 99% purity. No ethylene glycol acetal, 14-hydroxymorphinone or 8-hydroxyoxymorphone were detectable.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

The invention claimed is:

1. A process for preparing oxymorphone or a salt or solvate thereof from oripavine, the process comprising or consisting of the steps

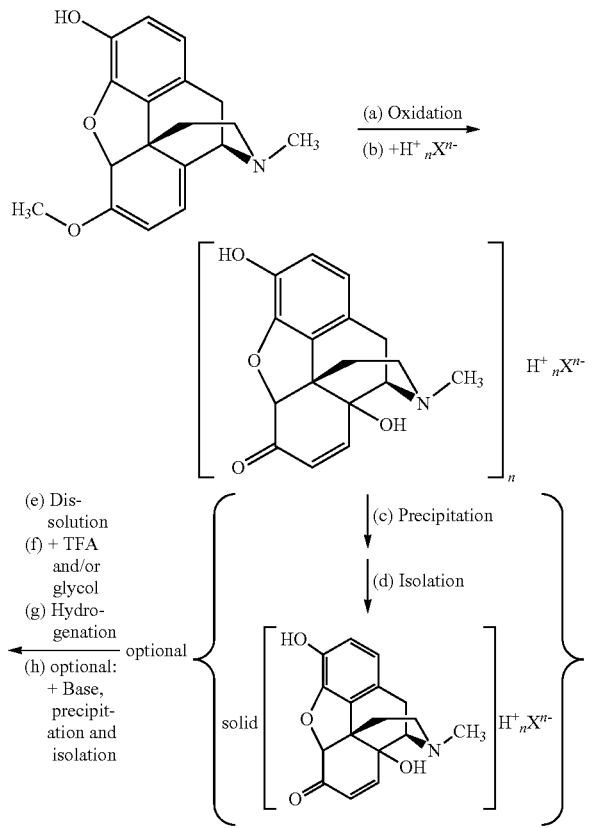

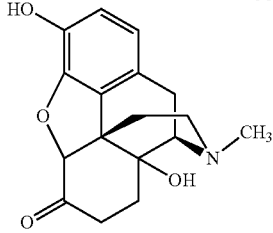

(a) oxidizing the oripavine to 14-hydroxymorphinone;
(b) adding an acid $H^+_n X^{n-}$ to the reaction mixture before, during and/or after the oxidation reaction;
(c) optionally precipitating the resulting 14-hydroxymorphinone as 14-hydroxymorphinone salt or a solvate thereof;
(d) optionally isolating the precipitated 14-hydroxymorphinone salt or solvate thereof;
(e) providing a solution or suspension of the 14-hydroxymorphinone salt or a solvate thereof;
(f) adding trifluoroacetic acid and/or glycol;
(g) reducing the 14-hydroxymorphinone present in the solution or suspension to the oxymorphone by hydrogenation; and
(h) optionally adding a base, thus raising the pH where the oxymorphone precipitates as its free base, and isolating the oxymorphone as its free base or a solvate thereof, wherein
$X^{n-}$ is an anion selected from the group consisting of $Cl^-$, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof; and
n is 1, 2, or 3.

2. The process of claim 1, wherein trifluoroacetic acid and a glycol are added in step (f).

3. The process of claim 1, wherein n is 2 and $X^{n-}$ is $SO_4^{2-}$.

4. The process of claim 1, wherein the amount of trifluoroacetic acid is 99 mol % or less as compared to the molar amount of 14-hydroxymorphinone contained in the 14-hydroxymorphinone salt.

5. The process of claim 4, wherein the amount of trifluoroacetic acid is from 30 mol % to 50 mol % as compared to the molar amount of 14-hydroxymorphinone contained in the 14-hydroxymorphinone salt.

6. The process of claim 1, wherein the glycol is selected from the group consisting of ethylene glycol, propylene glycol, 1,3-propanediol, 1,2-butanediol, 1,3-butanediol, neopentylglycol, and mixtures thereof.

7. The process of claim 6, wherein the glycol is ethylene glycol, propylene glycol, or a mixture thereof.

8. The process of claim 1, wherein the glycol added in step (f) is in the range of 1 to 8 volumes in mL in relation to the weight in g of the 14-hydroxymorphinone salt.

9. The process of claim 1, wherein the hydrogenation in step (g) is performed with $H_2$ and a hydrogenation catalyst.

10. The process of claim 1, wherein a mixture of water and the glycol is used as solvent, wherein the mixture is in a range from 20:80 to 45:55 glycol:water.

11. The process of claim 1, additionally comprising the step (h) of adding the base, thus raising the pH to a pH where the oxymorphone precipitates as its free base, and isolating the oxymorphone as its free base or a solvate thereof.

12. The process of claim 11, wherein the base added in step (h) is NaOH.

13. The process of claim 1, wherein the 14-hydroxymorphinone salt or a solvate thereof is 14-hydroxymorphinone sulfate or a solvate thereof.

14. The process of claim 1, wherein the 14-hydroxymorphinone salt or solvate thereof is precipitated and isolated in the steps (c) and (d).

15. The process of claim 1, wherein the oripavine is oxidized in the step (a) in the presence of an oxidizing agent formed in situ in a reaction mixture comprising formic acid and hydrogen peroxide.

16. The process of claim 1, wherein the acid is added to the reaction mixture in the step (b) before or during the oxidation reaction.

* * * * *